(12) United States Patent
James et al.

(10) Patent No.: US 7,612,084 B2
(45) Date of Patent: Nov. 3, 2009

(54) AMINE DERIVATIVES FOR THE TREATMENT OF ASTHMA AND COPD

(75) Inventors: Kim James, Sandwich (GB); Lyn Howard Jones, Sandwich (GB); David Anthony Price, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/725,335

(22) Filed: Mar. 19, 2007

(65) Prior Publication Data

US 2007/0265303 A1    Nov. 15, 2007

Related U.S. Application Data

(60) Provisional application No. 60/784,519, filed on Mar. 20, 2006, provisional application No. 60/803,745, filed on Jun. 2, 2006.

(51) Int. Cl.
  *A61K 31/44*    (2006.01)
(52) U.S. Cl. ........................ 514/299; 546/112
(58) Field of Classification Search ............. 514/183
  See application file for complete search history.

(56) References Cited

U.S. PATENT DOCUMENTS

| 4,853,381 | A |  | 8/1989 | Finch et al. ............. 514/211 |
| 2003/0158155 | A1 | * | 8/2003 | Hori et al. .............. 514/150 |
| 2005/0215590 | A1 |  | 9/2005 | Brown et al. ............ 514/317 |
| 2005/0222128 | A1 |  | 10/2005 | Brown et al. ............ 514/218 |
| 2005/0256114 | A1 |  | 11/2005 | Grauert et al. ........... 514/230.5 |
| 2008/0206808 | A1 | * | 8/2008 | DeFrees et al. .......... 435/68.1 |
| 2009/0029958 | A1 | * | 1/2009 | Alcaraz et al. ........... 514/171 |

FOREIGN PATENT DOCUMENTS

| EP | 0325571 | 8/1991 |
| WO | WO 9411337 | 5/1994 |
| WO | WO 02/34245 A2 * | 5/2002 |
| WO | WO 0234245 | 5/2002 |
| WO | WO 2004032921 | 4/2004 |
| WO | WO 2004074246 | 9/2004 |
| WO | WO 2004074276 | 9/2004 |
| WO | WO 2004074812 | 9/2004 |
| WO | WO 2004089892 | 10/2004 |
| WO | WO 2005012227 | 2/2005 |
| WO | WO 2005080324 | 9/2005 |
| WO | WO 2005092861 | 10/2005 |

OTHER PUBLICATIONS

K. Demirkan et al, Pharmacotherapy, vol. 19, #7, Jul. 1999, pp. 838-843.

* cited by examiner

*Primary Examiner*—Ardin Marschel
*Assistant Examiner*—Meghan Finn
(74) *Attorney, Agent, or Firm*—Gregg C. Benson; Robert T. Ronau

(57) ABSTRACT

The invention relates to compounds of formula (1)

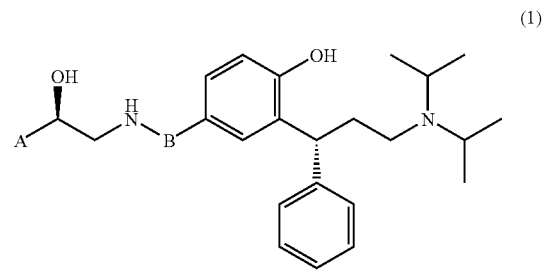

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

4 Claims, No Drawings

AMINE DERIVATIVES FOR THE TREATMENT OF ASTHMA AND COPD

STATEMENT OF RELATED CASES

Benefit is claimed from U.S. Provisional Application Ser. No. 60/784,519, filed 20 Mar. 2006 and U.S. Provisional Application Ser. No. 60/803,745, filed 2 Jun. 2006, both incorporated herein by reference.

BACKGROUND OF THE INVENTION $\beta_2$ adrenergic agonists and cholinergic muscarinic antagonists are well-established therapeutic agents for the treatment of obstructive respiratory diseases such as COPD and Asthma. Currently used inhaled $\beta_2$ agonists include both short acting agents such as salbutamol (q.i.d.), and terbutaline (t.i.d) and longer acting agents such as salmeterol, and formoterol (b.i.d.) and produce bronchodilation via stimulation of adrenergic receptors on airway smooth muscle. Inhaled Muscarinic antagonists in clinical use include the short acting ipratropium bromide (q.i.d.), oxitropium bromide (q.i.d) and the long acting tiotropium (q.d.). Muscarinic antagonists produce bronchodilation by inhibiting the cholinergic tone of airways primarily by antagonising the action of acetylcholine on muscarinic receptors present on airway smooth muscle. A number of published studies have demonstrated that the combined administration of inhaled $\beta_2$agonists with inhaled muscarinic antagonists (whether short or long acting) to patients with obstructive lung disease results in superior improvements in lung function, symptoms and quality of life measures compared to patients receiving either single class of agent alone. Studies to date have been restricted to combination studies with single pharmacology agents, however combination of both pharmacologies within a single molecule would be desirable as this could yield increased bronchodilator efficacy with similar therapeutic index to the single agents or similar efficacy with superior therapeutic index. In addition, combining both pharmacologies in a single molecule would allow the potential for combination with anti-inflammatory agents thus giving a triple therapy from a single inhaler.

SUMMARY OF THE INVENTION

The invention relates to the compounds of general formula (1):

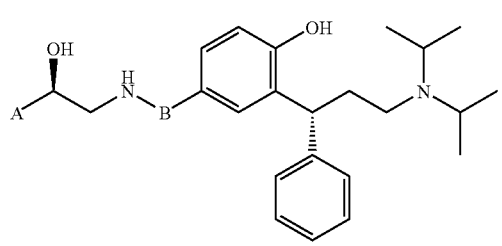

wherein A is selected from:

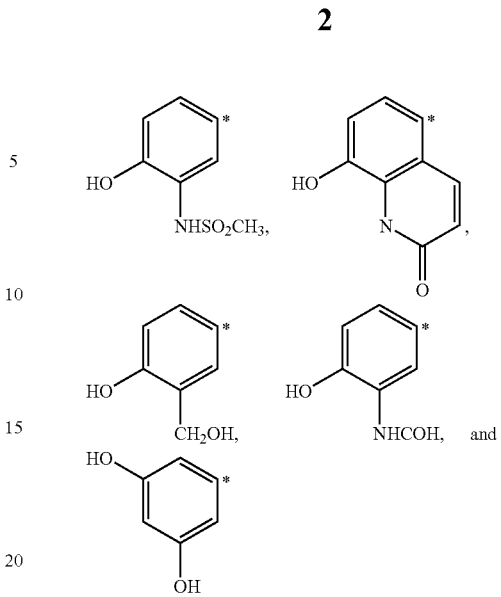

wherein * represent the attachment point of A to the carbon bearing the hydroxy;

and B is selected from:

1) —$(CH_2)_2$—$(CH_2)_m$—$X^1$—$(CH_2)_n$—* wherein $X^1$ is O or S, m is an integer from 0 to 9, n is an integer from 0 to 9 and n+m is comprised between 4 to 9 inclusive;

2) $C_6$-$C_{12}$ alkylene optionally substituted with one or two $C_1$-$C_4$ alkyl;

3) a group of formula

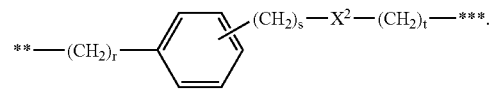

wherein $X^2$ is O or S, r is an integer from 2 to 7, s is an integer from 0 to 6, t is an integer from 0 to 6, s+t is comprised between 1 to 6 inclusive and r+s+t is comprised between 3 to 8 inclusive; and 4) a group of formula

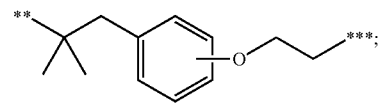

representing the attachment point of B to the adjacent NH group and * representing the attachment point of B to the adjacent phenyl group;

and quaternary ammonium salts thereof or, if appropriate, their pharmaceutically acceptable salts and/or isomers, tautomers, solvates or isotopic variations thereof.

The compounds of formula (1) are β2 adrenergic receptor agonists and muscarinic receptor antagonists that are particularly useful for the treatment of diseases and/or conditions involving said receptors, by showing excellent potency, in particular when administered via the inhalation route.

The compounds of the formula (1)

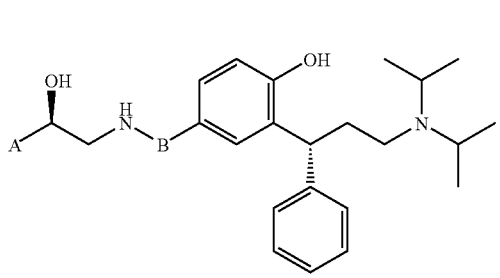

can be prepared using conventional procedures such as by the following illustrative methods in which A and B are as previously defined for the compounds of the formula (1) unless otherwise stated.

The amine derivative of the formula (1) may be prepared by reaction of an amine of formula (2):

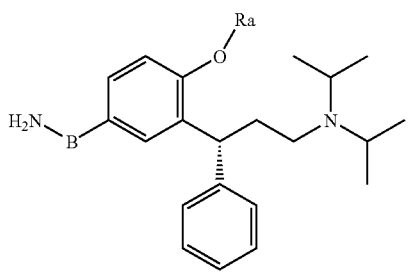

wherein Ra represents hydrogen or a suitable hydroxy protecting group, preferably benzyl, with a bromide of formula (3):

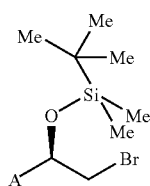

wherein A is as defined above for the compounds of formula (1). Preferably the hydroxy groups of A are protected with suitable hydroxyl protecting groups. A preferred hydroxyl protecting group is benzyl.

In a typical procedure, the amine of formula (2) is reacted with a bromide of formula (3) optionally in the presence of a solvent or mixture of solvents (e.g. dimethyl sulphoxide, toluene, N,N-dimethylformamide, propionitrile, acetonitrile), optionally in the presence of a suitable base (e.g. triethylamine, diisopropylethylamine, potassium carbonate, potassium hydrogen carbonate, sodium hydrogen carbonate) at a temperature comprised between 80° C. and 120° C., for 12 to 48 hours. The protecting groups can then be removed using standard methodology for cleaving oxygen protecting groups such as those found in the text book T. W. Greene, Protective Groups in Organic Synthesis, A. Wiley-Interscience Publication, 1981.

The bromides of formula (3) may be prepared according to the methods of WO2005/080324, US2005/222128, WO2004/032921, US2005/215590, WO2005/092861.

The amine of formula (2) may be prepared from the corresponding protected amine of formula (4):

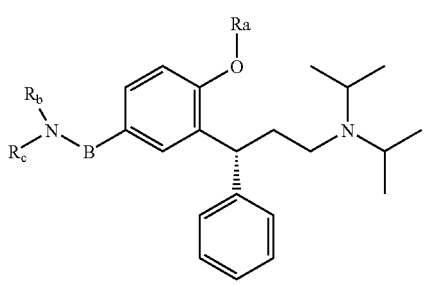

wherein $R_b$ and $R_c$ represent any suitable substituents so that the bonds between the N atom and $R_b$ and the N atom and $R_c$ may be easily cleaved to give the free amine of formula (2) using standard methodology for cleaving nitrogen protecting groups such as those found in the text book T. W. Greene, Protective Groups in Organic Synthesis, A. Wiley-Interscience Publication, 1981. For example $R_b$ and $R_c$ could be selected from allyl, benzyl, t-butyl carbamate or when joined together to form phthalimide. Preferably $R_b$ and $R_c$ are both tertbutyl carbamate or $R_b$ is H and $R_c$ is tertbutyl carbamate.

The amine of formula (4), wherein Ra is benzyl and B is selected from $(CH_2)_2$—$(CH_2)_m$—$X^1$—$(CH_2)_n$ where n is 0 and m and $X^1$ are as defined for compounds of formula (1) or a group of formula

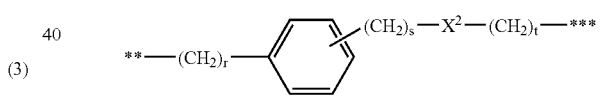

wherein t is 0 and r, s and $X^2$ are as defined for compounds of formula (1);

may be prepared by reaction of a compound of formula (5):

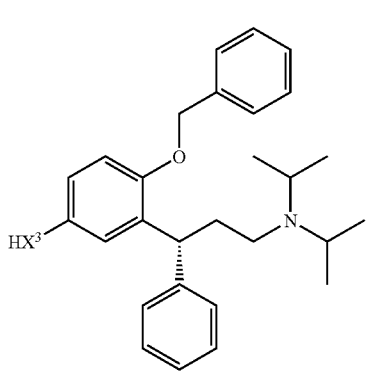

wherein $X^3$ is O or S, with a compound of formula (6):

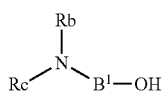

(6)

wherein $B^1$ is $(CH_2)_2-(CH_2)_m$ or a group of formula:

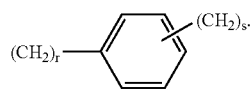

In a typical procedure, the alcohol compound of formula (6) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the compound of formula (5) in the presence of a solvent or mixture of solvents (e.g. dimethyl sulphoxide, toluene, N,N-dimethylformamide, acetonitrile, tetrahydrofuran) optionally in the presence of a suitable base (e.g. triethylamine, diisopropylethylamine, potassium carbonate, potassium hydrogen carbonate, sodium hydrogen carbonate) at a temperature comprised between 60° C. and 120° C., for 4 to 48 hours.

Alternatively, a Mitsunobu protocol may be employed (e.g. diethyl azodicarboxylate/triphenylphosphine) in the presence of a solvent or mixture of solvents (e.g. toluene, acetonitrile, tetrahydrofuran) at a temperature comprised between 25° C. and 60° C., for 2 to 4 hours.

The compound of formula (5) wherein $X^3$ is O may be prepared from the aldehyde of formula (7):

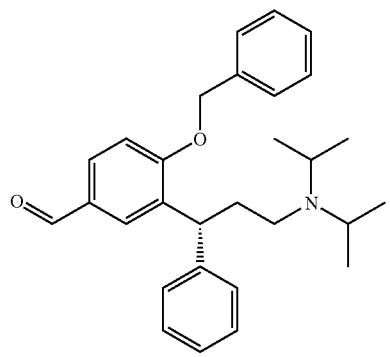

(7)

In a typical procedure, the aldehyde (7) is treated with an oxidant (e.g. hydrogen peroxide; metachloroperbenzoic acid) in the presence of a solvent or mixture of solvents (e.g. methanol, water, acetonitrile), in the presence of an acid (e.g. sulphuric acid) at a temperature comprised between 25° C. and 60° C., for 6 to 24 hours.

The aldehyde of formula (7) may be prepared according to the method of WO 2005/012227.

The compound of formula (5) wherein $X^3$ is S may be prepared from an halide of formula (13):

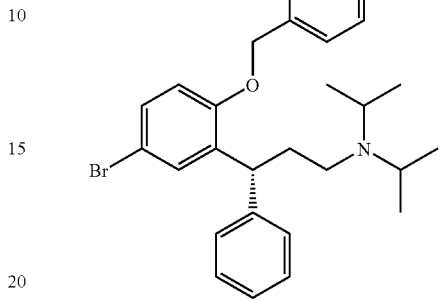

(13)

In a typical procedure, the said halide (13) is reacted with triisopropylsilanethiol in the presence of a suitable palladium catalyst (e.g. palladium acetate/tri-ortho-tolylphosphine of formula $Pd(OAc)_2/\{P(o-Tol)_3\}_2$) in the presence of a solvent or mixture of solvents (e.g. toluene, acetonitrile, hexane) in the presence of a base (e.g. triethylamine, diisopropylethylamine, potassium carbonate, sodium hydrogen carbonate). Preferably, the reaction is carried out at a temperature comprising between 70° C. and 110° C. for 4 to 16 hours. The product silyl thioether is then deprotected using the methods found in the textbook T. W. Greene, Protective Groups in Organic Synthesis, A. Wiley-Interscience Publication, 1981.

The aryl bromide of formula (13) may be prepared according to the method of WO 1994/11337.

The alcohol compound of formula (6) may be prepared from commercial amines using the methods found in the textbook T. W. Greene, Protective Groups in Organic Synthesis, A. Wiley-Interscience Publication, 1981.

The amine of formula (4), wherein B is selected from
$(CH_2)_2-(CH_2)_m-X^1-(CH_2)_n$ wherein $X^1$ is O or S, m is an integer from 0 to 9, n is an integer from 3 to 9 and n+m is comprised between 4 to 9;

$C_6$-$C_{12}$ alkylene optionally substituted with one or two $C_1$-$C_4$ alkyl;

a group of formula:

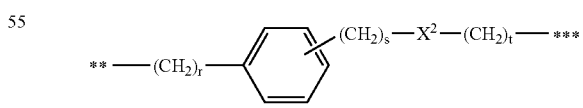

wherein $X^2$ is O or S, r is an integer from 2 to 7, s is an integer 0 to 6 and t is an integer from 3 to 6 and s+t is comprised between 3 to 6 and r+s+t is comprised between 5 to 8, may be prepared from the amine of formula (8):

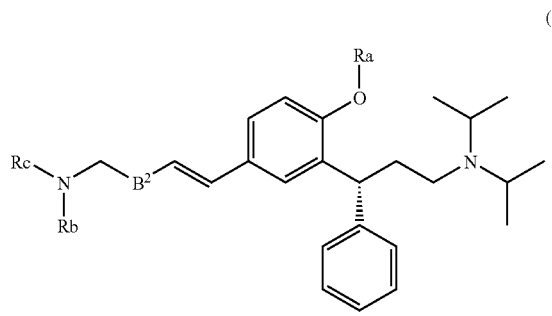

(8)

wherein $B^2$ is —$CH_2$—$(CH_2)_m$—$X^1$—$(CH_2)_{n1}$ wherein $X^1$ is O or S, m is an integer from 0 to 9, $n_1$ is an integer from 1 to 7 and $n_1+m$ is comprised between 2 to 7;

$C_3$-$C_8$ alkylene optionally substituted with one or two $C_1$-$C_4$ alkyl;

a group of formula

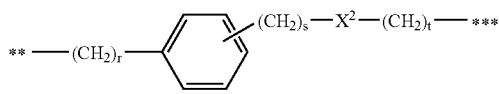

wherein $X^2$ is O or S, $r_1$ is an integer from 1 to 6, s is an integer 0 to 6 and $t_1$ is an integer from 1 to 4 and $s+t_1$ is comprised between 1 to 4 and $r_1+s+t_1$ is comprised between 2 to 5.

In a typical procedure, the amine of formula (8) is treated to hydrogenation using a metal catalyst (e.g palladium on carbon; platinum oxide) in the presence of a solvent (e.g. methanol, ethanol, ethyl acetate, tetrahydrofuran) with a hydrogen source (e.g. ammonium formate; formic acid, hydrogen) at a temperature comprised between 20° C. and 90° C., for 1 to 6 hours. The amine of formula (8) may be prepared from reaction of the aldehyde of formula (7) as previously described with a phosphonium salt of formula (9):

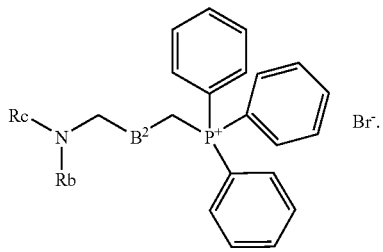

(9)

In a typical procedure, the phosphonium salt (9) treated with a suitable base (e.g. sodium hydride, triethylamine, n-butyl lithium, hexamethyldisilazide) then reacted with the aldehyde (8) in the presence of a solvent or mixture of solvents (e.g. toluene, tetrahydrofuran, acetonitrile). Preferably, the reaction is carried out at a temperature comprised between 50° C. and 110° C. for 4 to 24 hours.

The phosphonium salt (9) may be prepared by reaction of triphenyl phosphine with the bromide of formula (10):

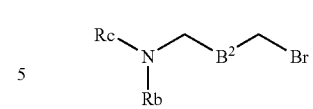

(10)

In a typical procedure the bromide of formula (10) is reacted with triphenyl phosphine, optionally in the presence of a solvent or mixture of solvents (e.g. toluene, tetrahydrofuran, acetonitrile). Preferably, the reaction is carried out at a temperature comprised between 50° C. and 110° C. for 1 to 5 days.

The bromide of formula (10) may be formed by the reaction of a suitable amine or amine equivalent with a dibromide of formula (11):

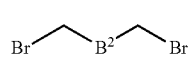

(11)

In a typical procedure, the dibromide of formula (11) is reacted with a suitable amine or amine equivalent (e.g. phthalimide, di-tert-butyl iminodicarbamate) in the presence of a solvent or mixture of solvents (e.g. toluene, tetrahydrofuran, acetonitrile) and with a suitable base (e.g. sodium hydride, triethylamine, n-butyl lithium). Preferably, the reaction is carried out at a temperature comprised between 25° C. and 110° C. for 4 to 24 hours.

The dibromide (11) may either be commercial or formed from a dialcohol of formula (12):

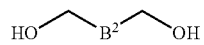

(12)

using standard methods (e.g. triphenylphosphine/carbon tetrabromide), in the presence of a solvent or mixture of solvents (e.g. dichloromethane, toluene, N,N-dimethylformamide, propionitrile, acetonitrile).

Compounds of formula (12) are commercially available or can be easily prepared by a man skilled in the art using commercially available materials and standard methods.

Alternatively the amine of formula (4), wherein B is selected from:

$(CH_2)_2$—$(CH_2)_m$—$X^1$—$(CH_2)_n$ wherein $X^1$ is O or S, m is an integer from 0 to 9, n is an integer from 3 to 9 and n+m is comprised between 4 to 9;

$C_6$-$C_{12}$ alkylene optionally substituted with one or two $C_1$-$C_4$ alkyl;

or a group of formula:

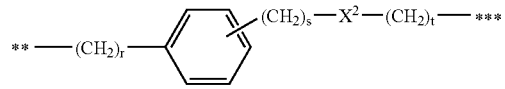

wherein $X^2$ is O or S, r is an integer from 2 to 7, s is an integer 0 to 6 and t is an integer from 3 to 6 and s+t is comprised between 3 to 6 inclusive and r+s+t is comprised between 5 to 8 inclusive, may be prepared by reaction of the bromide of formula (13):

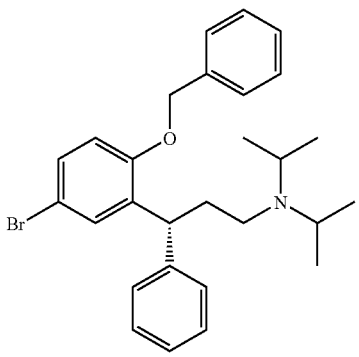
(13)

with the alkene of formula (14):

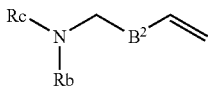
(14)

wherein $B^2$ is as defined above.

In a typical procedure, the aryl halide of formula (13) is reacted with the alkene of formula (14) in the presence of a suitable palladium catalyst (e.g. palladium acetate/tri-ortho-tolylphosphine of formula $Pd(OAc)_2/\{P(o-Tol)_3\}_2$) in the presence of a solvent or mixture of solvents (e.g. toluene, acetonitrile, hexane) in the presence of a base (e.g. triethylamine, diisopropylethylamine, potassium carbonate, potassium hydrogen carbonate). Preferably, the reaction is carried out at a temperature comprising between 70° C. and 110° C. for 4 to 16 hours.

The aryl bromide of formula (13) may be prepared according to the method of WO 1994/11337.

The amine of formula (14) may be prepared from commercial halides of formula (15):

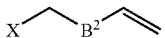
(15)

wherein X is Cl, Br or I. In a typical procedure the halide (15) is reacted with a suitable amine or amine equivalent (e.g. phthalimide, di-tert-butyl iminodicarbamate) in the presence of a solvent or mixture of solvents (e.g. toluene, tetrahydrofuran, acetonitrile) and with a suitable base (e.g. sodium hydride, triethylamine, n-butyl lithium). Preferably, the reaction is carried out at a temperature comprised between 25° C. and 110° C. for 4 to 24 hours.

Alternatively if amine (14) is of the formula (16):

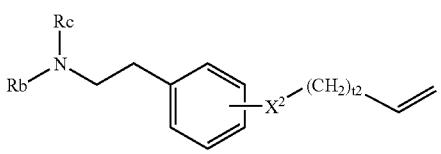
(16)

wherein $X^2$ is O or S and $t_2$ is an integer from 1 to 4, then this may be formed by reaction of a compound of formula (17):

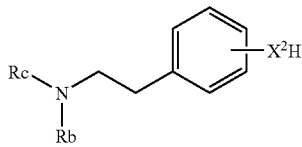
(17)

with commercial halides of formula (18):

(18)

wherein X is Cl, Br or I.

In a typical procedure the compound of formula (17) is treated with the halide (18) in the presence of a solvent or mixture of solvents (e.g. dimethyl sulphoxide, toluene, N,N-dimethylformamide, acetonitrile, tetrahydrofuran), optionally in the presence of a suitable base (e.g. triethylamine, diisopropylethylamine, potassium carbonate, potassium hydrogen carbonate, sodium hydride) at a temperature comprised between 0° C. and 80° C., for 1 to 48 hours.

Compounds of formula (17) where $X^2$ is O may be prepared from commercial 3-(2-aminoethyl)phenol or 4-(2-aminoethyl)phenol using the methods found in the textbook T. W. Greene, Protective Groups in Organic Synthesis, A. Wiley-Interscience Publication, 1981.

Compounds of formula (17) where $X^2$ is S may be formed from a halide of formula (17a):

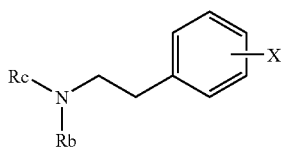
(17a)

wherein X is Cl, Br or I.

In a typical procedure, the said halide (17a) is reacted with triisopropylsilanethiol in the presence of a suitable palladium catalyst (e.g. palladium acetate/tri-ortho-tolylphosphine of formula $Pd(OAc)_2/\{P(o-Tol)_3\}_2$) in the presence of a solvent or mixture of solvents (e.g. toluene, acetonitrile, hexane) in the presence of a base (e.g. triethylamine, diisopropylethylamine, potassium carbonate, sodium hydrogen carbonate). Preferably, the reaction is carried out at a temperature comprising between 70° C. and 110° C. for 4 to 16 hours. The product silyl thioether is then deprotected using the methods found in the textbook T. W. Greene, Protective Groups in Organic Synthesis, A. Wiley-Interscience Publication, 1981.

The halides of formula (17a) may be prepared from commercial halides of formula (17b):

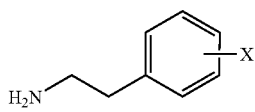
(17b)

using the methods found in the textbook T. W. Greene, Protective Groups in Organic Synthesis, A. Wiley-Interscience Publication, 1981.

Alternatively if the amine (4) is of the formula (19):

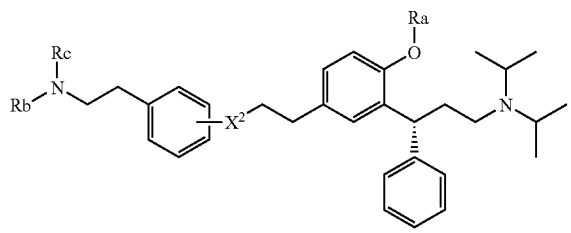
(19)

then it may be formed by reaction of a compound of formula (17) with a compound of formula (20):

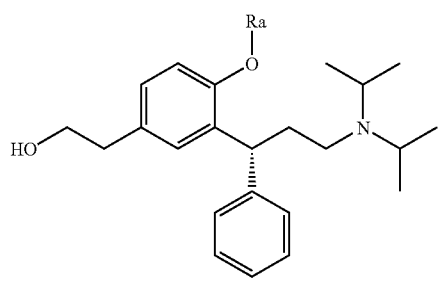
(20)

In a typical procedure, the compound of formula (20) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the compound of formula (17) in the presence of a solvent or mixture of solvents (e.g. dimethyl sulphoxide, toluene, N,N-dimethylformamide, acetonitrile, tetrahydrofuran) optionally in the presence of a suitable base (e.g. triethylamine, diisopropylethylamine, potassium carbonate, potassium hydrogen carbonate) at a temperature comprised between 60° C. and 120° C., for 4 to 48 hours.

Alternatively, a Mitsunobu protocol may be employed (e.g. diethyl azodicarboxylate/triphenylphosphine) in the presence of a solvent or mixture of solvents (e.g. toluene, acetonitrile, tetrahydrofuran) at a temperature comprised between 25° C. and 60° C., for 2 to 4 hours.

The compound of formula (20) can be formed from an alkene of formula (21):

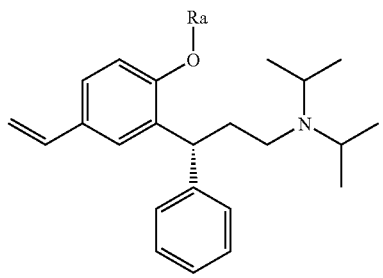
(21)

by reaction with a boronating agent (e.g. borane, 9-Borabicyclo[3.3.1]nonane) in the presence of a suitable solvent (e.g. tetrahydrofuran) at a temperature comprising between 60° C. and 100° C. for 4 to 24 hours. Followed by oxidation with hydrogen peroxide in a suitable solvent or mixture of solvents (e.g. water, methanol, tetrahydrofuran) with a suitable base (e.g. sodium hydroxide). The alkene of formula (21) may be formed from the aryl bromide (13) by reaction with a suitable vinyl compound (e.g. vinyltributylstannane; potassium vinyltetrafluoroborate; 2,4,6-trivinylcycloboroxane pyridine complex). In a typical procedure, the aryl halide (13) and the vinyl compound are reacted in the presence of a suitable palladium catalyst (e.g. palladium acetate/tri-ortho-tolylphosphine of formula $Pd(OAc)_2/\{P(o\text{-}Tol)_3\}_2$) in the presence of a solvent or mixture of solvents (e.g. toluene, acetonitrile, hexane), in the presence of a base (e.g. triethylamine, diisopropylethylamine, potassium carbonate, potassium hydrogen carbonate). Preferably, the reaction is carried out at a temperature comprised between 70° C. and 110° C. for 4 to 16 hours.

Alternatively, the compound of formula (20) can be formed from an ester of formula (37):

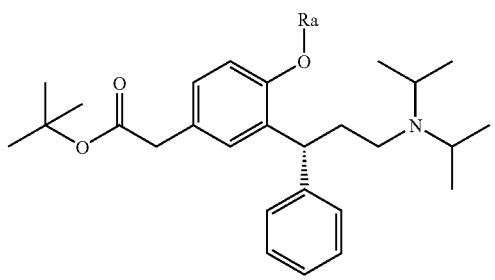
(37)

by reaction with a reducing agent (e.g. lithium aluminium hydride, lithium borohydride) in the presence of a suitable solvent (e.g. tetrahydrofuran) at a temperature comprising between 0° C. and 100° C. for 4 to 24 hours.

The ester of formula (37) may be formed from the aryl bromide of formula (13) as here before described by reaction with an anion of tert-butylacetate under palladium catalysis. In a typical procedure, the aryl halide (13) and the ester anion are reacted in the presence of a suitable palladium catalyst (e.g. palladium dibenzylidene acetate or palladium acetate/tri-ortho-tolylphosphine of formula $Pd(OAc)_2/\{P(o\text{-}Tol)_3\}_2$) in the presence of a solvent or mixture of solvents (e.g. toluene, acetonitrile, hexane), in the presence of a base (e.g. triethylamine, diisopropylethylamine, potassium carbonate, potassium hydrogen carbonate, lithium hexamethyldisilazide). Preferably, the reaction is carried out at a temperature comprised between 0° C. and 110° C. for 4 to 16 hours.

Alternatively, the amine of formula (2) may be prepared from the corresponding nitrile of formula (22):

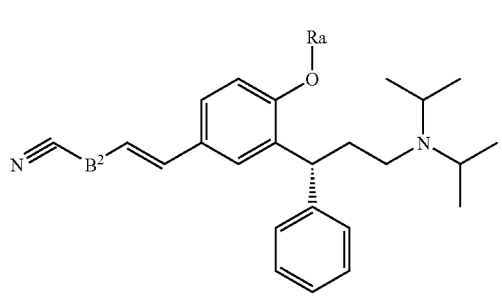

(22)

wherein $B^2$ is as defined above.

In a typical procedure, the nitrile of formula (22) is treated to hydrogenation using a metal catalyst or combination of catalysts (e.g palladium on carbon; platinum oxide, Raney-Nickel®) in the presence of a solvent (e.g. methanol, ethanol, ethyl acetate, tetrahydrofuran) with a hydrogen source (e.g. ammonium formate, formic acid, hydrogen) at a temperature comprised between 20° C. and 90° C., for 1 to 6 hours.

The nitrile of formula (22) may be prepared by reaction of the aryl bromide (13) with an alkene of formula (23):

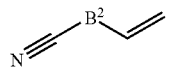

(23)

In a typical procedure, the aryl halide of formula (13) is reacted with the alkene of formula (14) in the presence of a suitable palladium catalyst (e.g. palladium acetate/tri-ortho-tolylphosphine of formula $Pd(OAc)_2/\{P(o\text{-}Tol)_3\}_2$) in the presence of a solvent or mixture of solvents (e.g. toluene, acetonitrile, hexane) in the presence of a base (e.g. triethylamine, diisopropylethylamine, potassium carbonate, potassium hydrogen carbonate). Preferably, the reaction is carried out at a temperature comprising between 70° C. and 110° C. for 4 to 16 hours.

The alkene of formula (23) may be commercial.

Alternatively, if alkene (23) is of formula (24) as follows:

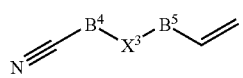

(24)

wherein $X^3$ is O or S, $B^4$ is $CH_2$—$(CH_2)_m$ wherein m is an integer from 0 to 9 and $B^5$ is $(CH_2)_{n1}$ wherein $n_1$ is an integer from 1 to 7, and $n_1$+m is comprised between 2 to 7 inclusive, or, $B^4$ is a group of formula:

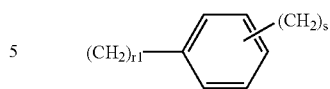

wherein $r_1$ is an integer from 1 to 6, s is an integer 0 to 6, and $B^5$ is a group $(CH_2)_{t1}$ wherein $t_1$ is an integer from 1 to 4, and $s+t_1$ is comprised between 1 to 4 inclusive and $r_1+s+t_1$ is comprised between 2 to 5 inclusive;

then said compound of formula (24) can be formed by reaction of a compound of formula (25):

(25)

with a compound of formula (26):

(26)

In a typical procedure, one of the compound (25) or (26) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the other compound (26) or (25) in the presence of a solvent or mixture of solvents (e.g. water, dimethyl sulphoxide, toluene, N,N-dimethylformamide, acetonitrile, tetrahydrofuran, dichloromethane) in the presence of a suitable base (e.g. sodium hydroxide, potassium tert-butoxide, sodium hydride) optionally in the presence of a phase transfer catalyst (e.g. tetra-ethylammonium bromide) at a temperature comprised between 25° C. and 120° C., for 4 to 48 hours.

Compounds of formula (25) and (26) are commercially available or can easily be prepared using well-known procedures.

Alternatively, the amine of formula (2) may be prepared from the corresponding nitrile of formula (32):

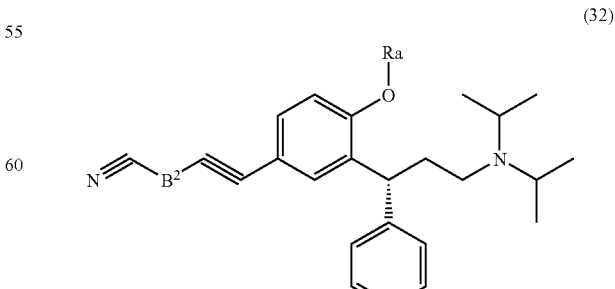

(32)

wherein B² is as defined above.

In a typical procedure, the nitrile of formula (32) is treated to hydrogenation using a metal catalyst or combination of catalysts (e.g palladium on carbon; platinum oxide, Raney-Nickel®) in the presence of a solvent (e.g. methanol, ethanol, ethyl acetate, tetrahydrofuran) with a hydrogen source (e.g. ammonium formate, formic acid, hydrogen) at a temperature comprised between 20° C. and 90° C., for 1 to 6 hours.

The nitrile of formula (32) may be prepared by reaction of the aryl bromide (13) with an alkyne of formula (33):

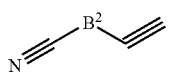
(33)

In a typical procedure, the aryl halide of formula (13) is reacted with the alkyne of formula (33) in the presence of a suitable palladium catalyst (e.g. palladium tetrakis(triphenylphosphine) or palladium acetate/tri-ortho-tolylphosphine of formula Pd(OAc)$_2$/{P(o-Tol)$_3$}$_2$) in the presence of a solvent or mixture of solvents (e.g. toluene, acetonitrile, hexane) in the presence of a base (e.g. triethylamine, piperidine, diisopropylethylamine, potassium carbonate, potassium hydrogen carbonate). Preferably, the reaction is carried out at a temperature comprising between 70° C. and 110° C. for 4 to 16 hours.

The alkyne of formula (33) may be commercial.

Alternatively, if alkyne (33) is of formula (34) as follows:

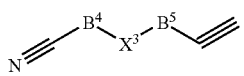
(34)

wherein X³ is O or S,

B⁴ is CH$_2$—(CH$_2$)$_m$ wherein m is an integer from 0 to 9 and B⁵ is (CH$_2$)$_{n1}$ wherein n$_1$ is an integer from 1 to 7, and n$_1$+m is comprised between 2 to 7 inclusive, or, B⁴ is a group of formula:

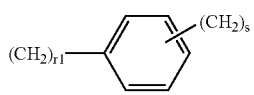

wherein r$_1$ is an integer from 1 to 6, s is an integer 0 to 6, and B⁶ is a group (CH$_2$)$_{t1}$ wherein to is an integer from 1 to 4, and s+t$_1$ is comprised between 1 to 4 inclusive and r$_1$+s+t$_1$ is comprised between 2 to 5 inclusive;

then said compound of formula (34) can be formed by reaction of a compound of formula (25):

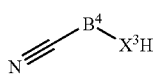
(25)

with a compound of formula (36):

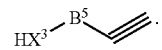
(36)

In a typical procedure, one of the compound (35) or (36) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the other compound (36) or (35) in the presence of a solvent or mixture of solvents (e.g. water, dimethyl sulphoxide, toluene, N,N-dimethylformamide, acetonitrile, tetrahydrofuran, dichloromethane) in the presence of a suitable base (e.g. sodium hydroxide, potassium tert-butoxide, sodium hydride) optionally in the presence of a phase transfer catalyst (e.g. tetra-ethylammonium bromide) at a temperature comprised between 25° C. and 120° C., for 4 to 48 hours.

The compounds of formula (35) and (36) are commercially available or are easily prepared according to well known processes.

The compounds of formula (1) wherein B is selected from (CH$_2$)$_2$—(CH$_2$)$_m$—X¹—(CH$_2$)$_n$ where n is 1 or a group of formula

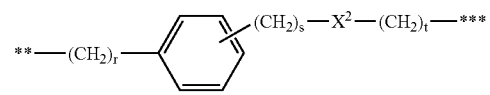

wherein t is 1, may be prepared by reaction of an amine of formula (27):

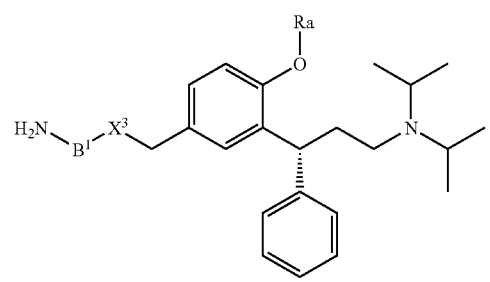
(27)

wherein X³, B¹ and Ra are as defined above, with a bromide of formula (3).

In a typical procedure, the amine of formula (27) is reacted with a bromide of formula (3) optionally in the presence of a solvent or mixture of solvents (e.g. dimethyl sulphoxide, toluene, N,N-dimethylformamide, propionitrile, acetonitrile), optionally in the presence of a suitable base (e.g. triethylamine, diisopropylethylamine, potassium carbonate, sodium hydrogen carbonate) at a temperature comprised between 80° C. and 120° C., for 12 to 48 hours. The protecting groups can then be removed using standard methodology for cleaving oxygen protecting groups such as those found in the text book T. W. Greene, Protective Groups in Organic Synthesis, A. Wiley-Interscience Publication, 1981.

The amine of formula (27) may be prepared from the corresponding protected amine of formula (28):

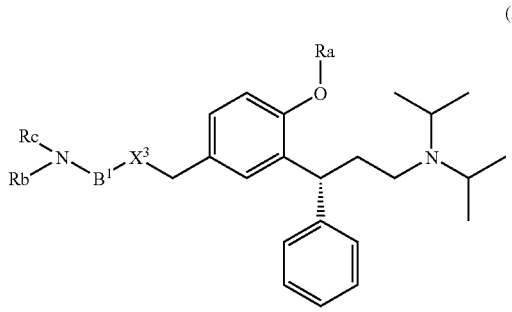
(28)

wherein Rb and Rc are as defined above.

The amine (28) may be prepared by reaction of alcohol (29):

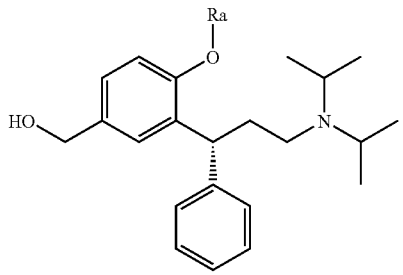
(29)

with a compound of formula (30):

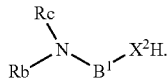
(30)

In a typical procedure, the alcohol of formula (29) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the compound of formula (30) in the presence of a solvent or mixture of solvents (e.g. water, dimethyl sulphoxide, toluene, N,N-dimethylformamide, acetonitrile, tetrahydrofuran, dichloromethane) in the presence of a suitable base (e.g. sodium hydroxide, potassium tert-butoxide, sodium hydride) optionally in the presence of a phase transfer catalyst (e.g. tetra-ethylammonium bromide) at a temperature comprised between 25° C. and 120° C., for 4 to 48 hours.

The alcohol of formula (29) may be prepared from the aldehyde of formula (7). In a typical procedure the aldehyde (7) is treated with a reductant (e.g. sodium borohydride; lithium aluminium hydride) in the presence of a solvent (e.g. tetrahydrofuran, methanol, toluene) at a temperature comprising between 0° C. and 40° C., for 1 to 24 hours.

The compound of formula (30) may be prepared from commercial alcohol of formula (31):

(31)

using the methods found in the textbook T. W. Greene, Protective Groups in Organic Synthesis, A. Wiley-Interscience Publication, 1981.

Finally, if the amine (4) is of the formula (38) as follows:

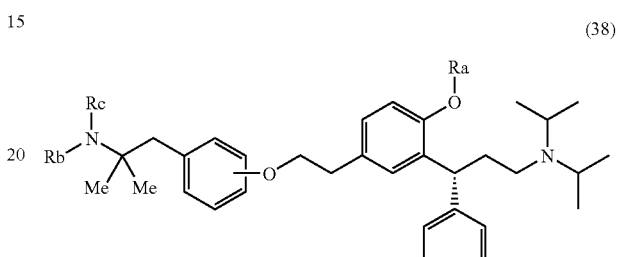
(38)

then it may be formed by reaction of a compound of formula (39):

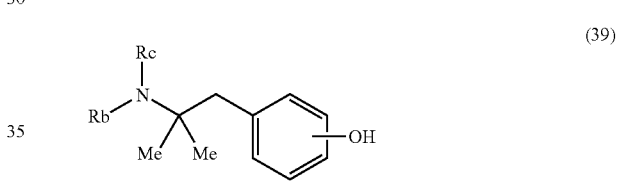
(39)

with a compound of formula (20):

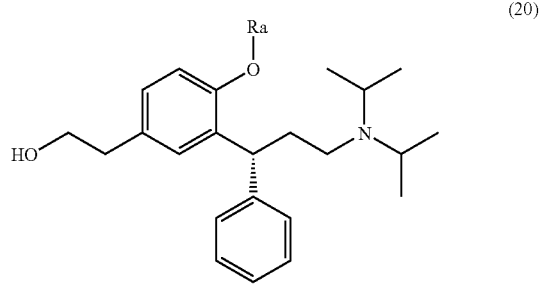
(20)

Above compounds of formula (39) may be prepared according to the methods described in WO97/34905.

In a typical procedure, the compound of formula (20) is first converted to a halide (e.g. bromide, chloride, iodide) or sulphonate (e.g. mesylate) using standard procedures (e.g. triphenylphospine/iodine; triphenylphosphine/carbon tetrabromide; thionyl chloride; methanesulphonyl chloride/triethylamine) in the presence of a solvent or mixture of solvents (e.g. dimethyl sulphoxide, dichloromethane, toluene, N,N-dimethylformamide, propionitrile, acetonitrile). This product is then reacted with the compound of formula (39) in the presence of a solvent or mixture of solvents (e.g. dimethyl sulphoxide, toluene, N,N-dimethylformamide, acetonitrile, tetrahydrofuran) optionally in the presence of a suitable base (e.g. triethylamine, diisopropylethylamine, potassium carbonate, potassium hydrogen carbonate) at a temperature comprised between 60° C. and 120° C., for 4 to 48 hours.

Alternatively, a Mitsunobu protocol may be employed (e.g. diethyl azodicarboxylate/triphenylphosphine) in the presence of a solvent or mixture of solvents (e.g. toluene, acetonitrile, tetrahydrofuran) at a temperature comprised between 25° C. and 60° C., for 2 to 4 hours.

The quaternary ammonium salts of compounds of the formula (1) include compounds of formula

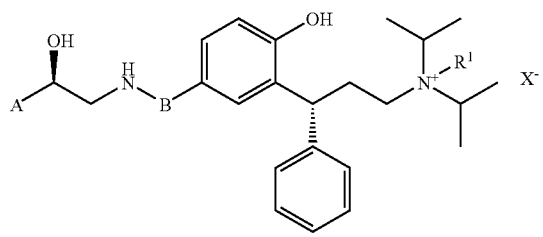

wherein $R^1$ is selected from H, $C_1$-$C_4$ alkyl, benzyl or phenethyl and X— is a suitable counter ion such as acetate, mesylate, xinafoate, tartrate, chloride, bromide, iodide, sulphate, phosphate(s), nitrate, citrate, methanesulfonate, carboxylate with from 1 to 6 carbon atoms, dicarboxylate with from 2 to 6 carbon atoms, maleate, fumarate and benzoate. For other acceptable quaternary ammonium salts, see Int. J. Pharm, 33, 201-217 (1986). Preferably X is acetate, fumarate, mesylate, bromide, chloride, sulphate, D and L tartrate or xinafoate. Said quaternary ammonium salts may be prepared by reacting a compound of formula (4) with an alkylating agent $R^1$—X wherein $R^1$ is a $C_1$-$C_4$ alkyl, benzyl or phenethyl and X is a suitable leaving group (a preferred $R^1$—X groups is methyl iodide) in the presence of a solvent or mixture of solvents (e.g. dimethyl sulphoxide, toluene, N,N-dimethylformamide, propionitrile, acetonitrile, dichloromethane) optionally in the presence of a suitable base (e.g. triethylamine, diisopropylethylamine, potassium carbonate, potassium hydrogen carbonate) at a temperature comprised between 60° C. and 120° C., for 4 to 48 hours. The resulting quaternary ammonium salt of compound of formula (4) is then deprotected and reacted with a bromide of formula (3) as disclosed above, in order to obtain said quaternary ammonium salt of compound of formula (1).

For some of the steps of the here above described process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

Preferred definitions of B are as indicated here below.

According to one embodiment, $(CH_2)_8$, $(CH_2)_9$ and $(CH_2)_{10}$ are preferred when B is a $C_6$-$C_{12}$ alkylene optionally substituted with one or two $C_1$-$C_4$ alkyl.

According to another embodiment —$(CH_2)_6$—O—$(CH_2)_3$, —$(CH_2)_6$—O—$(CH_2)_4$, and, —$(CH_2)_7$—O— are preferred when B is of formula —$(CH_2)_2$—$(CH_2)_m$—$X^1$—$(CH_2)_n$—*.

According to another embodiment, when B is of formula:

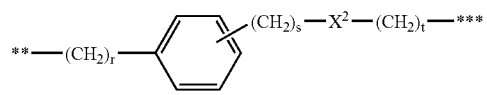

then the following are preferred:

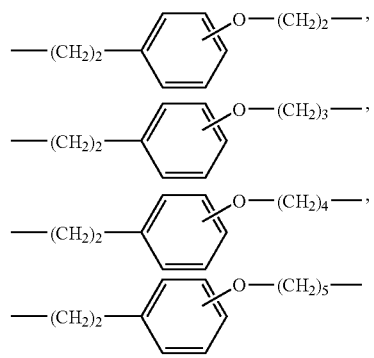

Preferably, the oxygen is in the meta or para position. More preferably the oxygen is in the para position.

According to another embodiment, when B is of formula:

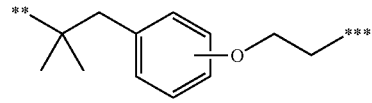

Then the oxygen in the para position is preferred.

Quaternary ammonium salts of compounds of formula (1) are also preferred. Preferred quaternary ammonium salts are:

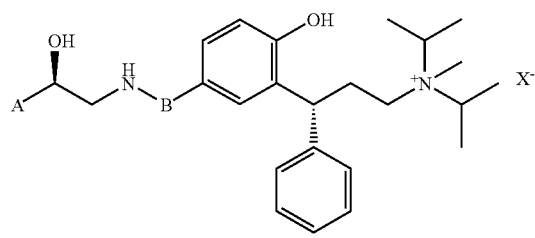

wherein X is acetate, fumarate, mesylate, bromide, chloride, sulphate, D and L tartrate or xinafoate.

According to another embodiment of the present invention, the quaternary ammonium salts of formula:

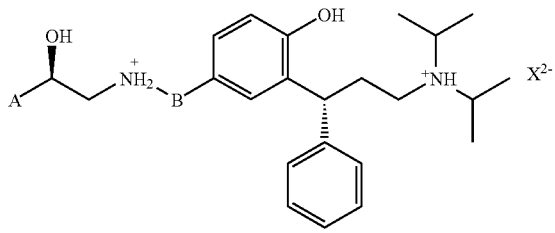

wherein X is succinate are also preferred.

Preferably A is a group of formula:

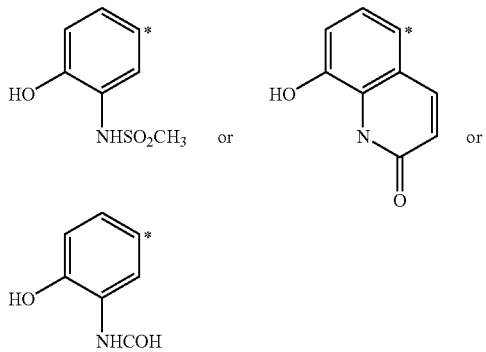

More preferably, A is a group of formula:

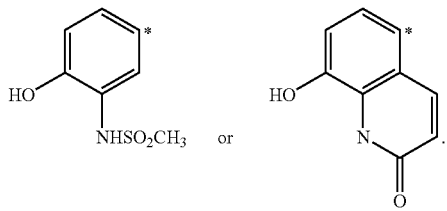

Particularly preferred compounds according to the invention are:

N-(5-{(1R)-2-[(10-{3-[(1R)-3-(diisopropylamino)-1-phenylpropyl]-4-hydroxyphenyl}decyl)amino]-1-hydroxyethyl}-2-hydroxyphenyl)methanesulfonamide;

N-{5-[(1R)-2-({2-[4-(3-{3-[(1R)-3-(diisopropylamino)-1-phenylpropyl]-4-hydroxyphenyl}propoxy)phenyl]ethyl}amino)-1-hydroxyethyl]-2-hydroxyphenyl}methane sulfonamide;

N-{5-[(1R)-2-({2-[4-(4-{3-[(1R)-3-(Diisopropylamino)-1-phenylpropyl]-4-hydroxyphenyl}butoxy)phenyl]ethyl}amino)-1-hydroxyethyl]-2-hydroxyphenyl}methanesulfonamide;

N-(5-{(1R)-2-[(7-{3-[(1R)-3-(diisopropylamino)-1-phenylpropyl]-4-hydroxyphenoxy}heptyl)amino]-1-hydroxyethyl}-2-hydroxyphenyl)methanesulfonamide;

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide;

N-{5-[(1R)-2-{[6-(4-{3-[(1R)-3-(Diisopropylamino)-1-phenylpropyl]-4-hydroxyphenyl}butoxy)hexyl]amino}-1-hydroxyethyl]-2-hydroxyphenyl}methanesulfonamide;

N-{5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-2-hydroxyphenyl}formamide;

5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-8-hydroxyquinolin-2(1H)-one;

5-[(1R)-1-{[hydroxy}-2-({2-[4-(4-{3-[(1R)-3-(diisopropylamino)-1-phenylpropyl]-4-hydroxyphenyl}butoxy)phenyl]ethyl}amino)ethyl]benzene-1,3-diol;

N-{5-[(1R)-2-({2-[3-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide;

2-[(1R)-3-(diisopropylamino)-1-phenylpropyl]-4-(2-{3-[2-({(2R)-2-hydroxy-2-[4-hydroxy-3-(hydroxymethyl)phenyl]ethyl}amino)ethyl]phenoxy}ethyl)phenol;

5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]benzene-1,3-diol;

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}formamide;

5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-8-hydroxyquinolin-2(1H)-one;

2-[(1R)-3-(diisopropylamino)-1-phenylpropyl]-4-(2-{4-[2-({(2R)-2-hydroxy-2-[4-hydroxy-3-(hydroxymethyl)phenyl]ethyl}amino)ethyl]phenoxy}ethyl)phenol;

N-(5-{(1R)-2-[(8-{3-[(1R)-3-(diisopropylamino)-1-phenylpropyl]-4-hydroxyphenyl}octyl)amino]-1-hydroxyethyl}-2-hydroxyphenyl)methanesulfonamide;

N-(5-{(1R)-2-[(2-{4-[(5-{3-[(1R)-3-(diisopropylamino)-1-phenylpropyl]-4-hydroxyphenyl}pentyl)oxy]phenyl}ethyl)amino]-1-hydroxyethyl}-2-hydroxyphenyl)methanesulfonamide;

2-[(1R)-3-(diisopropylamino)-1-phenylpropyl]-4-(4-{2-({(2R)-2-hydroxy-2-[4-hydroxy-3-(hydroxymethyl)phenyl]ethyl}amino)ethyl]phenoxy}butyl)phenol;

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide succinate salt; and 5-[(1R)-2-({2-[4-(2-{3-[(1R)-3-(diisopropylamino)-1-phenylpropyl]-4-hydroxyphenyl}ethoxy)phenyl]-11-dimethylethyl}amino)-1-hydroxyethyl]-8-hydroxyquinolin-2(1H)-one, or, if appropriate, their pharmaceutically acceptable salts and/or isomers, tautomers, solvates or isotopic variations thereof.

Most preferred compounds according to the invention are:

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide;

N-{5-[(1R)-2-{[6-(4-{3-[(1R)-3-(Diisopropylamino)-1-phenylpropyl]-4-hydroxyphenyl}butoxy)hexyl]amino}-1-hydroxyethyl]-2-hydroxyphenyl}methanesulfonamide;

5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-8-hydroxyquinolin-2(1H)-one;

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}formamide;

5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-8-hydroxyquinolin-2(1H)-one;

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide succinate salt; and 5-[(1R)-2-({2-[4-(2-{3-[(1R)-3-(diisopropylamino)-1-phenylpropyl]-4-hydroxyphenyl}ethoxy)phenyl]-11-dimethylethyl}amino)-1-hydroxyethyl]-8-hydroxyquinolin-2(1H)-one;

or, if appropriate, their pharmaceutically acceptable salts and/or isomers, tautomers, solvates or isotopic variations thereof.

Pharmaceutically acceptable salts of the compounds of formula (1) and quaternary ammonium salt thereof include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) and quaternary ammonium salt thereof may be prepared by one or more of three methods:

(i) by reacting the compound of formula (1) with the desired acid or base;

(ii) by removing an acid- or base-labile protecting group from a suitable precursor of the compound of formula (1) or by ring-opening a suitable cyclic precursor, for example, a lactone or lactam, using the desired acid or base; or (iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:

(i) where the compound of formula (1) contains a methyl group, an hydroxymethyl derivative thereof (—$CH_3$→—$CH_2OH$):

(ii) where the compound of formula (1) contains an alkoxy group, an hydroxy derivative thereof (—OR→—OH);

(iii) where the compound of formula (1) contains a tertiary amino group, a secondary amino derivative thereof (—$NR^1R^2$→—$NHR^1$ or —$NHR^2$);

(iv) where the compound of formula (1) contains a secondary amino group, a primary derivative thereof (—$NHR^1$→—$NH_2$);

(v) where the compound of formula (1) contains a phenyl moiety, a phenol derivative thereof (-Ph→-PhOH); and (vi) where the compound of formula (1) contains an amide group, a carboxylic acid derivative thereof (—$CONH_2$→COOH).

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include
(i) where the compound of formula (1) contains a secondary amino group, a primary derivative thereof (—NHR$^1$→—NH$_2$), and
(ii) where the compound of formula (1) contains a phenyl moiety, a phenol derivative thereof (-Ph→-PhOH).

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (1), for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. D$_2$O, d$_6$-acetone, d$_6$-DMSO.

The compounds of formula (1), their pharmaceutically acceptable salts and/or derived forms, are valuable pharmaceutically active compounds, which are suitable for the therapy and prophylaxis of numerous disorders in which agonism of the β2 receptor and antagonism of the muscarinic receptor may induce benefit, in particular the allergic and non-allergic airways diseases.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more P2 agonists, muscarinic antagonists or compounds active as beta 2 agonist and as muscarinic antagonist known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use.
(e) PDE inhibitors, e.g. PDE3, PDE4 and PDE5 inhibitors,
(f) Theophylline,
(g) Sodium cromoglycate,
(h) COX inhibitors both non-selective and selective COX-1 or COX-2 inhibitors (NSAIDs),
(i) Prostaglandin receptor antagonists and inhibitors of prostaglandin synthase.
(j) Oral and inhaled glucocorticosteroids,
(k) Dissociated agonists of the corticoid receptor (DAGR);
(l) Monoclonal antibodies active against endogenous inflammatory entities,
(m) Anti-tumor necrosis factor (anti-TNF-$\alpha$) agents,
(n) Adhesion molecule inhibitors including VLA-4 antagonists,
(o) Kinin-$B_1$- and $B_2$-receptor antagonists,
(p) Immunosuppressive agents, including inhibitors of the IgE pathway and cyclosporine,
(q) Inhibitors of matrix metalloproteases (MMPs),
(r) Tachykinin $NK_1$, $NK_2$ and $NK_3$ receptor antagonists,
(s) Protease inhibitors such as elastase inhibitors,
(t) Adenosine A2a receptor agonists and A2b antagonists,
(u) Inhibitors of urokinase,
(v) Compounds that act on dopamine receptors, such as D2 agonists,
(w) Modulators of the NFκβ pathway, such as IKK inhibitors,
(x) modulators of cytokine signalling pathways such as p38 MAP kinase, P13 kinase, JAK kinase, syk kinase, EGFR or MK-2,
(y) Agents that can be classed as mucolytics or anti-tussive,
(z) Agents, which enhance responses to inhaled corticosteroids.
(aa) Antibiotics and antiviral agents effective against microorganisms which can colonise the respiratory tract,
(bb) HDAC inhibitors,
(cc) CXCR2 antagonists,
(dd) Integrin antagonists,
(ee) Chemokines,
(ff) Epithelial sodium channel (ENaC) blockers or Epithelial sodium channel (ENaC) inhibitors,
(gg) P2Y2 Agonists and other Nucleotide receptor agonists,
(hh) Inhibitors of thromboxane,
(ii) Niacin, and
(jj) Adhesion factors including VLAM, ICAM, and ELAM.

According to the present invention, combination of the compounds of formula (1) with:
H3 antagonists,
PDE4 inhibitors,
Oral and inhaled glucocorticosteroids,
Dissociated agonists of the corticoid receptor (DAGR), Adenosine A2a receptor agonists, Modulators of cytokine signalling pathways such as p38, MAP kinase, P13 kinase, JAK kinase, syk kinase, EGFR or MK-2, or Leukotriene antagonists (LTRAs) including antagonists of LTB$_4$, LTC$_4$, LTD$_4$, and LTE$_4$, are preferred.

According to the present invention, combination of the compounds of formula (1) with glucocorticosteroids, including prednisone, prednisolone, flunisolide, triamcinolone acetonide, beclomethasone dipropionate, budesonide, fluticasone propionate, ciclesonide, mometasone furoate and mometasone furoate monohydrate and in particular inhaled glucocorticosteroids with reduced systemic side effects, are further preferred.

It is to be appreciated that all references herein to treatment include curative, palliative and prophylactic treatment.

The compounds of formula (1) have the ability to interact with the β2 receptor and cholinergic muscarinic receptors, and thereby have a wide range of therapeutic applications, as described further below, because of the essential role which the β2 receptor and muscarinic receptors play in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the β2 receptor and/or muscarinic receptors are involved. More specifically, the present invention also concerns the compounds of formula (1), or pharmaceutically acceptable salts, derived forms or compositions thereof, for use in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity and an M3 antagonist activity. In particular, the present inventions concerns the use of the compounds of formula (1), or pharmaceutically acceptable salts, derived forms or compositions thereof, for the manufacture of a drug for the treatment of diseases and/or conditions involving the beta 2 and M3 receptors, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions involving the beta 2 and M3 receptors, in a mammal, including a human being, in particular the diseases and/or conditions listed above, comprising administering said mammal with an effective amount of a compound of formula (1), its pharmaceutically acceptable salts and/or derived forms.

The following examples illustrate the preparation of the compounds of the formula (1):

Preparation 1

Di-tert-butyl(9-bromononyl)imidocarbonate

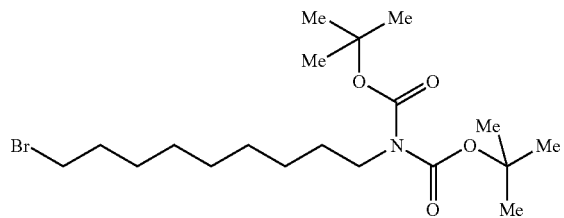

Sodium hydride (1.31 g of a 60% dispersion in oil, 30.0 mmol) was added in one portion to a stirred solution of di-tert-butyl iminodicarbamate (6.50 g, 30.0 mmol) in N,N-dimethylformamide (5 ml) at 0° C. under nitrogen. The reaction was stirred for 5 minutes at 0° C. and then stirred at room temperature for 30 minutes. The reaction was cooled to 0° C. and 1,9-dibromononane (8.60 g, 30.0 mmol) added dropwise, the reaction was allowed to warm to room temperature and stirred for 3 days. Diethyl ether (50 ml) and water (20 ml) were cautiously added and the organics separated, the aqueous layer was washed with diethyl ether (50 ml) and the combined organics dried (magnesium sulphate) and the solvent removed in vacuo to yield a clear oil. The oil was purified by column chromatography on silica gel eluting with diethyl ether:hexane (10/90 by volume) to furnish the title compound as a colourless oil, 5.80 g.

$^1$H NMR (400 MHz, CD$_3$OD): δ=1.30 (10H, m), 1.50 (20H, m), 1.83 (2H, m), 3.42 (2H, t), 3.58 (2H, t) ppm.

Preparation 2

Di-tert-butyl[10-{4-(benzyloxy)-3-[(1R)-3-(diisopropylamino)-1-phenylpropyl]phenyl}dec-9-en-1-yl] imidodicarbonate

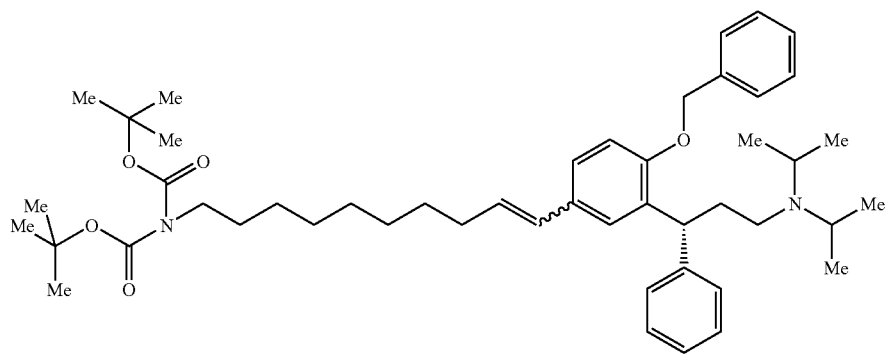

Di-tert-butyl(9-bromononyl)imidocarbonate (Preparation 1, 1.80 g, 4.26 mmol) and triphenylphosphine (2.00 g, 7.63 mmol) were dissolved in acetonitrile (40 ml) and heated under reflux for 48 hours. The reaction was cooled to room temperature and the solvent reduced in vacuo to 8 ml. The reaction was heated under reflux for 12 hours and the reaction cooled to room temperature. The solvent was removed in vacuo to furnish the intermediate phosphonium salt as a gum. The gum (1.70 g, 2.48 mmol) was dissolved in tetrahydrofuran (15 ml) and cooled to −78° C. under a nitrogen atmosphere. n-Butyl lithium (0.90 ml of a 2.5M solution in hexanes, 2.25 mmol) was added dropwise to give an orange solution which was then warmed to 0° C. and stirred for 45 minutes. The reaction was cooled to −78° C. and a solution of 4-(benzyloxy)-3-[(1R)-3-(diisopropylamino)-1-phenylpropyl]benzaldehyde (Prepared according to WO 2005/012227, 320 mg, 0.75 mmol) in tetrahydrofuran (5 ml) was added dropwise and the reaction stirred at −78° C. for 10 minutes. The reaction was warmed to room temperature and stirred for 12 hours and then poured onto ethyl acetate (30 ml) and water (20 ml). The organics were separated, dried (magnesium sulphate) and the solvent removed in vacuo, the residue was purified by column chromatography on silica gel eluting with dichloromethane:methanol:880 ammonia (90/10/1.0 by volume) to furnish the title compound as a white gum, 140 mg.

LRMS: m/z 755.7 [M+H]$^+$.

Preparation 3

10-{4-(Benzyloxy)-3-[(1R)-3-(diisopropylamino)-1-phenylpropyl]phenyl}dec-9-en-1-amine

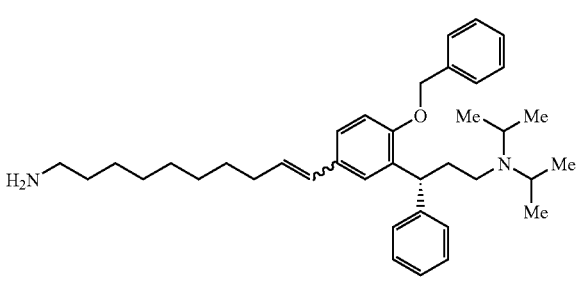

Hydrochloric acid (10.0 ml of a 2M solution in diethyl ether) was added in one portion to a stirred solution of di-tert-butyl[10-{4-(benzyloxy)-3-[(1R)-3-(diisopropylamino)-1-phenylpropyl]phenyl}dec-9-en-1-yl]imidodicarbonate (Preparation 2, 450 mg, 0.59 mmol) at room temperature in dichloromethane (5 ml) under a nitrogen atmosphere. The reaction was stirred for 2 hours and the solvent removed in vacuo, the residue was dissolved in ethyl acetate (30 ml) and saturated aqueous sodium hydrogen carbonate (20 ml). The organics were separated, washed with water (10 ml), dried (magnesium sulphate) and the solvent removed in vacuo. The residue was purified by column chromatography on silica gel eluting with dichloromethane:methanol:880 ammonia (90/10/1.0 by volume) to furnish the title compound as a glass, 180 mg.

LRMS: m/z 556 [M+H]$^+$.

Preparation 4

N-{2-(benzyloxy)-5-[(1R)-2-{[10-{4-(benzyloxy)-3-[(1R)-3-(diisopropylamino)-1-phenylpropyl]phenyl}dec-9-en-1-yl]amino}-1-{[tert-butyl(dimethyl)silyl]oxy}ethyl]phenyl}methanesulfonamide

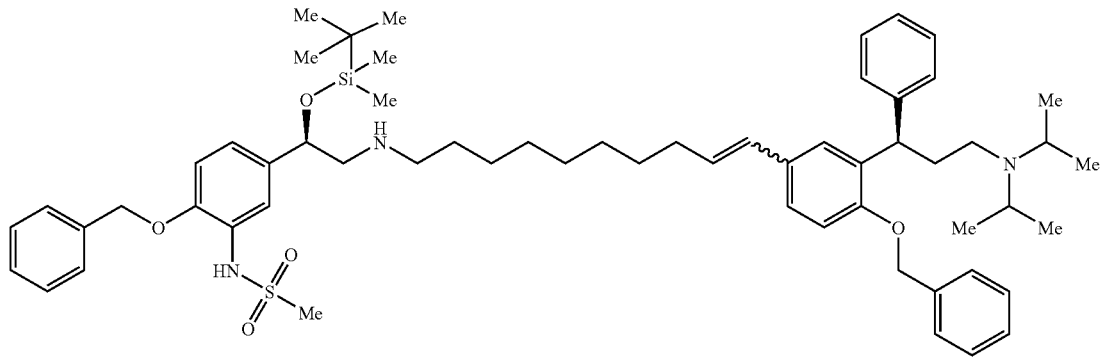
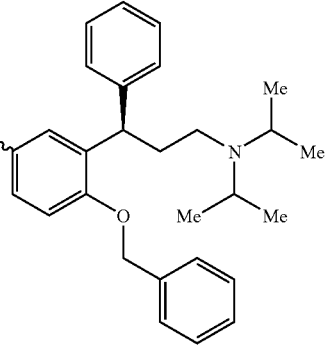

10-{4-(Benzyloxy)-3-[(1R)-3-(diisopropylamino)-1-phenylpropyl]phenyl}dec-9-en-1-amine (Preparation 3, 170 mg, 0.33 mmol) and N-{2-(benzyloxy)-5-[(1R)-2-bromo-1-{[tert-butyl(dimethyl)silyl]oxy}ethyl]phenyl}methanesulfonamide (Prepared according to WO2005/080324, 180 mg, 0.33 mmol) were heated at 90° C. in dimethylsulfoxide (0.5 ml) for 12 hours. Ethyl acetate (20 ml) and water (10 ml) were added and the organics separated, washed with water (10 ml), dried (magnesium sulphate) and the solvent removed in vacuo. The residue was purified by column chromatography on silica gel eluting with dichloromethane:methanol:880 ammonia (80/20/2.0 by volume) to furnish the title compound as a glass, 90 mg.

LRMS: m/z 989 [M+H]$^+$.

Allyl bromide (2.10 ml, 24.8 mmol) was added in one portion to a suspension of potassium carbonate (4.40 g, 31.8 mmol) and tert-butyl[2-(4-hydroxyphenyl)ethyl]carbamate (Prepared according to Journal of Organic Chemistry 1999, 64, 1074, 5.00 g, 21.1 mmol) in acetonitrile (50 ml) at room temperature. The reaction was stirred for 12 hours and the solvent removed in vacuo. Diethyl ether (50 ml) and water (20 ml) were added and the organics separated, washed with water (20 ml), dried (magnesium sulphate) and the solvent removed in vacuo to yield a clear oil. The oil was purified by column chromatography on silica gel eluting with ethyl acetate:pentane (25/75 by volume) to furnish the title compound as a white solid, 3.80 g.

$^1$H NMR (400 MHz, CDCl$_3$): δ=1.42 (9H, s), 2.78 (2H, m), 3.37 (2H, m), 4.58 (3H, m), 5.28 (1H, dd), 5.40 (1H, dd), 6.10 (1H, m), 6.84 (2H, d), 7.10 (2H, d) ppm.

Preparation 5 tert-Butyl{2-[4-(allyloxy)phenyl]ethyl}carbamate

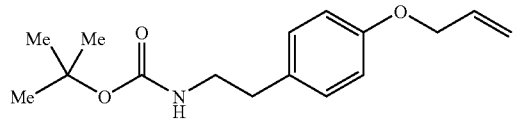

Preparation 6 tert-Butyl[2-(4-{[(2E)-3-{4-(benzyloxy)-3-[(1R)-3-(diisopropylamino)-1-phenylpropyl]phenyl}prop-2-en-1-yl]oxy}phenyl)ethyl]carbamate

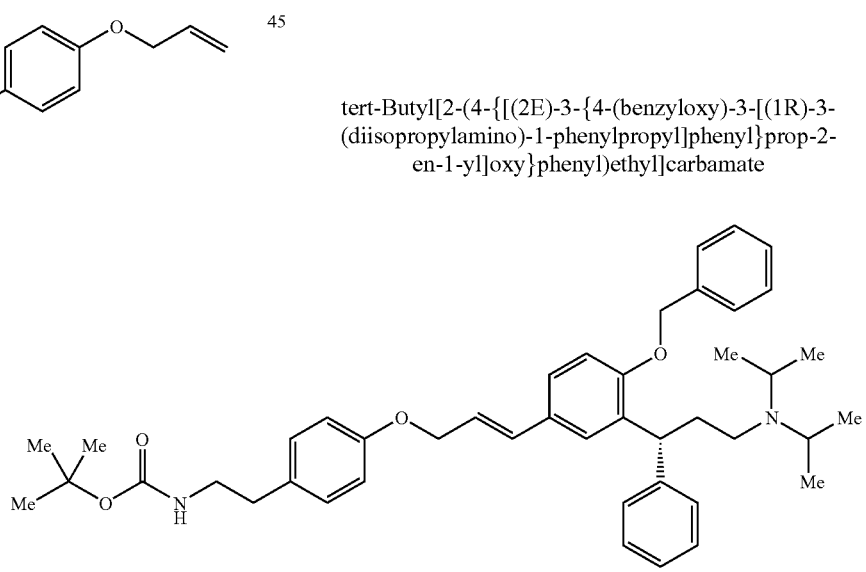

(3R)-3-[2-(benzyloxy)-5-bromophenyl]-N,N-diisopropyl-3-phenylpropan-1-amine (Prepared according to WO1994/11337, 800 mg, 1.66 mmol), tert-Butyl{2-[4-(allyloxy)phenyl]ethyl}carbamate (Preparation 5, 924 mg, 3.33 mmol), palladium acetate (37 mg, 0.16 mmol), tri(o-tolyl) phosphine (101 mg, 0.33 mmol), and diisopropylethylamine (435 ul, 2.50 mmol) were heated at 90° C. in acetonitrile (10 ml) under a nitrogen atmosphere for 12 hours. The reaction was cooled to room temperature and poured onto ethyl acetate (30 ml) and water (20 ml). The organics were separated, washed with saturated aqueous sodium hydrogen carbonate (20 ml), water (20 ml), brine (20 ml), dried (magnesium sulphate) and the solvent removed in vacuo, the residue was purified by column chromatography on silica gel eluting with dichloromethane:methanol:880 ammonia (90/10/1.0 by volume) to furnish the title compound as a glass, 475 mg.
LRMS: m/z 677 [M+H]+.

Preparation 7 tert-Butyl{2-[4-(3-{3-[(1R)-3-(diisopropylamino)-1-phenylpropyl]-4-hydroxyphenyl}propoxy)phenyl]ethyl}carbamate tert-Butyl[2-(4-{[(2E)-3-{4-(benzyloxy)-3-[(1R)-3-(diisopropylamino)-1-phenylpropyl]phenyl}prop-2-en-1-yl]oxy}phenyl)ethyl]carbamate (Preparation 6, 475 mg, 0.70 mmol) was dissolved in ethanol (20 ml) and 10% palladium on carbon (50 mg) added. The reaction was heated to 40° C. under 50 psi of hydrogen for 4 hours. The reaction was cooled to room temperature and filtered through Arbocel™, the filtrate was collected and the solvent removed in vacuo to furnish the title compound as a glass, 400 mg.
LRMS: m/z 589 [M+H]+.

Preparation 8

4-{3-[4-(2-aminoethyl)phenoxy]propyl}-2-[(1R)-3-(diisopropylamino)-1-phenylpropyl]phenol

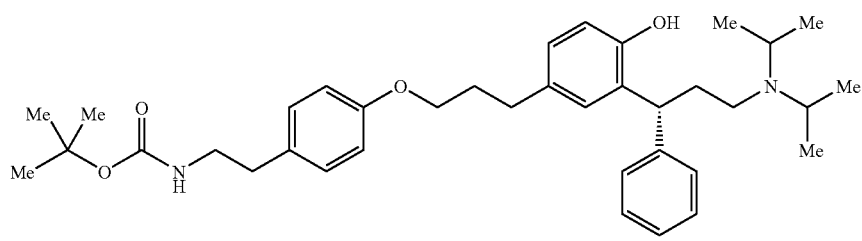

tert-Butyl{2-[4-(3-{3-[(1R)-3-(diisopropylamino)-1-phenylpropyl]-4-hydroxyphenyl}propoxy)phenyl]ethyl}carbamate (Preparation 7, 400 mg, 0.68 mmol) was dissolved in dichloromethane (15 ml) and hydrochloric acid (10 ml of a 2M solution in diethyl ether) was added to the stirred solution at 0° C. After 3 hours the solvent was removed in vacuo, and ethyl acetate (20 ml) and saturated aqueous sodium hydrogen carbonate (10 ml) were added and the organics separated. The aqueous was washed with dichloromethane:methanol (90:10, by volume, 2×20 ml) and the organics combined, dried (magnesium sulphate) and the solvent removed in vacuo. The residue was purified by column chromatography on silica gel eluting with dichloromethane:methanol:880 ammonia (80/20/2.0 by volume) to furnish the title compound as a glass, 135 mg.
LRMS: m/z 489 [M+H]+.

Preparation 9

N-{2-(benzyloxy)-5-[(1R)-1-{[tert-butyl(dimethyl)silyl]oxy}-2-({2-[4-(3-{3-[(1R)-3-(diisopropylamino)-1-phenylpropyl]-4-hydroxyphenyl}propoxy)phenyl]ethyl}amino)ethyl]phenyl}methanesulfonamide

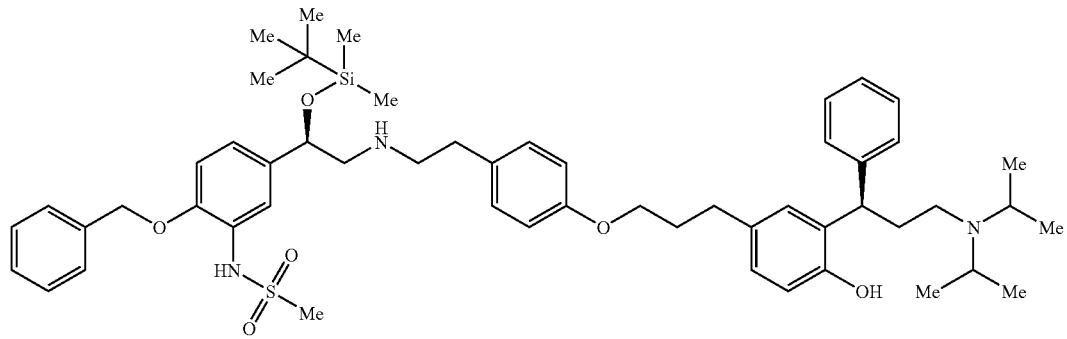

4-{3-[4-(2-aminoethyl)phenoxy]propyl}-2-[(1R)-3-(diisopropylamino)-1-phenylpropyl]phenol (Preparation 8, 134 mg, 0.27 mmol) and N-{2-(benzyloxy)-5-[(1R)-2-bromo-1-{[tert-butyl(dimethyl)silyl]oxy}ethyl]phenyl}methanesulfonamide (Prepared according to WO2005/080324, 145 mg, 0.28 mmol) were heated at 90° C. in dimethylsulfoxide (0.5 ml) for 24 hours. Ethyl acetate (20 ml) and water (10 ml) were added and the organics separated. The aqueous was washed with ethyl acetate (20 ml) and the combined organics washed with brine (10 ml), dried (magnesium sulphate) and the solvent removed in vacuo. The residue was purified by column chromatography on silica gel eluting with dichloromethane:methanol:880 ammonia (80/20/2.0 by volume) to furnish the title compound as a glass, 101 mg.

LRMS: m/z 923 [M+H]$^+$.

Preparation 10

N-{5-[(1R)-1-{[tert-butyl(dimethyl)silyl]oxy}-2-({2-[4-(3-{3-[(1R)-3-(diisopropylamino)-1-phenylpropyl]-4-hydroxyphenyl}propoxy)phenyl]ethyl}amino)ethyl]-2-hydroxyphenyl}methanesulfonamide

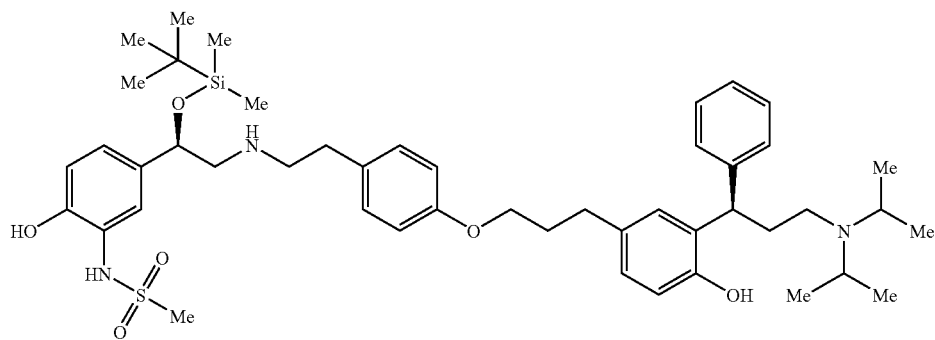

N-{2-(benzyloxy)-5-[(1R)-1-{[tert-butyl(dimethyl)silyl]oxy}-2-({2-[4-(3-{3-[(1R)-3-(diisopropylamino)-1-phenylpropyl]-4-hydroxyphenyl}propoxy)phenyl]ethyl}amino)ethyl]phenyl}methanesulfonamide (Preparation 9, 100 mg, 0.11 mmol) was dissolved in ethanol (10 ml) and ammonium formate (68 mg, 1.07 mmol) and 10% palladium hydroxide on carbon (20 mg) added. The stirred reaction was heated at 90° C. for 2 hours, cooled to room temperature and filtered through Arbocel™, the filtrate was collected and the solvent removed in vacuo to furnish the title compound as a yellow glass, 98 mg.

LRMS: m/z 833 [M+H]$^+$.

Preparation 11 tert-Butyl[2-(4-{[(3E)-4-{4-(benzyloxy)-3-[(1R)-3-(diisopropylamino)-1-phenylpropyl]phenyl}but-3-en-1-yl]oxy}phenyl)ethyl]carbamate

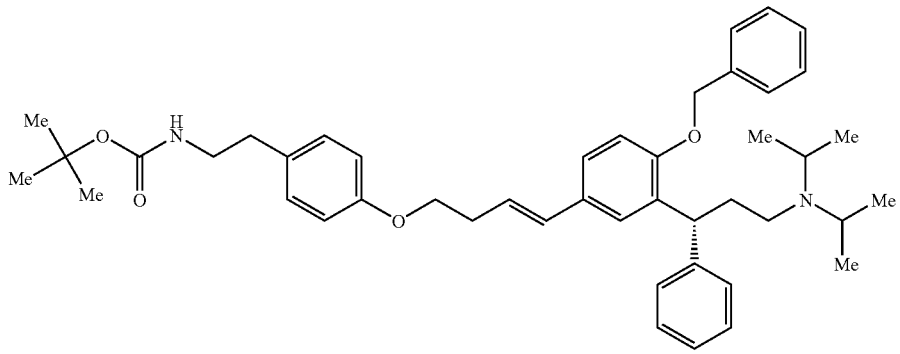

tert-butyl[2-(4-hydroxyphenyl)ethyl]carbamate (Prepared according to Journal of Organic Chemistry 1999, 64, 1074, 1g, 4.2 mmol) was dissolved in dimethylformamide (8 ml) and potassium carbonate (698 mg, 5.1 mmol) was added, followed by 4-bromobut-1-ene (0.51 ml, 5.1 mmol) and the mixture was heated to 60° C. After 5 hours cooled to room temperature, then a further portion of potassium carbonate (698 mg, 5.1 mmol) and 4-bromobut-1-ene (0.51 ml, 5.1 mmol) were added and the mixture reheated to 60° C. After 18 hours cooled to room temperature, then a further portion of potassium carbonate (698 mg, 5.1 mmol) and 4-bromobut-1-ene (0.51 ml, 5.1 mmol) were added and the mixture reheated to 60° C. After a further 5 hours cooled to room temperature, then a further portion of potassium carbonate (350 mg, 2.5 mmol) and 4-bromobut-1-ene (0.25 ml, 2.5 mmol) were added and the mixture reheated to 60° C. Left to stir over night then cooled to room temperature, water added and extracted with ethyl acetate, dried (magnesium sulphate) and the solvent removed in vacuo, the residue was purified by column chromatography on silica gel eluting with pentane/ethyl acetate (80/20 by volume). The above reaction was repeated to yield 1.1 g of intermediate, which was dissolved in acetonitrile (10 ml), (3R)-3-[2-(benzyloxy)-5-bromophenyl]-N,N-diisopropyl-3-phenylpropan-1-amine (Prepared according to WO9411337, 1.2 g, 2.5 mmol), tris(2-methylphenyl)phosphine (760 mg, 2.5 mmol) and diisopropyl ethylamine (0.87 ml, 4.99 mmol) were added and the mixture degassed with a stream of argon gas. Palladium diacetate (280 mg, 1.25 mmol) was added and the mixture was heated to 90° C. After 5 hours, cooled to room temperature and left to stir over night. The mixture was filtered through Arbocel™ and the solvent removed in vacuo. Water was added and extracted with ethyl acetate the organic layer separated and dried (magnesium sulphate) and the solvent removed in vacuo, the residue was purified by column chromatography on silica gel eluting with dichloromethane:methanol:880 ammonia (98/2/0.2 to 96/4/0.4 by volume) to yield the title compound as a colourless gum, 1.45 g.

LRMS: m/z 691 [M+H]$^+$.

Preparation 12 tert-Butyl{2-[4-(4-{3-[(1R)-3-(diisopropylamino)-1-phenylpropyl]-4-hydroxyphenyl}butoxy)phenyl]ethyl}carbamate

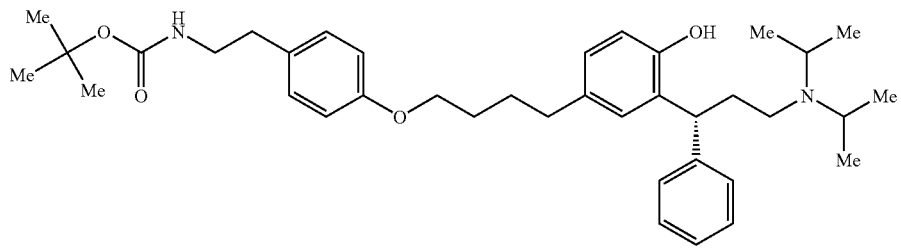

tert-butyl[2-(4-{[(3E)-4-{4-(benzyloxy)-3-[(1R)-3-(diisopropylamino)-1-phenylpropyl]phenyl}but-3-en-1-yl]oxy}phenyl)ethyl]carbamate (Preparation 11, 725 mg, 1.05 mmol) was dissolved in ethanol (10 ml), palladium hydroxide (20% by weight on carbon, 181 mg, 0.25 mmol) then ammonium formate (529 mg, 8.39 mmol) was added and heated to 80° C. for 5 minutes then stirred at 75° C. for 1 hour. Reaction was cooled to room temperature and the mixture was filtered through Arbocel™ and the solvent removed in vacuo. The residue was purified by column chromatography on silica gel eluting with dichloromethane:methanol:880 ammonia (97/3/0.3 to 94/6/0.6 by volume) to yield the title compound as a white foam, 460 mg.

LRMS: m/z 603 [M+H]$^+$.

Preparation 13

4-{4-[4-(2-Aminoethyl)phenoxy]butyl}-2-[(1R)-3-(diisopropylamino)-1-phenylpropyl]phenol bis hydrochloride salt

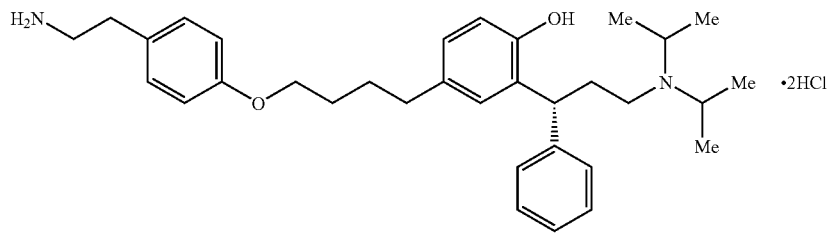

tert-butyl{2-[4-(4-{3-[(1R)-3-(diisopropylamino)-1-phenylpropyl]-4-hydroxyphenyl}butoxy)phenyl]ethyl}carbamate (Preparation 12, 450 mg, 0.75 mmol) was dissolved in dichloromethane (10 ml), hydrogen chloride (2M in diethyl ether, 6 ml, 12 mmol) was added followed by ethanol (1 ml). After 3 days, solvents removed in vacuo to furnish the title compound as a yellow foam, 420 mg.

LRMS: m/z 503 [M(free base)+H]$^+$.

Preparation 14

N-{2-(Benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]phenyl}methanesulfonamide

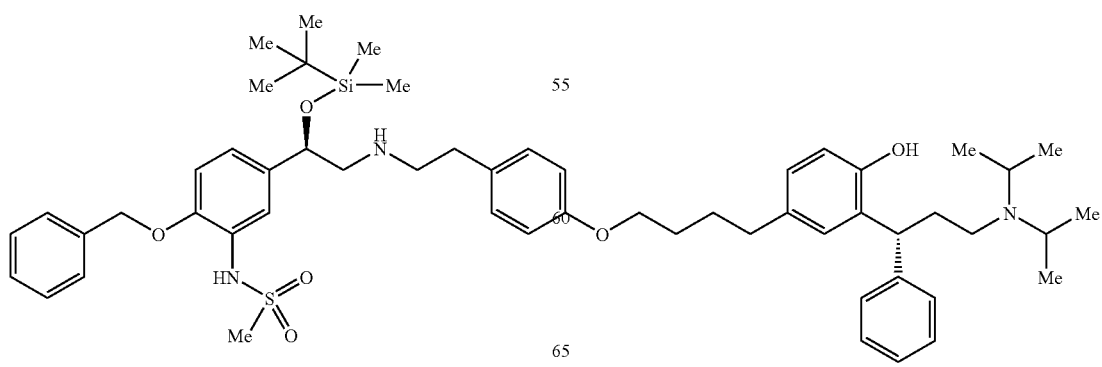

4-{4-[4-(2-aminoethyl)phenoxy]butyl}-2-[(1R)-3-(diisopropylamino)-1-phenylpropyl]phenol bis hydrochloride salt (Preparation 13, 420 mg, 0.73 mmol), N-{2-(benzyloxy)-5-[(1R)-2-bromo-1-{[tert-butyl(dimethyl)silyl]oxy}ethyl]phenyl}methanesulfonamide (Prepared according to WO2005/080324, 375 mg, 0.73 mmol), sodium hydrogen carbonate (245 mg, 2.92 mmol) and potassium iodide (121 mg, 0.73 mmol) were added to acetonitrile (15 ml) and heated to 90° C. for 30 minutes and left at room temperature for 48 hours, water was added and extracted with ethyl acetate, dried (magnesium sulphate) and the solvent removed in vacuo, the residue was purified by column chromatography on silica gel eluting with dichloromethane:methanol:880 ammonia (971310.3 to 92/810.8 by volume) to furnish the title compound as a white foam, 207 mg.

LRMS: m/z 937 [M+H]$^+$.

Preparation 15

N-{5-[(1R)-1-{[tert-Butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-hydroxyphenyl}methanesulfonamide Preparation 16

4-(Benzyloxy)-3-[(1R)-3-(diisopropylamino)-1-phenylpropyl]phenol

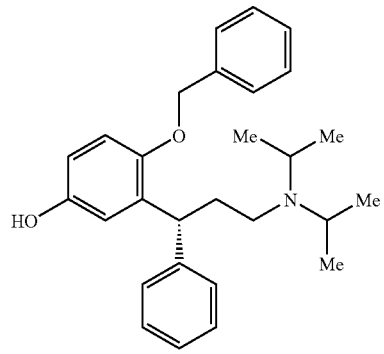

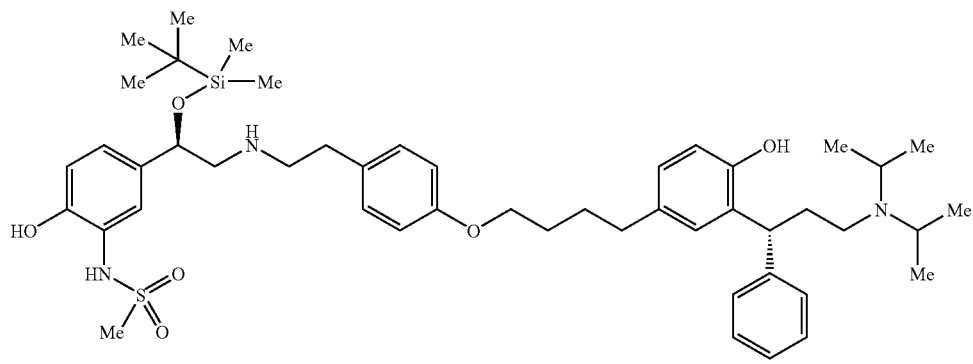

N-{2-(benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]phenyl}methanesulfonamide (Preparation 14, 200 mg, 0.2 mmol), and palladium hydroxide (20% by weight on carbon, 50 mg, 0.07 mmol) were dissolved in ethanol (5 ml), then ammonium formate (74 mg, 1.2 mmol) was added and heated to 80° C. for 5 minutes then stirred at 75° C. for 1 hour. Reaction was cooled to room temperature and the mixture was filtered through Arbocel™ and the solvent removed in vacuo. to yield the title compound as a white foam, 190 mg.

LRMS: m/z 847 [M+H]$^+$.

4-(benzyloxy)-3-[(1R)-3-(diisopropylamino)-1-phenylpropyl]benzaldehyde (Prepared according to WO2005012227, 1g, 2.32 mmol) was dissolved in methanol (40 ml), sulphuric acid (2M, 6 ml) then hydrogen peroxide (30% by weight in water, 2 ml) was added, and the reaction mixture was allowed to stir over night. The mixture was partitioned between water and diethyl ether, the organic layer was separated, washed with saturated sodium sulfite solution, dried (magnesium sulphate), filtered and the solvent removed in vacuo and the residue was purified by column chromatography on silica gel eluting with dichloromethane:methanol:880 ammonia (24/1/0.1 to 23/210.2 by volume) to furnish the title compound as a buff foam, 560 mg.

LRMS: m/z 418 [M+H]$^+$.

Preparation 17

Di-tert-butyl(7-{4-(benzyloxy)-3-[(1R)-3-(diisopropylamino)-1-phenylpropyl]phenoxy}heptyl)imidodicarbonate

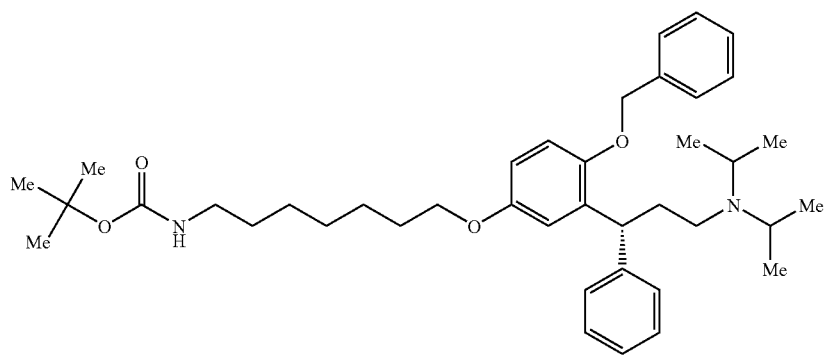

4-(Benzyloxy)-3-[(1R)-3-(diisopropylamino)-1-phenylpropyl]phenol (Preparation 16, 150 mg, 0.36 mmol) was dissolved in dimethylformamide (2 ml), caesium carbonate (140 mg, 0.43 mmol) was added and stirred at room temperature for 30 minutes. tert-Butyl(7-bromoheptyl)carbamate (Prepared according to J. Med. Chem., 1994, 137, p2537-2551; 170 mg, 0.43 mmol), dissolved in dimethylformamide (1 ml), was added and heated to 70oC. After 2.5 hours caesium carbonate (70 mg, 0.22 mmol) was added and after a further 10 minutes tert-butyl(7-bromoheptyl)carbamate (70 mg, 0.18 mmol) was added. After 1 hour caesium carbonate (20 mg, 0.06 mmol) and tert-butyl(7-bromoheptyl)carbamate (35 mg, 0.09 mmol) were added and after 1 hour at 70° C. the mixture was cooled to room temperature and stirred for 3 days before the addition of water and brine were added, the mixture extracted with ethyl acetate, dried (magnesium sulphate), filtered and the solvents removed in vacuo and the residue was purified by column chromatography on silica gel eluting with dichloromethane:methanol:880 ammonia (98/2/0.2 to 95/5/0.5 by volume) to furnish the title compound as a colourless gum, 220 mg.

LRMS: m/z 731 [M+H]$^+$.

Preparation 18

7-{4-(benzyloxy)-3-[(1R)-3-(diisopropylamino)-1-phenylpropyl]phenoxy}heptan-1-amine bis hydrochloride salt

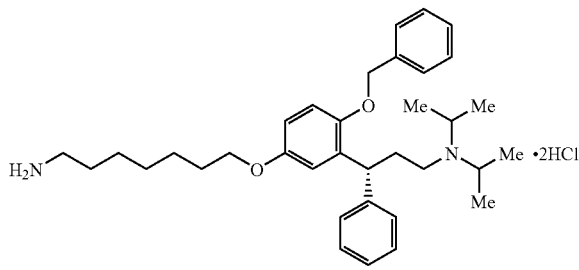

Di-tert-butyl(7-{4-(benzyloxy)-3-[(1R)-3-(diisopropylamino)-1-phenylpropyl]phenoxy}heptyl)imidodicarbonate (Preparation 17, 220 mg, 0.30 mmol) was dissolved in dichloromethane (6 ml) then hydrogen chloride (2M solution in diethyl ether, 6 ml, 12 mmol) was added and after 30 minutes, ethanol (1 ml) was added and left over night. The solvent was removed in vacuo to furnish the title compound as a pale brown foam, 190 mg.

LRMS: m/z 531 [M(free base)+H]$^+$.

Preparation 19

N-{2-(Benzyloxy)-5-[(1R)-2-[(7-{4-(benzyloxy)-3-[(1R)-3-(diisopropylamino)-1-phenylpropyl]phenoxy}heptyl)amino]-1-{[tert-butyl(dimethyl)silyl]oxy}ethyl]phenyl}methanesulfonamide

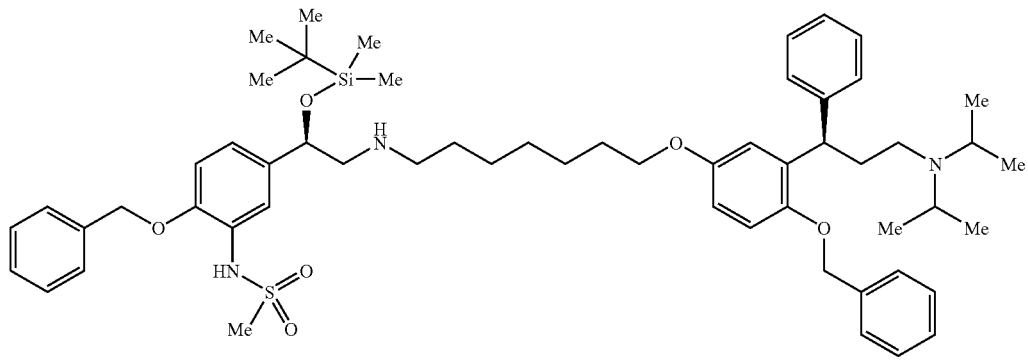

7-{4-(benzyloxy)-3-[(1R)-3-(diisopropylamino)-1-phenylpropyl]phenoxy}heptan-1-amine bis hydrochloride salt (Preparation 18, 190 mg, 0.31 mmol), N-{2-(benzyloxy)-5-[(1R)-2-bromo-1-{[tert-butyl(dimethyl)silyl]oxy}ethyl]phenyl}methanesulfonamide (Prepared according to WO2005/080324, 161 mg, 0.32 mmol), sodium hydrogen carbonate (106 mg, 1.26 mmol) and potassium iodide (52 mg, 0.32 mmol) were added to acetonitrile (5 ml) and heated to 90° C. for 24 hours, then left at room temperature over night, water and brine were added and extracted with ethyl acetate, dried (magnesium sulphate) and the solvent removed in vacuo, the residue was purified by column chromatography on silica gel eluting with dichloromethane:methanol:880 ammonia (98/2/0.2 to 92/8/0.8 by volume) to furnish the title compound as a colourless gum, 100 mg.

LRMS: m/z 965 [M+H]$^+$.

Preparation 20

N-(5-{(1R)-1-{[tert-butyl(dimethyl)silyl]oxy}-2-[(7-{3-[(1R)-3-(diisopropylamino)-1-phenylpropyl]-4-hydroxyphenoxy}heptyl)amino]ethyl}-2-hydroxyphenyl)methanesulfonamide

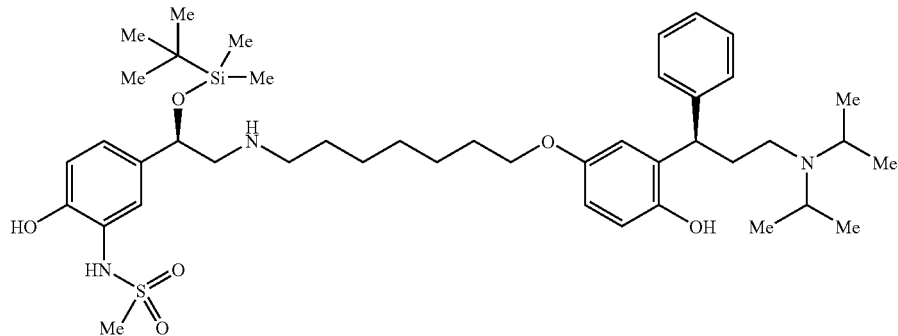

N-{2-(Benzyloxy)-5-[(1R)-2-[(7-{4-(benzyloxy)-3-[(1R)-3-(diisopropylamino)-1-phenylpropyl]phenoxy}heptyl)amino]-1-{[tert-butyl(dimethyl)silyl]oxy}ethyl]phenyl}methanesulfonamide (Preparation 19, 96 mg, 0.10 mmol) and palladium hydroxide (20% by weight on carbon, 25 mg, 0.04 mmol) were dissolved in ethanol (3 ml), then ammonium formate (69 mg, 1.1 mmol) was added and heated to 80° C. for 1 hour. The reaction was cooled to room temperature and the mixture was filtered through Arbocel™ and the solvent removed in vacuo. The residue was dissolved in dichloromethane (containing a trace of methanol) and washed with water (brine was added to aid in the separation), the organic layer was dried (magnesium sulphate), filtered, and the solvents removed in vacuo to yield the title compound as a white foam, 68 mg.

LRMS: m/z 785 [M+H]$^+$.

mmol) was then added and the reaction was stirred over night. Hydrogen chloride (4M in diethyl ether, ml) was added and left to stir for 3 days, then hydrochloric acid (2M, 5 ml) was added and after 1 hour the mixture was washed with diethyl ether, basified with 2N sodium hydroxide, extracte with diethyl ether, dried (magnesium sulphate), filtered and the solvents removed in vacuo and the residue was purified by column chromatography on silica gel eluting with dichloromethane:methanol:880 ammonia (242/8/0.8 to 95/5/0.5 by volume) to furnish the title compound as a colourless oil, 100 mg.

LRMS: m/z 566 [M+H]$^+$.

Preparation 22

N-{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanesulfonamide

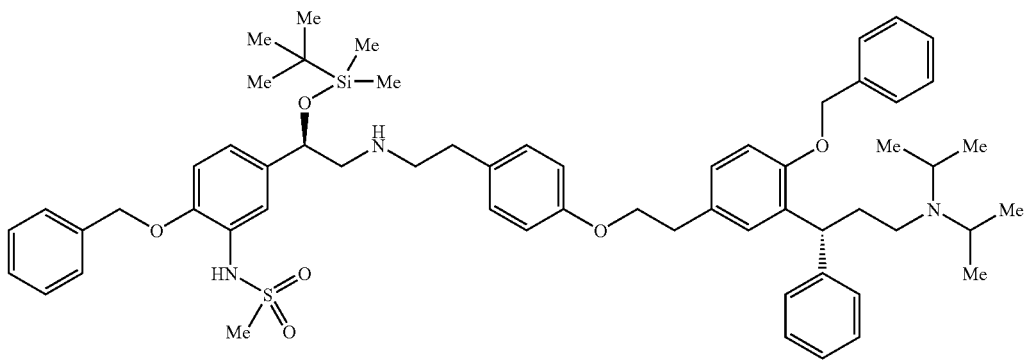

Preparation 21

(3R)-3-[5-{2-[4-(2-aminoethyl)phenoxy]ethyl}-2-(benzyloxy)phenyl]-N,N-diisopropyl-3-phenylpropan-1-amine

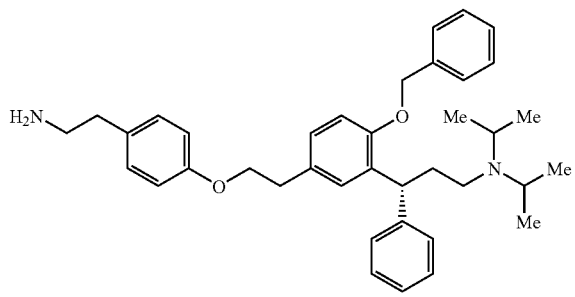

2-{4-(benzyloxy)-3-[(1R)-3-(diisopropylamino)-1-phenylpropyl]phenyl}ethanol (Prepared according to WO9843942, 390 mg, 0.88 mmol) was dissolved in tetrahydrofuran (6 ml), triphenylphosphine (344 mg, 1.31 mmol) then di-tert-butyl(E)-diazene-1,2-dicarboxylate (265 mg, 1.31 mmol) was added and the mixture was stirred for 20 minutes. tert-butyl[2-(4-hydroxyphenyl)ethyl]carbamate (Prepared according to WO2004/020415, 311 mg, 1.31

(3R)-3-[5-{2-[4-(2-aminoethyl)phenoxy]ethyl}-2-(benzyloxy)phenyl]-N,N-diisopropyl-3-phenylpropan-1-amine (Preparation 21, 95 mg, 0.17 mmol), N-{2-(benzyloxy)-5-[(1R)-2-bromo-1-{[tert-butyl(dimethyl)silyl]oxy}ethyl]phenyl}methanesulfonamide (WO2005/080324, 86 mg, 0.17 mmol), sodium hydrogen carbonate (42 mg, 0.51 mmol) and potassium iodide (28 mg, 0.17 mmol) were added to acetonitrile (2.5 ml) and heated to reflux for 24 hours, then cooled to room temperature and the solvents removed in vacuo, the residue was purified by column chromatography on silica gel eluting with dichloromethane:methanol:880 ammonia (2421810.8 to 95/5/0.5 by volume) to furnish the title compound as a white foam, 78 mg.

LRMS: m/z 999 [M+H]$^+$.

Preparation 23

6-(But-3-en-1-yloxy)hexanenitrile

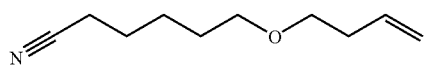

6-Bromocapronitrile (1.19 ml, 9.00 mmol) and 3-buten-1-ol (946 ul, 11.0 mmol) were added to a stirred solution of potassium hydroxide (6.16 g, 110 mmol) and tetra-butylammonium bromide (434 mg, 1.35 mmol) in water (6 ml) and dichloromethane (2 ml). The reaction was stirred at room temperature for 4 days and then washed with diethyl ether (2×50 ml). The combined organics were washed with water (3×30 ml), dried (magnesium sulphate) and the solvent removed in vacuo to furnish the title compound as a colourless oil, 1.48 g.

LRMS: m/z 168 [M+H]$^+$.

Preparation 24

6-{[(3E)-4-{4-(Benzyloxy)-3-[(1R)-3-(diisopropylamino)-1-phenylpropyl]phenyl}but-3-en-1-yl]oxy}hexanenitrile

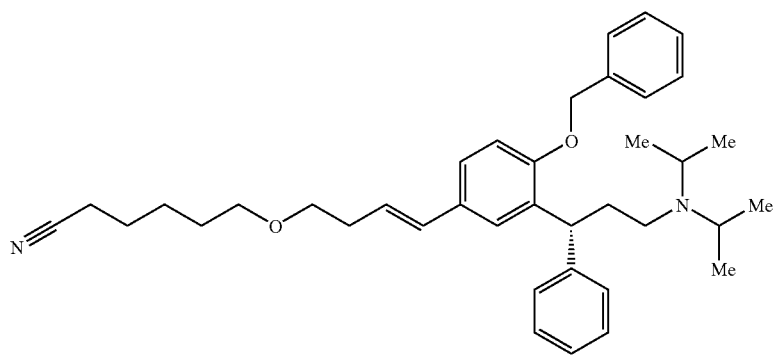

(3R)-3-[2-(Benzyloxy)-5-bromophenyl]-N,N-diisopropyl-3-phenylpropan-1-amine (WO9411337, 1.21 g, 2.50 mmol) was dissolved in acetonitrile (8 ml) and 6-(but-3-en-1-yloxy)hexanenitrile (Preparation 23, 708 mg, 4.20 mmol), diisopropylethylamine (0.64 ml, 3.75 mmol), palladium acetate (54 mg, 0.25 mmol) and tri(o-tolyl)phosphine (145 mg, 0.25 mmol) were added. The stirred reaction was heated at 90° C., under a nitrogen atmosphere, for 12 hours, cooled to room temperature and the solvent removed in vacuo. The residue was dissolved in ethyl acetate (50 ml) and washed with saturated aqueous sodium hydrogen carbonate (50 ml), brine (50 ml), dried (magnesium sulphate) and the solvent removed in vacuo. The residue was purified by column chromatography on silica gel eluting with dichloromethane:methanol:880 ammonia (95/5/0.5 by volume) to furnish the title compound as an oil, 960 mg.

LRMS: m/z 567 [M+H]$^+$.

Preparation 25

6-(4-{3-[(1R)-3-(Diisopropylamino)-1-phenylpropyl]-4-hydroxyphenyl}butoxy)hexanenitrile

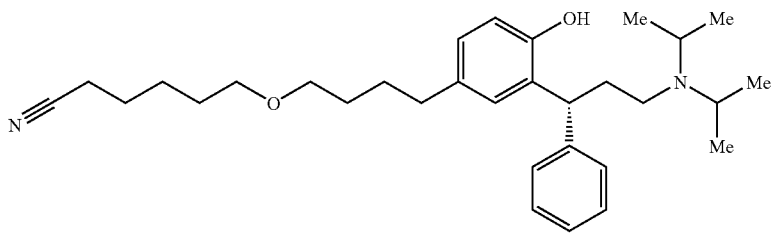

6-{[(3E)-4-{4-(Benzyloxy)-3-[(1R)-3-(diisopropylamino)-1-phenylpropyl]phenyl}but-3-en-1-yl]oxy}hexanenitrile (Preparation 24, 935 mg, 1.65 mmol) was dissolved in ethanol (20 ml) and ammonium formate (1.90 g, 30.0 mmol) and 10% palladium hydroxide on carbon (190 mg) added. The reaction was heated under reflux for 1 hour, cooled to room temperature and the reaction filtered through Arbocel™, the filtrate solvent was removed in vacuo to furnish the title compound as a colourless oil, 783 mg.

LRMS: m/z 479 [M+H]$^+$.

Preparation 26

4-{4-[(6-Aminohexyl)oxy]butyl}-2-[(1R)-3-(diisopropylamino)-1-phenylpropyl]phenol

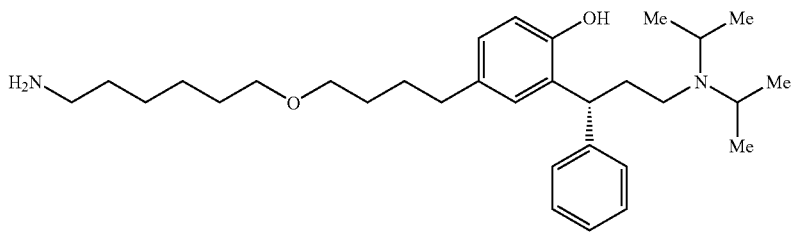

6-(4-{3-[(1R)-3-(Diisopropylamino)-1-phenylpropyl]-4-hydroxyphenyl}butoxy)hexanenitrile (Preparation 25, 783 mg, 1.64 mmol) was dissolved in ethanol (20 ml) and Raney nickel (100 mg) added. The reaction was hydrogenated under 60 psi at 40° C. for 18 hours, cooled to room temperature and the reaction filtered through Arbocel™ and the filtrate solvent removed in vacuo. The residue was purified by column chromatography on silica gel eluting with dichloromethane:methanol:880 ammonia (90/10/1.0 by volume) to furnish the title compound, 506 mg.

LRMS: m/z 481 [M+H]$^+$.

Preparation 27

N-{2-(Benzyloxy)-5-[(1R)-1-{[tert-butyl(dimethyl)silyl]oxy}-2-{[6-(4-{3-[(1R)-3-(diisopropylamino)-1-phenylpropyl]-4-hydroxyphenyl}butoxy)hexyl]amino}ethyl]phenyl}methanesulfonamide

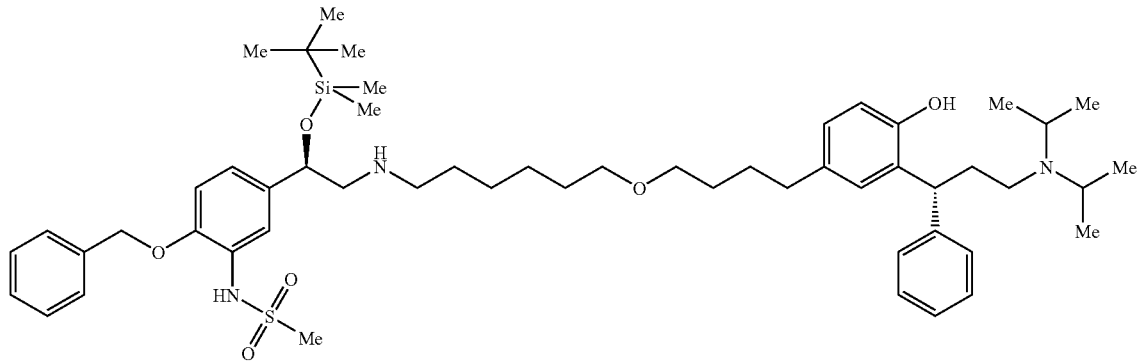

4-{4-[(6-Aminohexyl)oxy]butyl}-2-[(1R)-3-(diisopropylamino)-1-phenylpropyl]phenol (Preparation 26, 153 mg, 0.32 mmol) and N-{2-(benzyloxy)-5-[(1R)-2-bromo-1-{[tert-butyl(dimethyl)silyl]oxy}ethyl]phenyl}methanesulfonamide (Prepared according to WO2005/080324, 155 mg, 0.32 mmol), potassium iodide (10 mg) and sodium hydrogen carbonate (104 mg, 1.23 mmol) were heated in propionitrile (3 ml) at 90° C. for 24 hours. The reaction was cooled to room temperature and the solvent removed in vacuo. The residue was dissolved in ethyl acetate (30 ml), washed with aqueous saturated sodium hydrogen carbonate (30 ml), water (30 ml), brine (30 ml) and dried (magnesium sulphate). The solvent was removed in vacuo and the oil was purified by column chromatography on silica gel eluting with dichloromethane:methanol:880 ammonia (85:11:1.5 by volume) to furnish the title compound as a yellow oil, 130 mg.

LRMS (ES): m/z 917 [M+H]⁺.

Preparation 28

N-{5-[(1R)-1-{[tert-Butyl(dimethyl)silyl]oxy}-2-{[6-(4-{3-[(1R)-3-(diisopropylamino)-1-phenylpropyl]-4-hydroxyphenyl}butoxy)hexyl]amino}ethyl]-2-hydroxyphenyl}methanesulfonamide

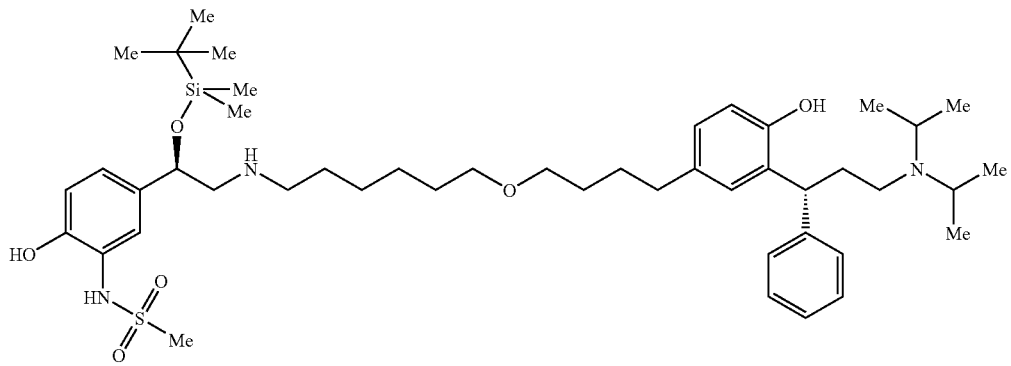

N-{2-(Benzyloxy)-5-[(1R)-1-{[tert-butyl(dimethyl)silyl]oxy}-2-{[6-(4-{3-[(1R)-3-(diisopropylamino)-1-phenylpropyl]-4-hydroxyphenyl}butoxy)hexyl]amino}ethyl]phenyl}methanesulfonamide (Preparation 27, 530 mg, 0.55 mmol) was dissolved in ethanol and ammonium formate (700 mg, 10.9 mmol) and 10% palladium hydroxide on carbon (100 mg) was added. The reaction was heated under reflux for 12 hours, cooled to room temperature and further ammonium formate (600 mg, 9.37 mmol) and 10% palladium hydroxide on carbon (60 mg) added. The reaction was heated under reflux for 3 hours, cooled to room temperature and further 10% palladium hydroxide on carbon (60 mg) added. The reaction was heated under reflux for 3 hours, cooled to room temperature and filtered through Arbocel™. The filtrate solvent was removed in vacuo and the oil was purified by column chromatography on silica gel eluting with dichloromethane:methanol:880 ammonia (80/20/2.0 by volume) to furnish the title compound as a yellow oil, 420 mg.

LRMS (ES): m/z 827 [M+H]$^+$.

Preparation 29

N-{2-(benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]phenyl}formamide mixture stirred at 90° C. for further 24 hours. After cooling, ethyl acetate and saturated aqueous sodium hydrogen carbonate were added, organics separated and washed with more saturated aqueous sodium hydrogen carbonate, then brine and then dried (magnesium sulphate) and solvent removed in vacuo. The residue was purified by column chromatography on silica gel eluting with dichloromethane:methanol:880 ammonia (96:4:0.4 to 92:8:0.8 by volume) to furnish the title compound as an oil, 400 mg.

LRMS: m/z 887 [M+H]$^+$.

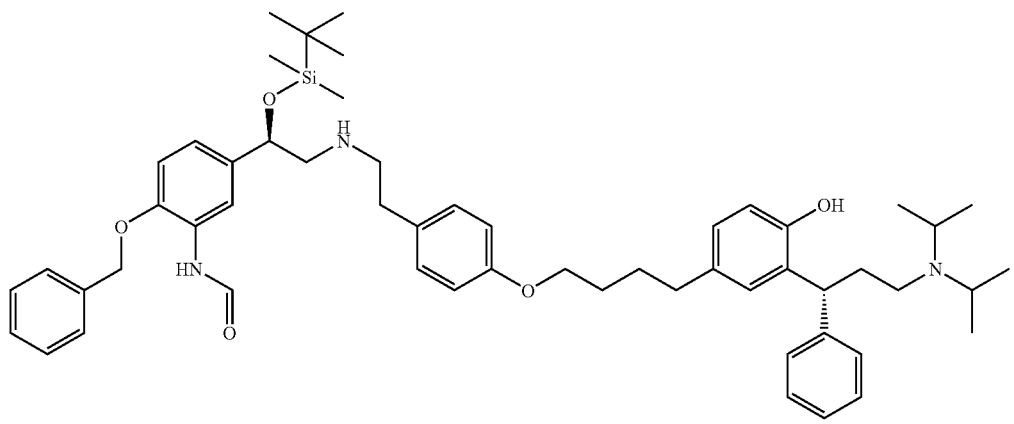

N-{2-(benzyloxy)-5-[(1R)-2-bromo-1-{[tert-butyl(dimethyl)silyl]oxy}ethyl]phenyl}formamide (Prepared according to US2005/215590, 500 mg, 1.1 mmol), 4-{4-[4-(2-aminoethyl)phenoxy]butyl}-2-[(1R)-3-(diisopropylamino)-1-phenylpropyl]phenol bis hydrochloride salt (Preparation 13, 745 mg, 1.3 mmol), sodium hydrogen carbonate (550 mg, 6.5 mmol) and potassium iodide (50 mg, 0.30 mmol) were added to propionitrile (8 ml) and heated to 90° C. and left to stir overnight. Further 4-{4-[4-(2-aminoethyl)phenoxy]butyl}-2-[(1R)-3-(diisopropylamino)-1-phenylpropyl]phenol (Preparation 13, 50 mg, 0.087 mmol) was then added and Preparation 30

N-{5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-hydroxyphenyl}formamide

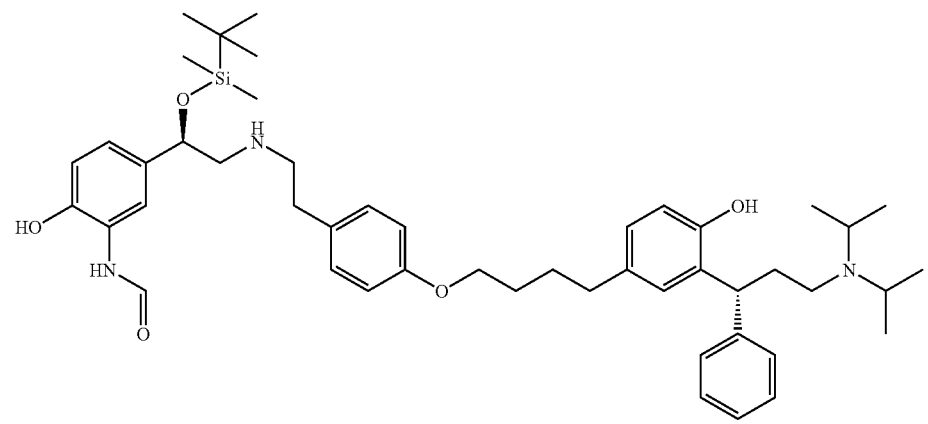

N-{2-(benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]phenyl}formamide (Preparation 29, 400 mg, 0.45 mmol), ammonium formate (570 mg, 9.0 mmol) and 20% palladium hydroxide on carbon (60 mg) were mixed in methanol (8 ml) and stirred at 70° C. for 1 hour under nitrogen. Further ammonium formate (500 mg, 7.9 mmol) and 20% palladium hydroxide on carbon (50 mg) were then added and heating continued at 70° C. for further 1 hour. Reaction mixture was then cooled and filtered, the filtrate was collected and the solvent removed in vacuo. The residue was dissolved in methanol (8 ml) and ammonium formate (500 mg, 7.9 mmol) and 20% palladium hydroxide on carbon (50 mg) were added and stirred at 70° C. for 1 hour under nitrogen. Reaction mixture was then cooled and filtered, the filtrate was collected and the solvent removed in vacuo. The residue was dissolved in ethyl actate (25 ml) and saturated aqueous sodium hydrogen carbonate (25 ml). Organics were separated and washed with brine (15 ml), dried (magnesium sulphate) and solvent was removed in vacuo to furnish the title compound as a yellow solid, 280 mg.

LRMS: m/z 797 [M+H]+.

Preparation 31

8-(benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]quinolin-2(1H)-one

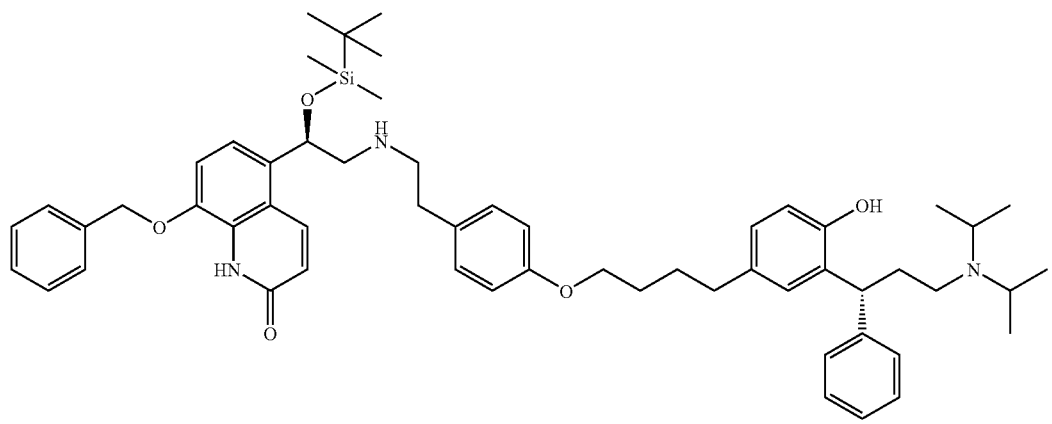

8-(benzyloxy)-5-[(1R)-2-bromo-1-{[tert-butyl(dimethyl)silyl]oxy}ethyl]quinolin-2(1H)-one (Prepared according to WO2005/092861, 530 mg, 1.1 mmol), 4-{4-[4-(2-aminoethyl)phenoxy]butyl}-2-[(1R)-3-(diisopropylamino)-1-phenylpropyl]phenol bis hydrochloride salt (Preparation 13, 650 mg, 1.3 mmol), sodium hydrogen carbonate (550 mg, 6.5 mmol) and potassium iodide (50 mg, 0.30 mmol) were added to propionitrile (8 ml) and heated to 90° C. and left to stir overnight. After cooling, ethyl acetate and saturated aqueous sodium hydrogen carbonate were added, organics separated and washed with more saturated aqueous sodium hydrogen carbonate, then brine and then dried (magnesium sulphate) and solvent removed in vacuo. The residue was purified by column chromatography on silica gel eluting with dichloromethane:methanol:880 ammonia (100/0/0 to 94/6/0.6 by volume) to furnish the title compound as an oil, 406 mg.

LRMS: m/z 911 [M+H]+.

Preparation 32

5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-8-hydroxyquinolin-2(1H)-one

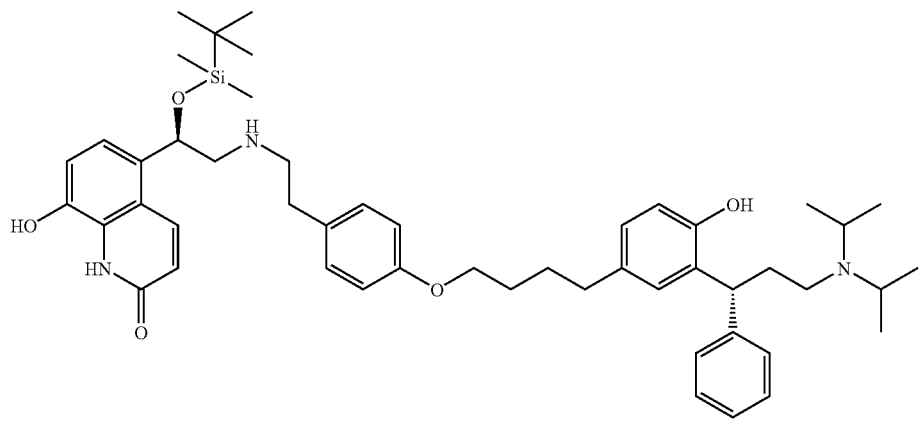

8-(benzyloxy)-5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]quinolin-2(1H)-one (Preparation 31, 406 mg, 0.45 mmol), ammonium formate (560 mg, 9.0 mmol) and 20% palladium hydroxide on carbon (60 mg) were mixed in methanol (8 ml) and stirred at 70° C. for 1 hour under nitrogen. Further ammonium formate (300 mg, 4.8 mmol) and 20% palladium hydroxide on carbon (30 mg) were then added and heating continued at 70° C. for further 1 hour. Reaction mixture was then cooled and filtered, the filtrate was collected and the solvent removed in vacuo. Residue was dissolved in ethyl acetate (25 ml) and saturated aqueous sodium hydrogen carbonate (25 ml). Organics were separated and washed with brine (15 ml), dried (magnesium sulphate) and solvent was removed in vacuo to furnish the title compound as a yellow solid, 305 mg.

LRMS: m/z 821 [M+H]+.

Preparation 33

4-{4-[4-(2-{[(2R)-2-[3,5-bis(benzyloxy)phenyl]-2-{[tert-butyl(dimethyl)silyl]oxy}ethyl]amino}ethyl)phenoxy]butyl}-2-[(1R)-3-(diisopropylamino)-1-phenylpropyl]phenol {(1R)-1-[3,5-bis(benzyloxy)phenyl]-2-bromoethoxy}(tert-butyl)dimethylsilane (Prepared according to US2005/222128, 570 mg, 1.1 mmol), 4-{4-[4-(2-aminoethyl)phenoxy]butyl}-2-[(1R)-3-(diisopropylamino)-1-phenylpropyl]phenol bis hydrochloride salt (Preparation 13, 746 mg, 1.3 mmol), sodium hydrogen carbonate (544 mg, 6.48 mmol) and potassium iodide (50 mg, 0.30 mmol) were added to propionitrile (8 ml) and heated to 90° C. and left to stir overnight. After cooling, ethyl acetate and saturated aqueous sodium hydrogen carbonate were added, organics separated and washed with more saturated aqueous sodium hydrogen carbonate, then brine and then dried (magnesium sulphate) and solvent removed in vacuo. The residue was purified by column chromatography on silica gel eluting with dichloromethane:methanol:880 ammonia (100:0:0 to 94:6:0.6 by volume) to furnish the title compound as a yellow oil, 720 mg.

LRMS: m/z 950 [M+H]+.

Preparation 34

5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]benzene-1,3-diol (25 ml). Organics were separated and washed with brine (15 ml), dried (magnesium sulphate) and solvent was removed in vacuo to furnish the title compound as an off-white foam, 555 mg.

LRMS: m/z 770 [M+H]+.

Preparation 35 tert-butyl[2-(3-hydroxyphenyl)ethyl]carbamate

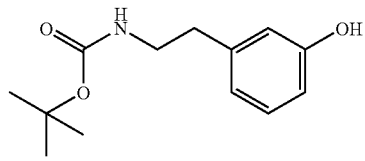

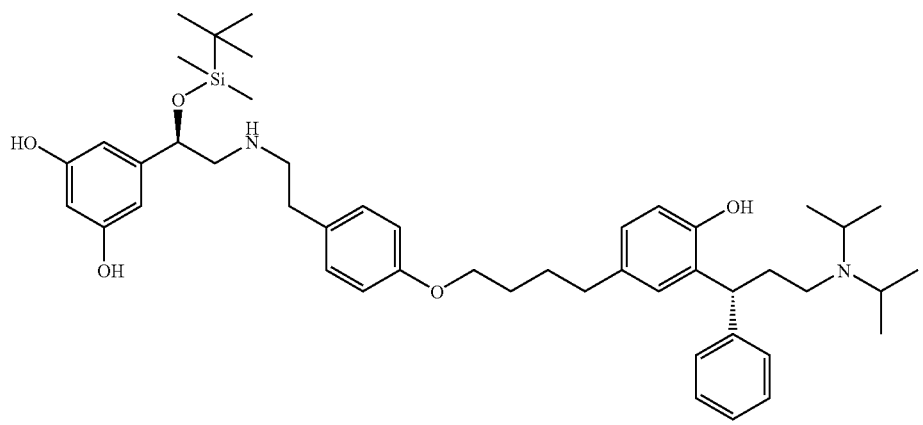

4-{4-[4-(2-{[(2R)-2-[3,5-bis(benzyloxy)phenyl]-2-{[tert-butyl(dimethyl)silyl]oxy}ethyl]amino}ethyl)phenoxy]butyl}-2-[(1R)-3-(diisopropylamino)-1-phenylpropyl]phenol (Preparation 33, 720 mg, 0.76 mmol), ammonium formate (960 mg, 15.0 mmol) and 20% palladium hydroxide on carbon (110 mg) were mixed in methanol (8 ml) and stirred at 70° C. for 1 hour under nitrogen. Further ammonium formate (300 mg, 4.75 mmol) and 20% palladium hydroxide on carbon (30 mg) were then added and heating continued at 70° C. for further 1 hour. Reaction mixture was then cooled and filtered, the filtrate was collected and the solvent removed in vacuo. The residue was dissolved in methanol (8 ml) and ammonium formate (900 mg, 14 mmol) and 20% palladium hydroxide on carbon (100 mg) were added and stirred at 70° C. for 1 hour under nitrogen. Reaction mixture was then cooled and filtered, the filtrate was collected and the solvent removed in vacuo. The residue was dissolved in ethyl actate (25 ml) and saturated aqueous sodium hydrogen carbonate 3-(2-aminoethyl)phenol hydrochloride (3 g, 17.3 mmol) and triethylamine (6.02 ml, 43.2 mmol) dissolved in water (15 ml) and 1,4-dioxan (45 ml) and di-tert-butyl dicarbonate (4.52 g, 1.20 mmol) added. Mixture stirred at room temperature for 2 days. Diethyl ether (100 ml) and hydrogen chloride (2M in water, 100 ml) were then added and organics separated and washed with saturated aqueous sodium hydrogen carbonate (100 ml), then brine (100 ml) then dried (magnesium sulphate) and the solvent was removed in vacuo to furnish the title compound as a clear gum, 4.42 g.

LRMS: m/z 260 [M+Na]+.

Preparation 36

2-{4-(benzyloxy)-3-[(1R)-3-(diisopropylamino)-1-phenylpropyl]phenyl}ethyl methanesulfonate

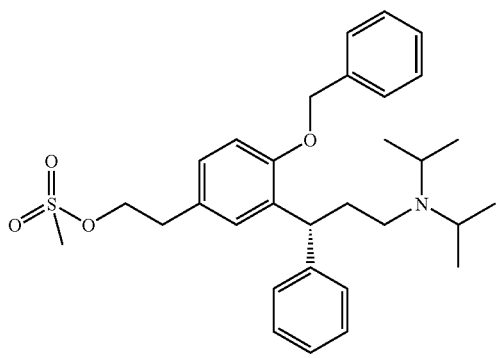

2-{4-(benzyloxy)-3-[(1R)-3-(diisopropylamino)-1-phenylpropyl]phenyl}ethanol (Prepared according to WO1998/43942, 1.0 g, 2.25 mmol) was dissolved in dichloromethane (20 ml) and N,N-diisopropyl ethylamine (1.8 ml, 10 mmol) added. The solution was then cooled to 0° C. and methanesulphonyl chloride (0.42 ml, 5.4 mmol) was added. After stirring for 2 hours at 0° C. the mixture was diluted with dichloromethane (20 ml) and washed with water (50 ml), brine (50 ml) and then dried (magnesium sulphate) and the solvent removed in vacuo to yield the title compound as a yellow oil, 1.56 g.

LRMS: m/z 524 [M+H]⁺.

Preparation 37 tert-butyl{2-[3-(2-{4-(benzyloxy)-3-[(1R)-3-(diisopropylamino)-1-phenylpropyl]phenyl}ethoxy)phenyl]ethyl}carbamate

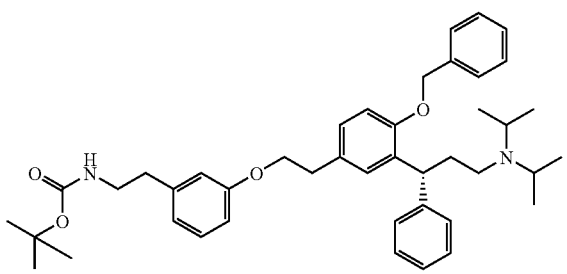

tert-butyl[2-(3-hydroxyphenyl)ethyl]carbamate (Preparation 35, 1.7 g, 5.96 mmol), potassium carbonate (1.65 g, 11.9 mmol), potassium iodide (5.0 g, 0.03 mmol) and 2-{4-(benzyloxy)-3-[(1R)-3-(diisopropylamino)-1-phenylpropyl]phenyl}ethyl methanesulfonate (Preparation 36, 1.56 g, 2.98 mmol) were stirred in dimethylformamide (20 ml) and stirred at 60° C. overnight. After cooling, water (250 ml) and diethyl ether (250 ml) were added, organics separated and washed with water (100 ml×3), brine (150 ml) then dried (magnesium sulphate) and the solvent removed in vacuo. The residue was purified by column chromatography on silica gel eluting with dichloromethane:methanol:880 ammonia (100/0/0 to 90/10/1.0 by volume) to furnish the title compound as an oil, 1.3 g.

LRMS: m/z 666 [M+H]⁺.

Preparation 38

(3R)-3-[5-{2-[3-(2-aminoethyl)phenoxy]ethyl}-2-(benzyloxy)phenyl]-N,N-diisopropyl-3-phenylpropan-1-amine

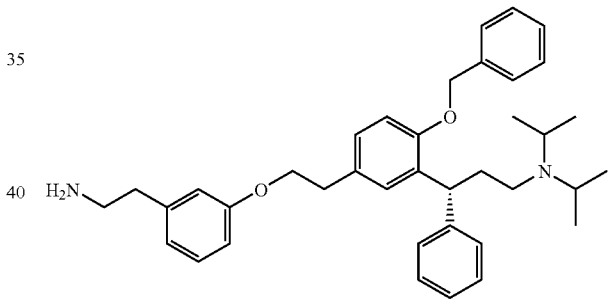

tert-butyl{2-[3-(2-{4-(benzyloxy)-3-[(1R)-3-(diisopropylamino)-1-phenylpropyl]phenyl}ethoxy)phenyl]ethyl}carbamate (Preparation 37, 1.3 g, 2.0 mmol) dissolved in dichloromethane (5 ml) and hydrochloric acid (4M in dioxin) added. Mixture stirred at room temperature for 3 hours under nitrogen. Solvent was removed in vacuo, and residue dissolved in dichloromethane (100 ml) and aqueous sodium hydroxide (1M, 100 ml), aqueous separated and extracted with dichloromethane (100 ml). Combined organics were dried (magnesium sulphate) and the solvent was removed in vacuo to furnish the title compound as an oil, 880 mg.

LRMS: m/z 565 [M+H]⁺.

Preparation 39

N-{2-(benzyloxy)-5-[(1R)-2-({2-[3-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanesulfonamide

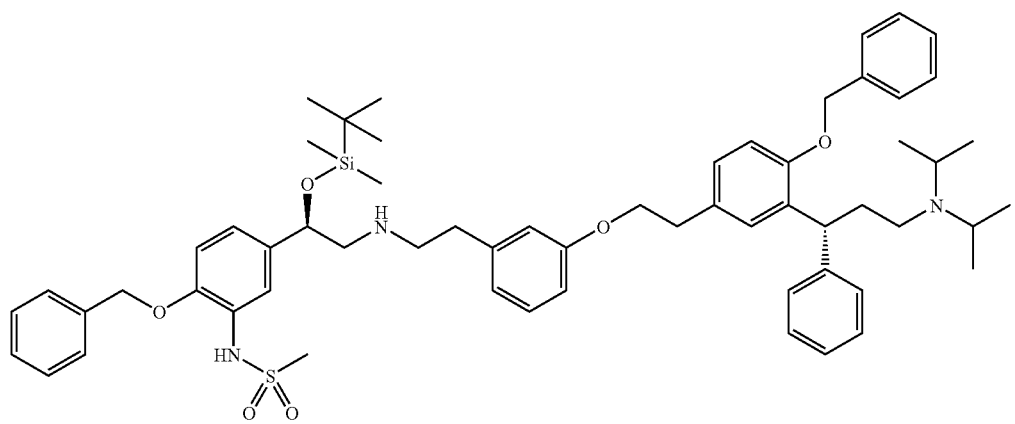

(3R)-3-[5-{2-[3-(2-aminoethyl)phenoxy]ethyl}-2-(benzyloxy)phenyl]-N,N-diisopropyl-3-phenylpropan-1-amine (Preparation 38, 340 mg, 0.52 mmol), potassium iodide (86 mg, 0.52 mmol), sodium hydrogen carbonate (175 mg, 2.08 mmol) and N-{2-(benzyloxy)-5-[(1R)-2-bromo-1-{[tert-butyl(dimethyl)silyl]oxy}ethyl]phenyl}methanesulfonamide (Prepared according to WO2005/080324, 270 mg, 0.52 mmol) were added to propionitrile (5 ml) and stirred at 100° C. under nitrogen overnight. Mixture was cooled and water (100 ml) and ethyl acetate (100 ml) were added. Organics were separated and washed with brine (100 ml), dried (magnesium sulphate) and the solvent removed in vacuo. The residue was purified by column chromatography on silica gel eluting with dichloromethane:methanol:880 ammonia (100/0/0 to 85/15/1.5 by volume) to furnish the title compound as a glass, 257 mg.

LRMS: m/z 999 [M+H]$^+$.

Preparation 40

{2-(benzyloxy)-5-[(1R)-2-({2-[3-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanol

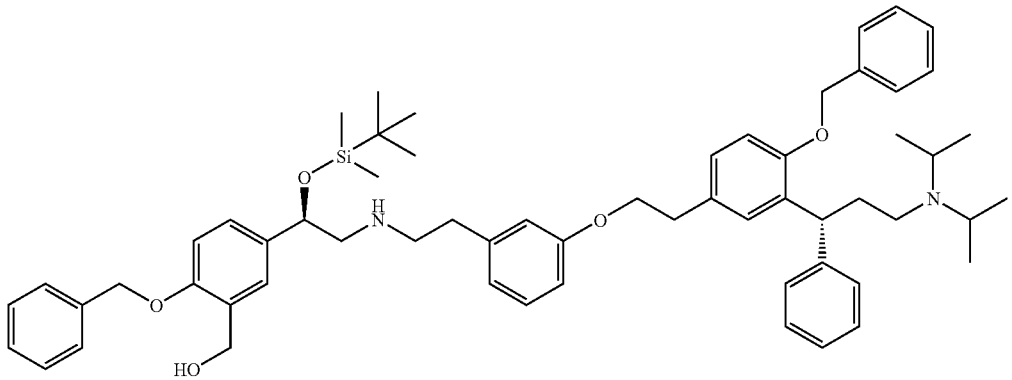

(3R)-3-[5-{2-[3-(2-aminoethyl)phenoxy]ethyl}-2-(benzyloxy)phenyl]-N,N-diisopropyl-3-phenylpropan-1-amine (Preparation 38, 470 mg, 0.72 mmol), potassium iodide (120 mg, 0.72 mmol), sodium hydrogen carbonate (240 mg, 2.9 mmol) and {2-(benzyloxy)-5-[(1R)-2-bromo-1-{[tert-butyl(dimethyl)silyl]oxy}ethyl]phenyl}methanol (Prepared according to WO2004/032921, 325 mg, 0.72 mmol) were stirred in propionitrile at 100° C. for 24 hours under nitrogen. After cooling to room temperature, water (100 ml) and ethyl acetate (100 ml) were added, organics separated and washed with brine (100 ml), dried (magnesium sulphate) and solvent removed in vacuo. The residue was purified by column chromatography on silica gel eluting with dichloromethane:methanol:880 ammonia (100/0/0 to 85/15/1.5 by volume) to furnish the title compound as a brown glass, 450 mg.

LRMS: m/z 935 [M+H]+.

Preparation 41 tert-butyl{2-[4-(2-{4-(benzyloxy)-3-[(1R)-3-(diisopropylamino)-1-phenylpropyl]phenyl}ethoxy)phenyl]ethyl}carbamate

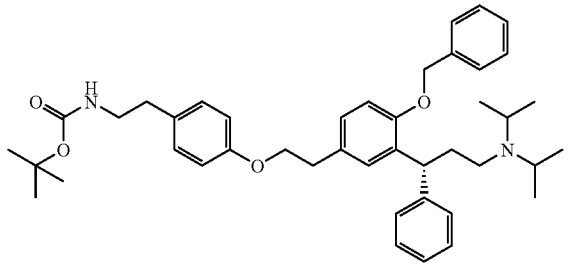

tert-butyl[2-(4-hydroxyphenyl)ethyl]carbamate (Prepared according to WO1998/43942, 3.8 g, 7.3 mmol), potassium carbonate (2.6 g, 8.0 mmol), potassium iodide (1.1 g, 7.3 mmol) and 2-{4-(benzyloxy)-3-[(1R)-3-(diisopropylamino)-1-phenylpropyl]phenyl}ethyl methanesulfonate (preparation 36, 1.56 g, 2.98 mmol) were stirred in toluene (20 ml) and stirred at 120° C. overnight. After cooling, water (80 ml) and ethyl acetate (80 ml) were added, organics separated and washed with saturated aqueous sodium hydrogen carbonate (40 ml), brine (40 ml) then dried (magnesium sulphate) and the solvent removed in vacuo. The residue was purified by column chromatography on silica gel eluting with dichloromethane:methanol:880 ammonia (99/1/0.1 to 90/10/1.0 by volume) to furnish the title compound as an oil, 3.4 g.

LRMS: m/z 666 [M+H]+.

Preparation 42

(3R)-3-[5-{2-[4-(2-aminoethyl)phenoxy]ethyl}-2-(benzyloxy)phenyl]-N,N-diisopropyl-3-phenylpropan-1-amine bis hydrochloride salt

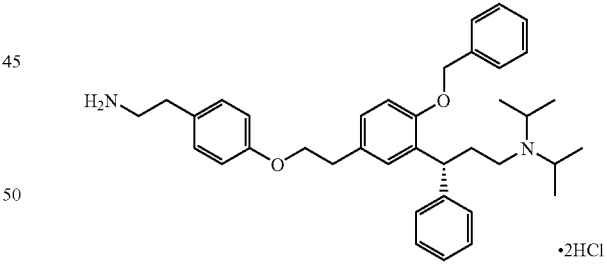

tert-butyl{2-[4-(2-{4-(benzyloxy)-3-[(1R)-3-(diisopropylamino)-1-phenylpropyl]phenyl}ethoxy)phenyl]ethyl}carbamate (Preparation 41, 3.4 g, 5.1 mmol) was dissolved in dioxan (20 ml) and treated with hydrochloric acid (4M in dioxan, 26 ml). After stirring for 4 hours at room temperature the solvent was removed in vacuo. The residue was azeotroped twice from dichloromethane to yield the title compound as a brown solid, 3.

LRMS: m/z 565 [M+H]+.

Preparation 43

(3R)-3-[2-(benzyloxy)-5-{2-[4-(2-{[(2R)-2-[3,5-bis(benzyloxy)phenyl]-2-{[tert-butyl(dimethyl)silyl]oxy}ethyl]amino}ethyl)phenoxy]ethyl}phenyl]-N,N-diisopropyl-3-phenylpropan-1-amine

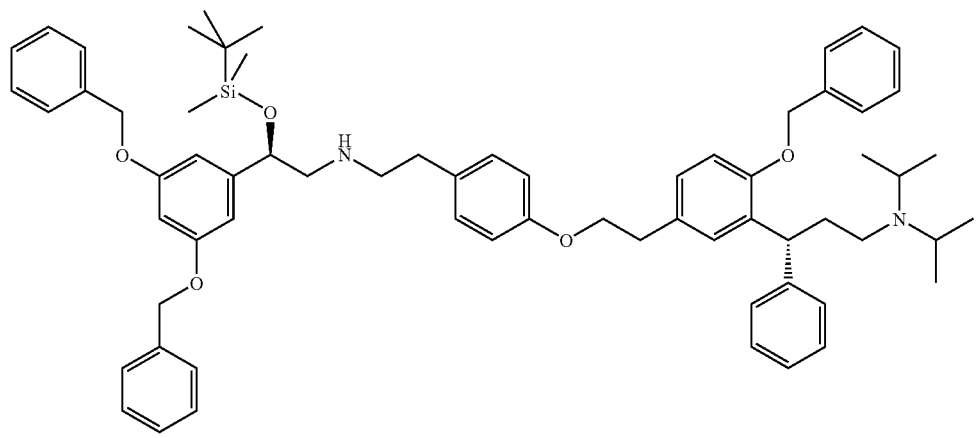

(3R)-3-[5-{2-[4-(2-aminoethyl)phenoxy]ethyl}-2-(benzyloxy)phenyl]-N,N-diisopropyl-3-phenylpropan-1-amine bis hydrochloride salt (Preparation 42, 600 mg, 0.94 mmol), {(1R)-1-[3,5-bis(benzyloxy)phenyl]-2-bromoethoxy}(tert-butyl)dimethylsilane (Prepared according to US2005/222128, 500 mg, 0.94 mmol), potassium iodide (160 mg, 0.94 mmol), sodium hydrogen carbonate (480 mg, 5.65 mmol) were added to propionitrile (10 ml) and stirred at 100° C. under nitrogen overnight. The mixture was cooled and water (75 ml) and ethyl acetate (75 ml) were added. Organics were separated and washed with brine (25 ml), dried (magnesium sulphate) and the solvent removed in vacuo. The residue was purified by column chromatography on silica gel eluting with dichloromethane:methanol:880 ammonia (99/1/0.1 to 90/10/1 by volume) to furnish the title compound as a gum, 346 mg.

LRMS: m/z 1012 [M+H]$^+$.

Preparation 44

5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]benzene-1,3-diol

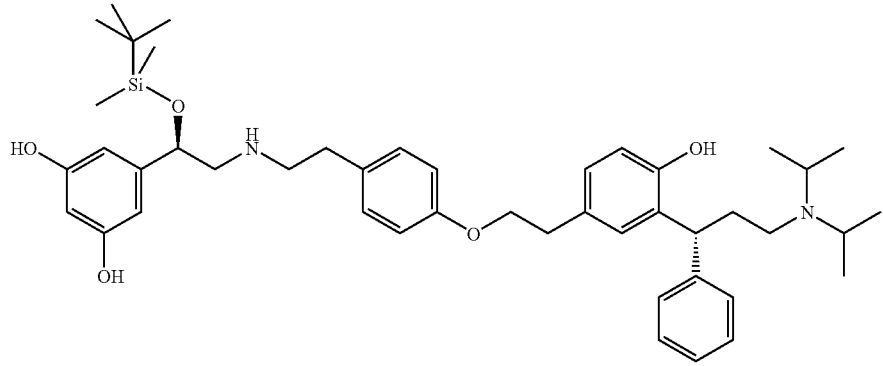

(3R)-3-[2-(benzyloxy)-5-{2-[4-(2-{[(2R)-2-[3,5-bis(benzyloxy)phenyl]-2-{[tert-butyl(dimethyl)silyl]oxy}ethyl]amino}ethyl)phenoxy]ethyl}phenyl]-N,N-diisopropyl-3-phenylpropan-1-amine (Preparation 43, 346 mg, 0.30 mmol) was dissolved in methanol (30 ml) and ammonium formate (380 mg, 6.1 mmol) and 20% palladium hydroxide on carbon (43 mg) added. The stirred reaction was then heated at 90° C. for 2 hours. After cooling to room temperature, mixture was filtered and solvent removed in vacuo. The residue was then taken up in ethyl acetate (50 ml) and saturated aqueous sodium hydrogen carbonate (50 ml). The organics were separated, washed with brine then dried (magnesium sulphate) and the solvent removed in vacuo to yield the title compound as a yellow glass, 174 mg.

LRMS: m/z 742 [M+H]$^+$.

Preparation 45

N-{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}formamide N-{2-(benzyloxy)-5-[(1R)-2-bromo-1-{[tert-butyl(dimethyl)silyl]oxy}ethyl]phenyl}formamide (Prepared according to US2005/215590, 440 mg, 0.95 mmol) (3R)-3-[5-{2-[4-(2-aminoethyl)phenoxy]ethyl}-2-(benzyloxy)phenyl]-N,N-diisopropyl-3-phenylpropan-1-amine bis hydrochloride salt (Preparation 42, 600 mg, 0.95 mmol) potassium iodide (160 mg, 0.94 mmol), sodium hydrogen carbonate (480 mg, 5.65 mmol) were added to propionitrile (10 ml) and stirred at 100° C. under nitrogen for 24 hours. The mixture was cooled and water (75 ml) and ethyl acetate (75 ml) were added. Organics were separated and washed with brine, dried (magnesium sulphate) and the solvent removed in vacuo. The residue was purified by column chromatography on silica gel eluting with dichloromethane:methanol:880 ammonia (99/1/0.1 to 90/10/1 by volume) to furnish the title compound as a gum, 174 mg.

LRMS: m/z 949 [M+H]$^+$.

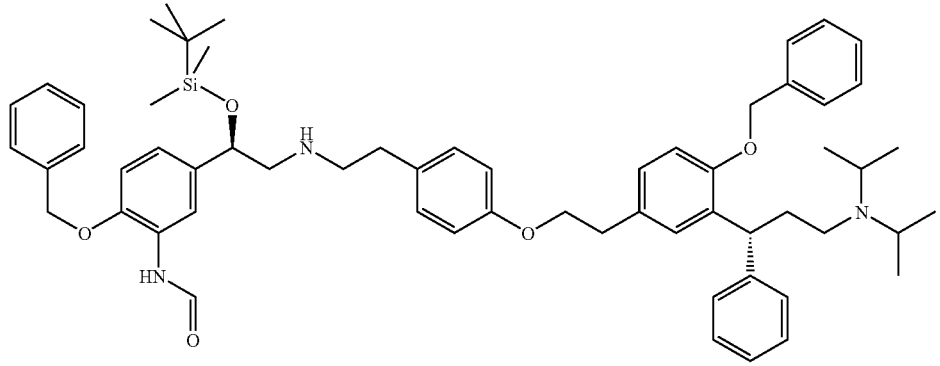

Preparation 46

N-{5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]-2-hydroxyphenyl}formamide

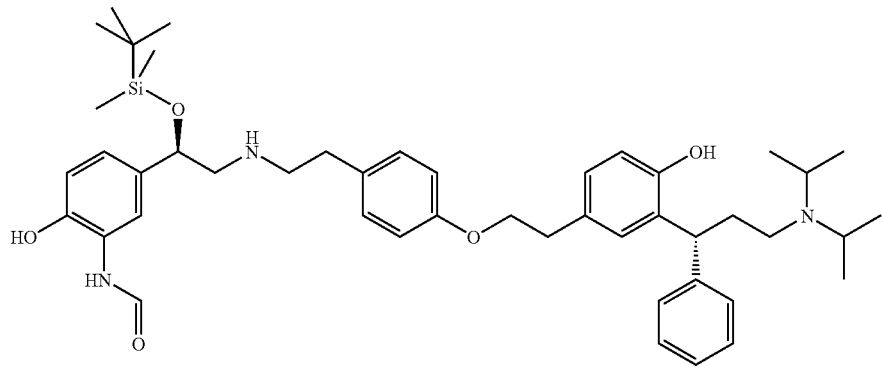

N-{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}formamide (Preparation 45, 174 mg, 0.18 mmol) was dissolved in methanol (20 ml) and ammonium formate (230 mg, 3.7 mmol) and 20% palladium hydroxide on carbon (26 mg) added. The stirred reaction was then heated at 90° C. for 2 hours. After cooling to room temperature, the mixture was filtered and solvent removed in vacuo. The residue was then taken up in ethyl acetate (50 ml) and saturated aqueous sodium hydrogen carbonate (50 ml). The organics were separated, washed with brine then dried (magnesium sulphate) and the solvent removed in vacuo to yield the title compound as a yellow glass, 180 mg.

LRMS: m/z 769 [M+H]+.

Preparation 47

8-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]quinolin-2(1H)-one (3R)-3-[5-{2-[4-(2-aminoethyl)phenoxy]ethyl}-2-(benzyloxy)phenyl]-N,N-diisopropyl-3-phenylpropan-1-amine bis hydrochloride salt (Preparation 42, 800 mg, 1.25 mmol), 8-(benzyloxy)-5-[(1R)-2-bromo-1-{[tert-butyl(dimethyl)silyl]oxy}ethyl]quinolin-2(1H)-one (Prepared according to WO2005/092861, 615 mg, 1.25 mmol), potassium iodide (210 mg, 1.25 mmol), sodium hydrogen carbonate (630 mg, 7.5 mmol) were added to propionitrile (15 ml) and stirred at 100° C. under nitrogen overnight. The mixture was cooled and water (100 ml) and ethyl acetate (100 ml) added. Organics were separated and washed with water (100 ml) then brine (50 ml), dried (magnesium sulphate) and the solvent removed in vacuo. The residue was purified by column chromatography on silica gel eluting with dichloromethane:methanol:880 ammonia (100/0/0 to 90/10/1 by volume) to furnish the title compound as a gum, 297 mg.

LRMS: m/z 973 [M+H]+.

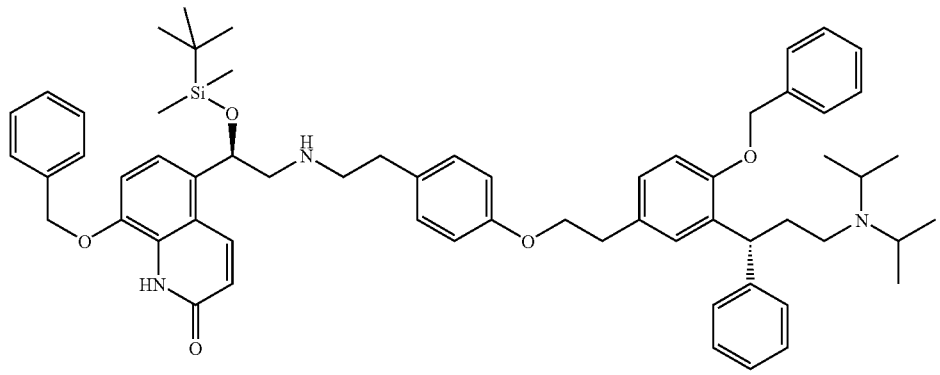

Preparation 48

{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanol

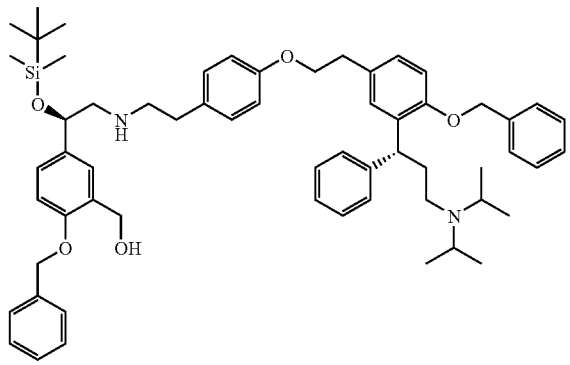

tert-butyl{2-[4-(2-{4-(benzyloxy)-3-[(1R)-3-(diisopropylamino)-1-phenylpropyl]phenyl}ethoxy)phenyl]ethyl}carbamate (Preparation 41, 830 mg, 1.25 mmol) was treated with hydrochloric acid (8 ml of a 4M solution in 1,4-dioxane) and stirred at room temperature overnight, and the solvent was removed in vacuo. The residue was dissolved in acteonitrile (8 ml) and {2-(benzyloxy)-5-[(1R)-2-bromo-1-{[tert-butyl(dimethyl)silyl]oxy}ethyl]phenyl}methanol (Sali patent, 560 mg, 1.24 mmol) and sodium hydrogen carbonate (368 mg, 4.34 mmol) added. Mixture heated to 85° C. and stirred overnight. Reaction was cooled to room temperature and ethyl acetate and water added, the aqueous layer was separated and washed with ethyl acetate and the combined organics dried (magnesium sulphate) and the solvent removed in vacuo. The residue was purified by column chromatography on silica gel eluting with dichloromethane:methanol:880 ammonia (92.5:7.5:1 by volume) to furnish the title compound as a gum, 280 mg.

LRMS: m/z 936 [M+H]$^+$.

Preparation 49

4-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]-2-(hydroxymethyl)phenol

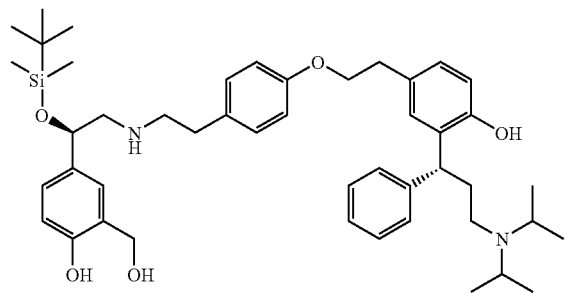

{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanol (Preparation 48, 280 mg, 0.30 mmol) was dissolved in ethanol (6 ml) and palladium hydroxide (20% by weight on carbon, 14 mg, 0.02 mmol) was added. The reaction was the hydrogenated under 40 psi at room temperature for 18 hours, cooled to room temperature and the reaction filtered through Celite™ and the filtrate solvent removed in vacuo to furnish the title compound as a gum, 235 mg.

LRMS: m/z 756 [M+H]$^+$.

Preparation 50 di-tert-butyl oct-7-en-1-ylimidodicarbonate

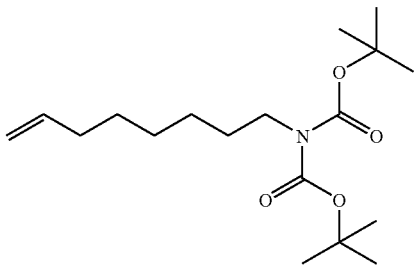

To a stirred suspension of sodium hydride (840 mg of a 60% dispersion in oil, 21.0 mmol) in N,N-dimethylformamide (40 ml) was added in one portion di-tert-butyl iminodicarbamate (4.56 g, 21.0 mmol). After stirring for 40 mins, 8-bromooct-1-ene (3.50 ml, 21 mmol) was added and mixture was stirred at room temperature overnight. The solvent was removed in vacuo and the residue dissolved in water and ethyl acetate. The organic layer was separated and washed with water then brine, dried (magnesium sulphate) and the solvent removed in vacuo. The residue was purified by column chromatography on silica gel eluting with diethyl ether:pentane (1/99 to 6/94 by volume) to furnish the title compound as a clear oil, 5.51 g.

Preparation 51 di-tert-butyl[(7E)-8-{4-(benzyloxy)-3-[(1R)-3-(diisopropylamino)-1-phenylpropyl]phenyl}oct-7-en-1-yl]imidodicarbonate

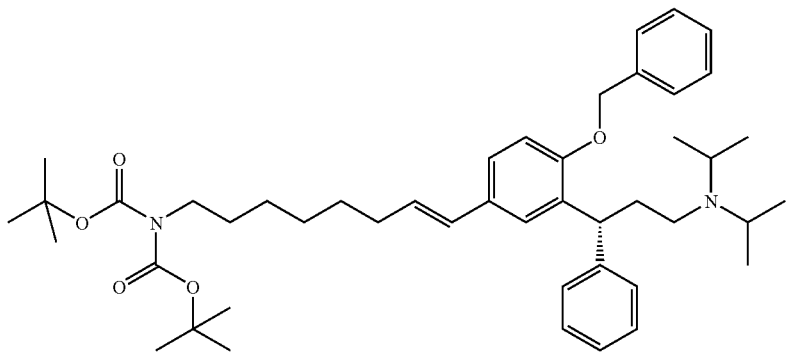

di-tert-butyl oct-7-en-1-ylimidodicarbonate (Preparation 48, 649 mg, 1.98 mmol), (3R)-3-[2-(benzyloxy)-5-bromophenyl]-N,N-diisopropyl-3-phenylpropan-1-amine (Prepared according to WO1994/11337, 560 mg, 1.16 mmol), palladium diacetate (27 mg, 0.12 mmol), tris(2-methylphenyl)phosphine (73 mg, 0.24 mmol) and N,N-diisopropylethylamine (0.304 ml, 1.75 mmol) were added to acetonitrile (6 ml) and the mixture was heated to 90° C. and left to stir overnight under nitrogen. Mixture was cooled and saturated aqueous sodium hydrogen carbonate and ethyl acetate were added. Organics separated and washed with saturated aqueous sodium hydrogen carbonate, brine, dried (magnesium sulphate) and the solvent removed in vacuo. The residue was purified by column chromatography on silica gel eluting with dichloromethane:methanol:880 ammonia (100/0/0 to 96/4/0.4 by volume) to furnish the title compound as a oil, 530 mg.

LRMS: m/z 727 [M+H]$^+$.

Preparation 52 di-tert-butyl(8-{3-[(1R)-3-(diisopropylamino)-1-phenylpropyl]-4-hydroxyphenyl}octyl)imidodicarbonate

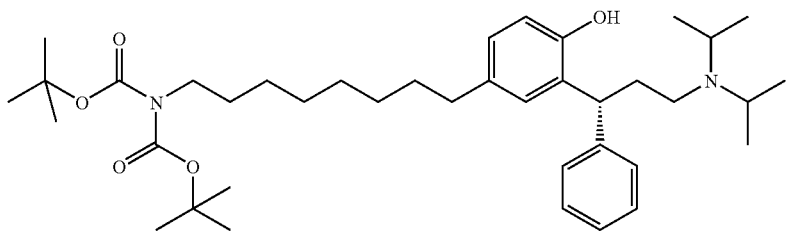

di-tert-butyl[(7E)-8-{4-(benzyloxy)-3-[(1R)-3-(diisopropylamino)-1-phenylpropyl]phenyl}oct-7-en-1-yl]imidodicarbonate (Preparation 51, 530 mg, 0.73 mmol), palladium hydroxide (20% by weight on carbon, 100 mg, 0.14 mmol) and ammonium formate (1.1 g, 17 mmol) were dissolved in ethanol (20 ml) and heated to 70° C. for 3 hours. Reaction mixture was cooled and filtered and the solvent removed in vacuo to yield the title compound as a clear oil, 340 mg.

LRMS: m/z 640 [M+H]$^+$.

Preparation 53

4-(8-aminooctyl)-2-[(1R)-3-(diisopropylamino)-1-phenylpropyl]phenol

Di-tert-butyl(8-{3-[(1R)-3-(diisopropylamino)-1-phenylpropyl]-4-hydroxyphenyl}octyl)imido dicarbonate (Preparation 52, 340 mg, 0.53 mmol) was dissolved in dichloromethane (5 ml) and hydrochloric acid (5.0 ml of a 2M solution in diethyl ether) was added, and the mixture stirred overnight at room temperature. Solvent was removed in vacuo and the residue dissolved in a mixture of ethyl acetate and saturated aqueous sodium hydrogen carbonate. Organic layer was separated, dried (magnesium sulphate) and solvent removed in vacuo to yield the title compound as a yellow oil, 170 mg.

LRMS: m/z 439 [M+H]+.

Preparation 54

N-[2-(benzyloxy)-5-{(1R)-1-{[tert-butyl(dimethyl)silyl]oxy}-2-[(8-{3-[(1R)-3-(diisopropylamino)-1-phenylpropyl]-4-hydroxyphenyl}octyl)amino]ethyl}phenyl]methanesulfonamide

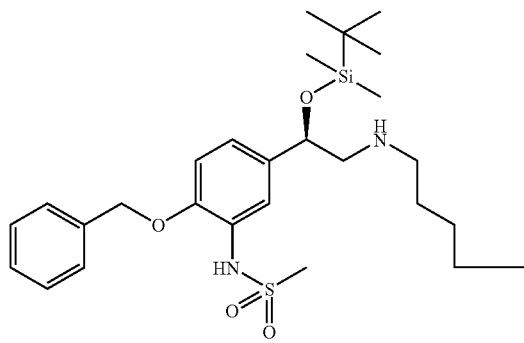

4-(8-aminooctyl)-2-[(1R)-3-(diisopropylamino)-1-phenylpropyl]phenol (Preparation 53, 170 mg, 0.39 mmol) and N-{2-(benzyloxy)-5-[(1R)-2-bromo-1-{[tert-butyl(dimethyl)silyl]oxy}ethyl]phenyl}methanesulfonamide (Prepared according to WO2005/080324, 191 mg, 0.37 mmol) were heated at 90° C. in dimethylsulfoxide (0.5 ml) overnight. Ethyl acetate and saturated aqueous sodium hydrogen carbonate were added and the organics separated, washed with saturated aqueous sodium hydrogen carbonate, brine, dried (magnesium sulphate) and the solvent removed in vacuo. The residue was purified by column chromatography on silica gel eluting with dichloromethane:methanol:880 ammonia (99/1/0.1 to 95/5/0.5 by volume) to furnish the title compound as a yellow oil, 90 mg.

LRMS: m/z 872 [M+H]+.

Preparation 55

N-(5-{(1R)-1-{[tert-butyl(dimethyl)silyl]oxy}-2-[(8-{3-[(1R)-3-(diisopropylamino)-1-phenylpropyl]-4-hydroxyphenyl}octyl)amino]ethyl}-2-hydroxyphenyl)methanesulfonamide

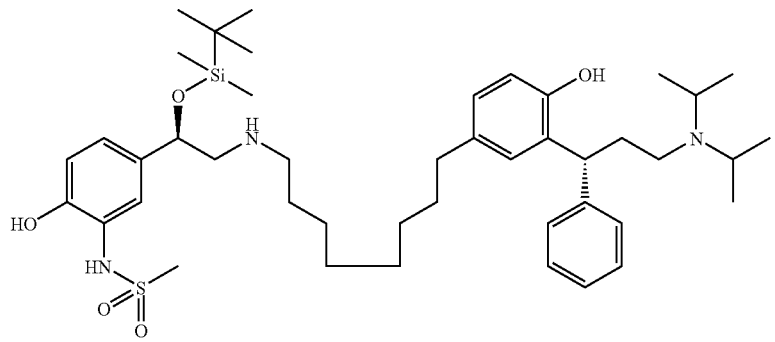

N-[2-(benzyloxy)-5-{(1R)-1-{[tert-butyl(dimethyl)silyl]oxy}-2-[(8-{3-[(1R)-3-(diisopropylamino)-1-phenylpropyl]-4-hydroxyphenyl}octyl)amino]ethyl}phenyl]methanesulfonamide (Preparation 54, 90 mg, 0.10 mmol), ammonium formate (130 mg, 2.0 mmol) and 20% palladium hydroxide on carbon (20 mg) were mixed in ethanol (3 ml) and heated to 70° C. overnight. Reaction mixture was then cooled and filtered. The filtrate was collected and the solvent removed in vacuo. The residue was purified by column chromatography on silica gel eluting with dichloromethane:methanol:880 ammonia (98/2/0.2 to 91/9/0.9 by volume) to furnish the title compound as a gum to furnish the title compound as a glass, 82 mg.

LRMS: m/z 783 [M+H]+.

Preparation 56 tert-butyl{2-[4-(pent-4-en-1-yloxy)phenyl]ethyl}carbamate

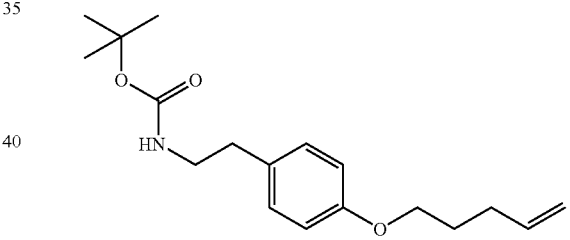

tert-butyl[2-(4-hydroxyphenyl)ethyl]carbamate (Prepared according to Journal of Organic Chemistry 1999, 64, 1074, 1.0 g, 4.21 mmol) was dissolved in dimethylformamide (8 ml) and potassium carbonate (1.2 g, 8.4 mmol) was added, followed 15 minutes later by 5-bromopent-1-ene (0.99 ml, 8.4 mmol), and the mixture stirred at 60° C. overnight.

After cooling to room temperature, water was added and extracted with diethyl ether, dried (magnesium sulphate) and the solvent removed in vacuo, to yield the title compound as a white solid, 1.2 g.

LRMS: m/z 328 [M+Na]+.

Preparation 57 tert-butyl[2-(4-{[(4E)-5-{4-(benzyloxy)-3-[(1R)-3-(diisopropylamino)-1-phenylpropyl]phenyl}pent-4-en-1-yl]oxy}phenyl)ethyl]carbamate

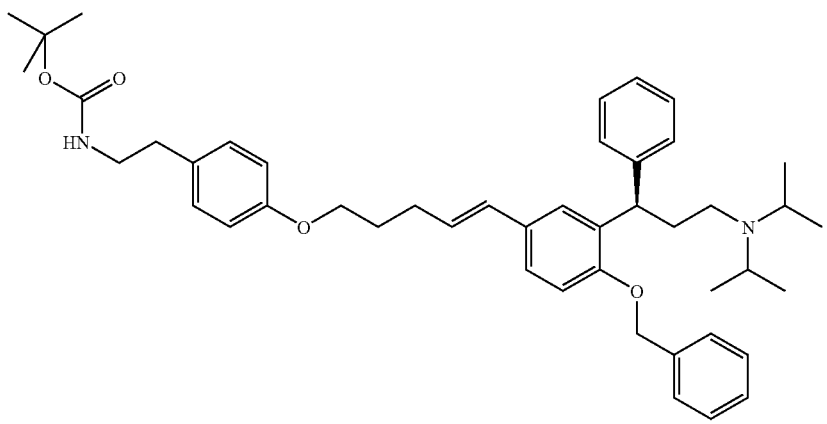

tert-butyl{2-[4-(pent-4-en-1-yloxy)phenyl]ethyl}carbamate (Preparation 56, 1.2 g, 3.9 mmol), (3R)-3-[2-(benzyloxy)-5-bromophenyl]-N,N-diisopropyl-3-phenyl-propan-1-amine (Prepared according to WO9411337, 1.9 g, 3.9 mmol), palladium acetate (90 mg, 0.4 mmol), tri(o-tolyl) phosphine (200 mg, 0.8 mmol), and diisopropylethylamine (1.0 ml, 5.9 mmol) were mixed in acetonitrile (12 ml), degassed with argon and the heated to 90° C. for 5 hours. The reaction was cooled to room temperature, filtered through Arbocel and solvent removed in vacuo. The residue was taken up in water and ethyl acetate, the organics were separated, dried (magnesium sulphate) and the solvent removed in vacuo, the residue was purified by column chromatography on silica gel eluting with dichloromethane:methanol:880 ammonia (98:2:0.2 to 95:15:1.5 by volume) to furnish the title compound as a pale yellow foam, 2.5 g.

LRMS: m/z 705 [M+H]+.

Preparation 58 tert-butyl(2-{4-[(5-{3-[(1R)-3-(diisopropylamino)-1-phenylpropyl]-4-hydroxyphenyl}pentyl)oxy]phenyl}ethyl)carbamate

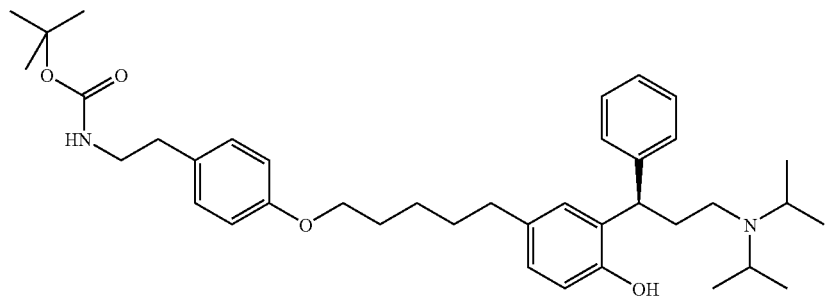

Tert-butyl[2-(4-{[(4E)-5-{4-(benzyloxy)-3-[(1R)-3-(diisopropylamino)-1-phenylpropyl]phenyl}pent-4-en-1-yl]oxy}phenyl)ethyl]carbamate (Preparation 57, 2.5 g, 3.5 mmol) was dissolved in ethanol (50 ml) and palladium hydroxide (20% by weight on carbon, 600 mg, 0.84 mmol) and ammonium formate (2.0 g, 30 mmol) were added and stirred at 90° C. for 1 hour. Reaction was cooled and filtered through arbocel and the solvent removed in vacuo. The residue was purified by column chromatography on silica gel eluting with dichloromethane:methanol:880 ammonia (95/5/0.5 to 90/10/1 by volume) to furnish the title compound as a white foam, 1.66 g LRMS: m/z 617 [M+H]+.

Preparation 59

4-{5-[4-(2-aminoethyl)phenoxy]pentyl}-2-[(1R)-3-(diisopropylamino)-1-phenylpropyl]phenol bis hydrochloride salt

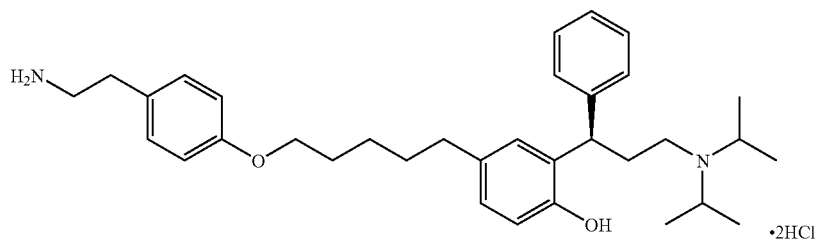

Tert-butyl(2-{4-[(5-{3-[(1R)-3-(diisopropylamino)-1-phenylpropyl]-4-hydroxyphenyl}pentyl)oxy]phenyl}ethyl)carbamate (Preparation 58, 1.66 g, 2.69 mmol) was dissolved in dichloromethane (20 ml) and ethanol (3 ml) and hydrochloric acid (12 ml of a 2M solution in diethyl ether) was added, and the mixture stirred overnight at room temperature. Solvent was removed in vacuo and the residue dissolved in dichloromethane and solvent removed in vacuo again to furnish the title compound as a yellow foam, 1.6 g LRMS: m/z 517 [M+H]+.

Preparation 60

N-[2-(benzyloxy)-5-{(1R)-1-{[tert-butyl(dimethyl)silyl]oxy}-2-[(2-{4-[(5-{3-[(1R)-3-(diisopropylamino)-1-phenylpropyl]-4-hydroxyphenyl}pentyl)oxy]phenyl}ethyl)amino]ethyl}phenyl]methanesulfonamide

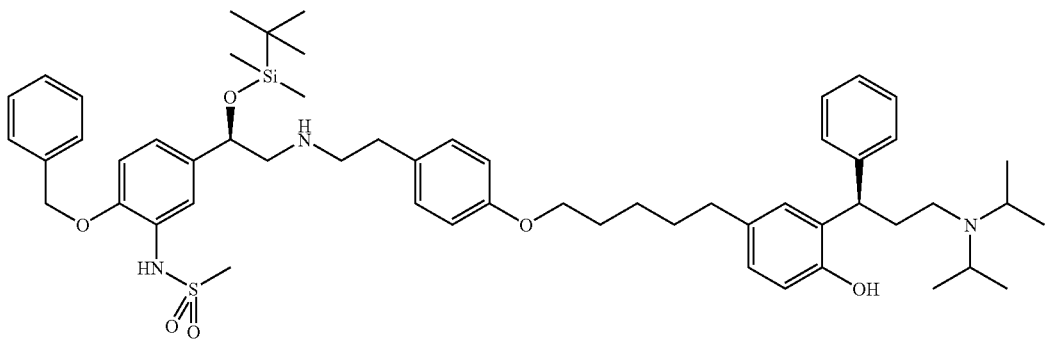

4-{5-[4-(2-aminoethyl)phenoxy]pentyl}-2-[(1R)-3-(diisopropylamino)-1-phenylpropyl]phenol bis hydrochloride salt (Preparation 59, 400 mg, 0.68 mmol) was dissolved in water and basified with saturated aqueous sodium hydrogen carbonate, then extracted with dichloromethane. Organics were dried (magnesium sulphate) and solvent removed in vacuo. The residue was dissolved in dimethylsulfoxide (0.3 ml) and N-{2-(benzyloxy)-5-[(1R)-2-bromo-1-{[tert-butyl(dimethyl)silyl]oxy}ethyl]phenyl}methanesulfonamide (Prepared according to WO2005/080324, 400 mg, 0.8 mmol) added, and heated in a sealed vessel at 80° C. for 6 hours.

After cooling to room temperature, water was added, extracted with dichloromethane, dried (magnesium sulphate) and solvent removed in vacuo. The residue was purified by column chromatography on silica gel eluting with dichloromethane:methanol:880 ammonia (9515/0.5 by volume) to furnish the title compound, 370 mg.

LRMS: m/z 948 [M+H]+.

Preparation 61

N-(5-{(1R)-1-{[tert-butyl(dimethyl)silyl]oxy}-2-[(2-{4-[(5-{3-[(1R)-3-(diisopropylamino)-1-phenylpropyl]-4-hydroxyphenyl}pentyl)oxy]phenyl}ethyl)amino]ethyl}-2-hydroxyphenyl)methanesulfonamide

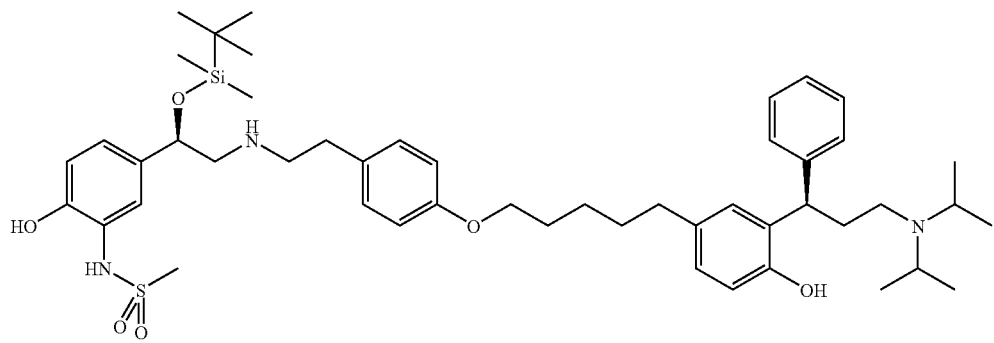

N-[2-(benzyloxy)-5-{(1R)-1-{[tert-butyl(dimethyl)silyl]oxy}-2-[(2-{4-[(5-{3-[(1R)-3-(diisopropylamino)-1-phenylpropyl]-4-hydroxyphenyl}pentyl)oxy]phenyl}ethyl)amino]ethyl}phenyl]methanesulfonamide (Preparation 60, 350 mg, 0.37 mmol) was dissolved in ethanol (10 ml) and ammonium formate (1.0 g, 16 mmol) and 20% palladium hydroxide on carbon (250 mg) were added and heated to 90° C. for 1 hour. Reaction mixture was then cooled and filtered through Arbocel and the solvent removed in vacuo to furnish the title compound as a colourless oil, 250 mg.

LRMS: m/z 858 [M+H]+.

Preparation 62

4-{4-[4-(2-{[(2R)-2-[4-(benzyloxy)-3-(hydroxymethyl)phenyl]-2-{[tert-butyl(dimethyl)silyl]oxy}ethyl]amino}ethyl)phenoxy]butyl}-2-[(1R)-3-(diisopropylamino)-1-phenylpropyl]phenol

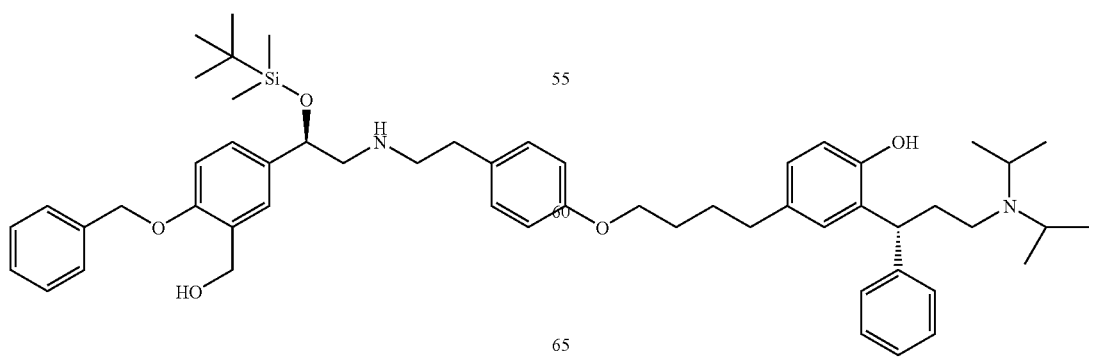

4-{4-[4-(2-aminoethyl)phenoxy]butyl}-2-[(1R)-3-(diisopropylamino)-1-phenylpropyl]phenol tert-butyl{2-[4-(4-{3-[(1R)-3-(diisopropylamino)-1-phenylpropyl]-4-hydroxyphenyl}butoxy)phenyl]ethyl}carbamate bis hydrochloride salt (Preparation 13, 1.30 g, 2.26 mmol), was dissolved in a mixture of saturated aqueous sodium hydrogen carbonate and dichloromethane. The organic layer was separated, dried (magnesium sulphate) and the solvent removed in vacuo The residue was dissolved in acetonitrile (10 ml) and {2-(benzyloxy)-5-[(1R)-2-bromo-1-{[tert-butyl(dimethyl)silyl]oxy}ethyl]phenyl}methanol (Prepared according to WO2004/032921, 1.02 mg, 2.26 mmol), sodium hydrogen carbonate (570 mg, 6.78 mmol) were added, and heated to 85° C. and stirred overnight. After cooling the solvent was removed in vacuo and the residue was dissolved in dichloromethane (30 ml) and washed with water (2×20 ml) then brine (20 ml), dried (magnesium sulphate) and the solvent removed in vacuo. The residue was purified by column chromatography on silica gel eluting with dichloromethane:methanol:880 ammonia (95/5/1 to 90/10/1 by volume) to furnish the title compound as a gum, 388 mg.

LRMS: m/z 874 [M+H]$^+$.

Preparation 63

4-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-(hydroxymethyl)phenol

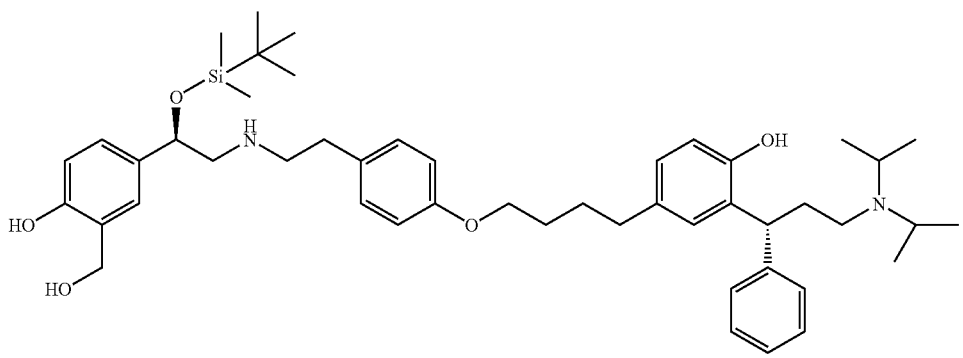

4-{4-[4-(2-{[(2R)-2-[4-(benzyloxy)-3-(hydroxymethyl)phenyl]-2-{[tert-butyl(dimethyl)silyl]oxy}ethyl]amino}ethyl)phenoxy]butyl}-2-[(1R)-3-(diisopropylamino)-1-phenylpropyl]phenol (Preparation 62, 388 mg, 0.44 mmol) was dissolved in ethanol (5 ml) and ammonium formate (280 mg, 4.44 mmol) and 20% palladium hydroxide on carbon (58 mg) added. The stirred reaction was heated at 85° C. for 18 hours. After cooling to room temperature, further ammonium formate (140 mg, 2.22 mmol) and 20% palladium hydroxide on carbon (20 mg) were added and mixture stirred at 85° C. for 3 hours. Reaction mixture was then cooled and filtered through Arbocel™, the filtrate was collected and the solvent removed in vacuo to furnish the title compound as a glass, 311 mg.

LRMS: m/z 784 [M+H]+.

Preparation 64 tert-butyl{2-[4-(2-{4-(benzyloxy)-3-[(1R)-3-(diisopropylamino)-1-phenylpropyl]phenyl}ethoxy)phenyl]-11-dimethylethyl}carbamate

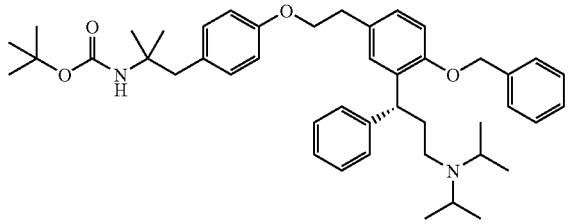

tert-butyl[2-(4-hydroxyphenyl)-1,1-dimethylethyl]carbamate (Prepared according to WO1997/34905, 1.5 g, 5.6 mmol), caesium carbonate (2.9 g, 9.0 mmol), sodium iodide (670 mg, 4.5 mmol) and 2-{4-(benzyloxy)-3-[(1R)-3-(diisopropylamino)-1-phenylpropyl]phenyl}ethyl methanesulfonate (Preparation 36, 2.4 g, 4.5 mmol) were mixed in toluene (18 ml) and stirred at 120° C. overnight. After cooling, water (100 ml) and ethyl actate (100 ml) were added, the aqueous layer was then separated and extracted with further ethyl actate (100 ml×2). The combined organics were then dried (magnesium sulphate) and the solvent removed in vacuo. The residue was purified by column chromatography on silica gel eluting with dichloromethane:methanol:880 ammonia (95/5/1 by volume) the appropriate fractions were isolated and the solvent removed in vacuo. The residue was dissolved in minimum volume of ethyl actate and pentane (100 ml) was added. The organics were then washed with aqueous NaOH (1N, 150 ml×2) then dried (magnesium sulphate) and the solvent removed in vacuo to yield the title compound as an oil, 1.72 g.

LRMS: m/z 694 [M+H]+.

Preparation 65

(3R)-3-[5-{2-[4-(2-amino-2-methylpropyl)phenoxy]ethyl}-2-(benzyloxy)phenyl]-NN-diisopropyl-3-phenylpropan-1-amine bis hydrochloride salt

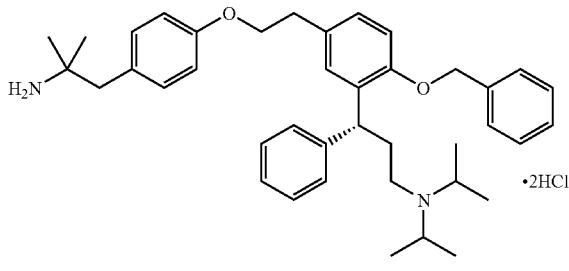

tert-butyl{2-[4-(2-{4-(benzyloxy)-3-[(1R)-3-(diisopropylamino)-1-phenylpropyl]phenyl}ethoxy)phenyl]-11-dimethylethyl}carbamate (Preparation 64, 1.72 g, 2.48 mmol) was treated with hydrochloric acid (4M in dioxan, 15 ml). After stirring over night at room temperature the solvent was removed in vacuo to yield the title compound as a colourless foam, 1.60 g LRMS: m/z 594 [M+H]+.

Preparation 66

8-(benzyloxy)-5-[(1R)-2-({2-[4-(2-{4-(benzyloxy)-3-[(1R)-3-(diisopropylamino)-1-phenylpropyl]phenyl}ethoxy)phenyl]-11-dimethylethyl}amino)-1-{[tert-butyl(dimethyl)silyl]oxy}ethyl]quinolin-2(1H)-one

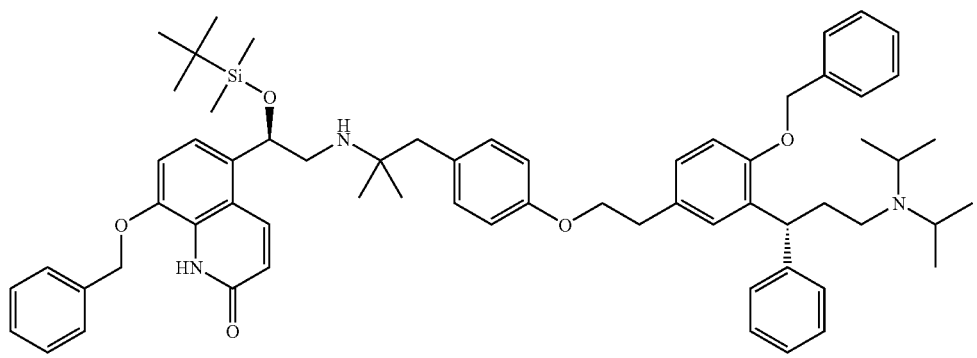

(3R)-3-[5-{2-[4-(2-amino-2-methylpropyl)phenoxy]ethyl}-2-(benzyloxy)phenyl]-NN-diisopropyl-3-phenylpropan-1-amine bis hydrochloride salt (Preparation 65, 550 mg, 0.83 mmol), 8-(benzyloxy)-5-[(1R)-2-bromo-1-{[tert-butyl(dimethyl)silyl]oxy}ethyl]quinolin-2(1H)-one (Prepared according to WO2005/092861, 405 mg, 0.83 mmol) and sodium hydrogen carbonate (244 mg, 2.9 mmol) were added to acetonitrile (6 ml) and stirred at 90° C. under nitrogen for 20 hours. The mixture was cooled and the solvent removed in vacuo. The residue was then partitioned between water (40 ml) and dichloromethane (40 ml), the layers separated and the aqueous layer extracted with further dichloromethane (40 ml). The combined organics were dried (magnesium sulphate) and the solvent removed in vacuo. The residue was purified by column chromatography on silica gel eluting with dichloromethane:methanol:880 ammonia (95/5/0.5 to 80/20/2 by volume) to furnish the title compound as a gum, 100 mg.

LRMS: m/z 999 [M−H]−.

Preparation 67

5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]-11-dimethylethyl}amino)ethyl]-8-hydroxyquinolin-2(1H)-one

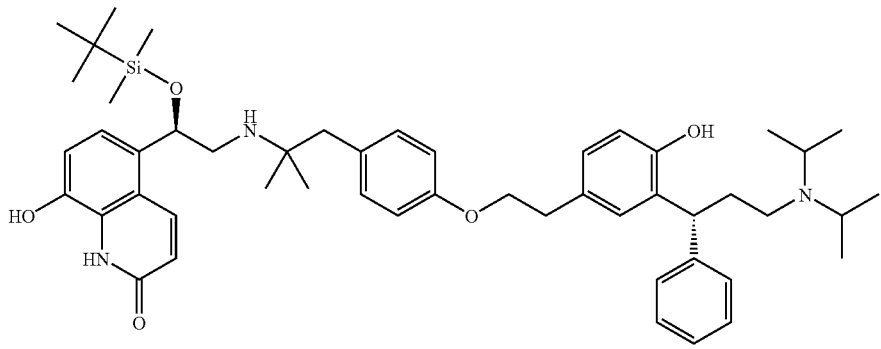

8-(benzyloxy)-5-[(1R)-2-({2-[4-(2-{4-(benzyloxy)-3-[(1R)-3-(diisopropylamino)-1-phenylpropyl]phenyl}ethoxy)phenyl]-11-dimethylethyl}amino)-1-{[tert-butyl(dimethyl)silyl]oxy}ethyl]quinolin-2(1H)-one (Preparation 66, 370 mg, 0.37 mmol), ammonium formate (234 mg, 3.7 mmol) and 20% palladium hydroxide on carbon (100 mg) were mixed in ethanol (5 ml) and heated to 85° C., under a nitrogen atmosphere, overnight. Reaction mixture was then cooled and filtered through Celite™ and the filtrate solvent removed in vacuo. The residue was purified by column chromatography on silica gel eluting with dichloromethane:methanol:880 ammonia (97.5/2.5/0.25 to 95/5/0.5 by volume) to furnish the title compound as a gum, 160 mg.

LRMS: m/z 821 [M+H]+.

EXAMPLE 1

N-(5-{(1R)-2-[(10-{3-[(1R)-3-(diisopropylamino)-1-phenylpropyl]-4-hydroxyphenyl}decyl)amino]-1-hydroxyethyl}-2-hydroxyphenyl)methanesulfonamide Palladium hydroxide (10% on carbon, 20 mg) was added to a stirred solution of ammonium formate (344 mg, 5.46 mmol) and N-{2-(benzyloxy)-5-[(1R)-2-{[10-{4-(benzyloxy)-3-[(1R)-3-(diisopropylamino)-1-phenylpropyl]phenyl}dec-9-en-1-yl]amino}-1-{[tert-butyl(dimethyl)silyl]oxy}ethyl]phenyl}methanesulfonamide (Preparation 4, 90 mg, 0.091 mmol) in methanol (10 ml) at room temperature. The reaction was heated under reflux for 1 hour, cooled to room temperature and filtered through Arbocel™. The filtrate was collected and the solvent removed in vacuo to yield N-(5-{(1R)-1-{[tert-butyl(dimethyl)silyl]oxy}-2-[(10-{3-[(1R)-3-(diisopropylamino)-1-phenylpropyl]-4-hydroxyphenyl}decyl)amino]ethyl}-2-hydroxyphenyl)methanesulfonamide as a mixture with residual ammonium formate. LRMS: m/z 811 [M+H]⁺. This mixture was dissolved in tetrahydrofuran (4 ml) and methanol (2 ml) and triethylaminetrihydrofluoride (88 ul, 0.54 mmol) was added in one portion at room temperature. The reaction was stirred for 12 hours and the solvent removed under reduced pressure, the residue was dissolved in methanol (10 ml) and 880 ammonia (1 ml) and the solvent removed under reduced pressure. The residue was purified by column chromatography on silica gel eluting with dichloromethane:methanol:880 ammonia (80/20/2.0 by volume) to furnish the title compound as a glass, 35 mg.

LRMS: m/z 697 [M+H]⁺.

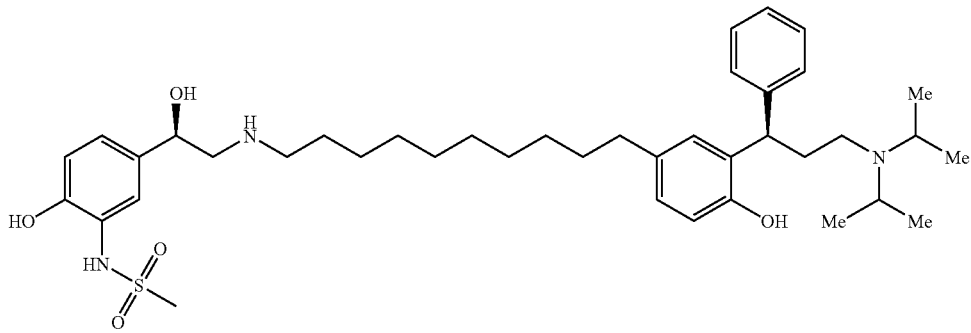

EXAMPLE 2

N-{5-[(1R)-2-({2-[4-(3-{3-[(1R)-3-(diisopropylamino)-1-phenylpropyl]-4-hydroxyphenyl}propoxy)phenyl]ethyl}amino)-1-hydroxyethyl]-2-hydroxyphenyl}methanesulfonamide

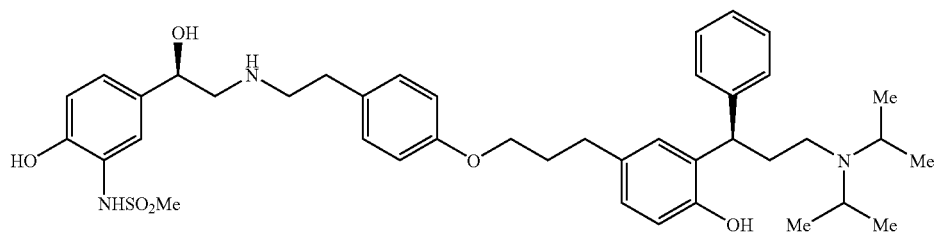

N-{5-[(1R)-1-{[tert-butyl(dimethyl)silyl]oxy}-2-({2-[4-(3-{3-[(1R)-3-(diisopropylamino)-1-phenylpropyl]-4-hydroxyphenyl}propoxy)phenyl]ethyl}amino)ethyl]-2-hydroxyphenyl}methanesulfonamide (Preparation 10, 98 mg, 0.11 mmol) was dissolved in tetrahydrofuran (4 ml) and methanol (2 ml) and triethylaminetrihydrofluoride (95 ul, 0.58 mmol) was added in one portion at room temperature. The reaction was stirred for 24 hours and the solvent removed under reduced pressure, the residue was dissolved in methanol (10 ml) and 880 ammonia (1 ml) and the solvent removed under reduced pressure to yield an off white solid. The solid was dissolved in methanol (1 ml) and precipitated with an excess of diisopropylether, the solid was collected by filtration to furnish the title compound as a white solid, 16 mg.

LRMS: m/z 718 [M+H]$^+$.

EXAMPLE 3

N-{5-[(1R)-2-({2-[4-(4-{3-[(1R)-3-(Diisopropylamino)-1-phenylpropyl]-4-hydroxyphenyl}butoxy)phenyl]ethyl}amino)-1-hydroxyethyl]-2-hydroxyphenyl}methanesulfonamide

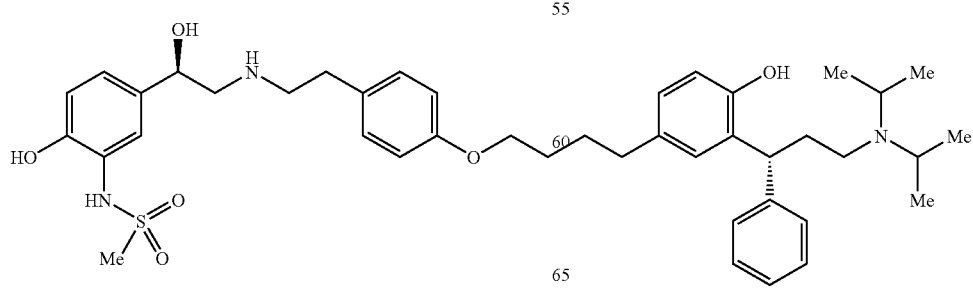

N-{5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-hydroxyphenyl}methanesulfonamide (Preparation 15, 190 mg, 0.22 mmol) was dissolved in tetrahydrofuran (5 ml) and N,N-diethylethanamine trihydrofluoride (0.2 ml, 1 mmol) was added dropwise. After 29 hours a mixture of tetrahydrofuran (5 ml) and 880 ammonia (5 ml) were added and after 15 minutes brine was added, the organic layer was separated, dried (magnesium sulphate), filtered, the solvents were removed in vacuo and the residue was purified by column chromatography on silica gel eluting with dichloromethane:methanol:880 ammonia (981210.2 to 92/8/0.8 by volume) to furnish the title compound as a white foam, 90 mg.

LRMS: m/z 732 [M+H]$^+$.

EXAMPLE 4

N-(5-{(1R)-2-[(7-{3-[(1R)-3-(diisopropylamino)-1-phenylpropyl]-4-hydroxyphenoxy}heptyl)amino]-1-hydroxyethyl}-2-hydroxyphenyl)methanesulfonamide

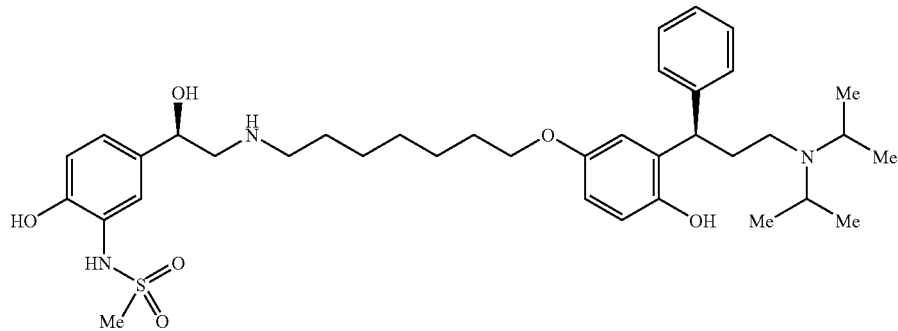

N-(5-{(1R)-1-{[tert-butyl(dimethyl)silyl]oxy}-2-[(7-{3-[(1R)-3-(diisopropylamino)-1-phenylpropyl]-4-hydroxyphenoxy}heptyl)amino]ethyl}-2-hydroxyphenyl)methanesulfonamide (Preparation 20, 68 mg, 0.087 mmol) was dissolved in tetrahydrofuran (3 ml) and N,N-diethylethanamine trihydrofluoride (71 µl, 0.43 mmol) was added dropwise. After 18 hours a mixture of methanol (4 ml) and 880 ammonia (8 ml) were added and after 15 minutes the solvent was removed in vacuo. The residue was dissolved in dichloromethane and the solvent removed in vacuo again and the residue was purified by column chromatography on silica gel eluting with dichloromethane:methanol:880 ammonia (97/310.3 to 88/12/1.2 by volume) to furnish the title compound as a white solid, 30 mg.

LRMS: m/z 670 [M+H]$^+$.

EXAMPLE 5

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide

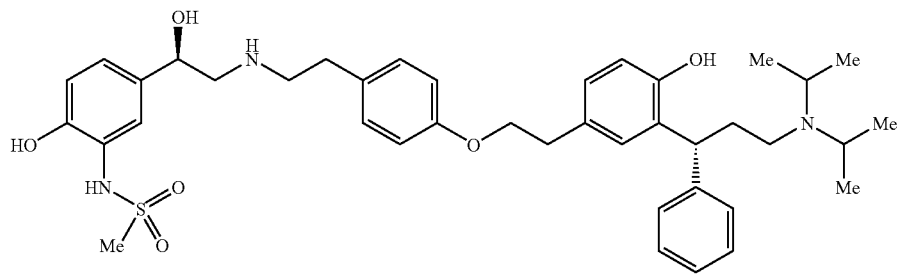

N-{2-(benzyloxy)-5-[(1R)-2-({2-[4-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanesulfonamide (Preparation 22, 78 mg, 0.078 mmol) was dissolved in ethanol (2 ml), ammonium formate (200 mg, 3.17 mmol) was added, heated to reflux then palladium hydroxide (20% by weight on carbon, 50 mg, 0.07 mmol) was added and after 30 minutes the reaction was cooled to room temperature and the mixture was filtered through Arbocel™ and the solvent removed in vacuo. The residue was dissolved in tetrahydrofuran (2 ml) and N,N-diethylethanamine trihydrofluoride (59 μl, 0.37 mmol) was added and after 1 drop of methanol was added and the reaction mixture was stirred over night. The solvent was removed in vacuo and the residue dissolved in 1:1 methanol/880 ammonia, the solvents removed in vacuo and this process was repeated 4 times. The residue was purified by column chromatography on silica gel eluting with dichloromethane:methanol:880 ammonia (230/20/2 to 90/10/1 by volume) to furnish the title compound as a white solid, 28 mg.
LRMS: m/z 704 [M+H]$^+$.

EXAMPLE 6

N-{5-[(1R)-2-{[6-(4-{3-[(1R)-3-(Diisopropylamino)-1-phenylpropyl]-4-hydroxyphenyl}butoxy)hexyl]amino}-1-hydroxyethyl]-2-hydroxyphenyl}methanesulfonamide

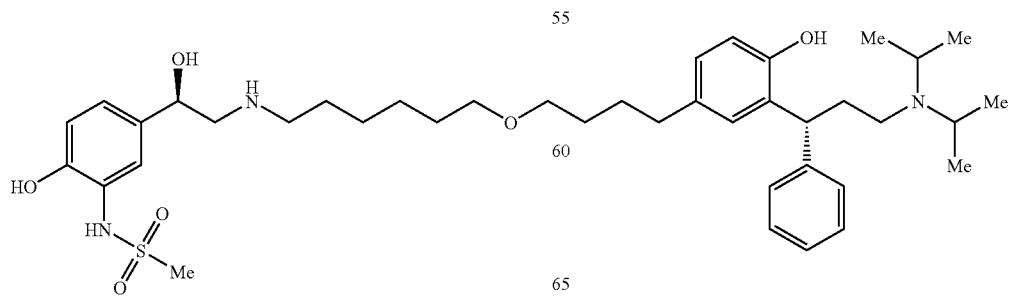

N-{5-[(1R)-1-{[tert-Butyl(dimethyl)silyl]oxy}-2-{[6-(4-{3-[(1R)-3-(diisopropylamino)-1-phenylpropyl]-4-hydroxyphenyl}butoxy)hexyl]amino}ethyl]-2-hydroxyphenyl}methanesulfonamide (Preparation 28, 420 mg, 0.51 mmol) was dissolved in tetrahydrofuran (6 ml) and triethylaminetrihydrofluoride (415 ul, 2.55 mmol) was added. The reaction was stirred at room temperature for 4 hours and the solvent removed in vacuo, the residue was dissolved in methanol (1 ml) and 880 ammonia (1 ml) and the solvent removed in vacuo, the residue was dissolved in methanol (1 ml) and 880 ammonia (1 ml) and the solvent removed in vacuo. The resulting oil was purified by column chromatography on silica gel eluting with dichloromethane:methanol:880 ammonia (89/11/1.1 by volume) to furnish the title compound as a yellow solid, 26 mg.

LRMS (ES): m/z 712 [M+H]$^+$.

EXAMPLE 7

N-{5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-2-hydroxyphenyl}formamide

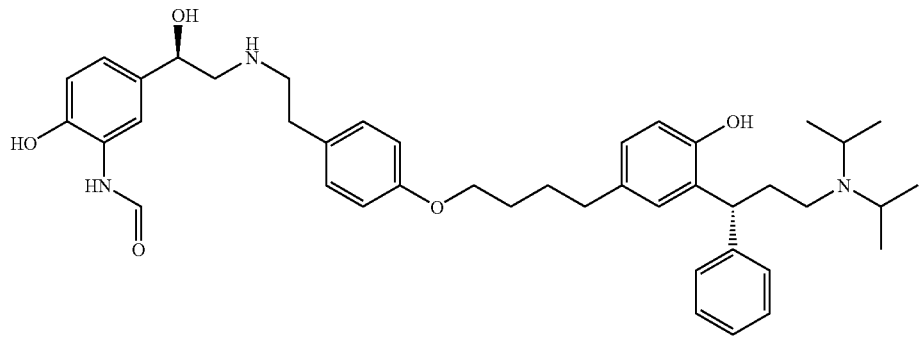

N-{5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-hydroxyphenyl}formamide (Preparation 30, 280 mg, 0.35 mmol) was dissolved in tetrahydrofuran (5 ml) and triethylaminetrihydrofluoride (0.29 ml, 1.8 mmol) was added, and the mixture stirred overnight at room temperature. Tetrahydrofuran (6 ml) and 880 ammonia (6 ml) were then added, the mixture stirred for 20 minutes, organics were then separated and washed with saturated aqueous sodium hydrogen carbonate (10 ml), then brine (10 ml), then dried (magnesium sulphate) and the solvent removed in vacuo. The residue was purified by column chromatography on silica gel eluting with dichloromethane:methanol:880 ammonia (98/2/0.2 to 88/12/1.2 by volume) to furnish the title compound as an off-white solid, 74 mg.

LRMS: m/z 683 [M+H]$^+$.

EXAMPLE 8

5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-8-hydroxyquinolin-2(1H)-one

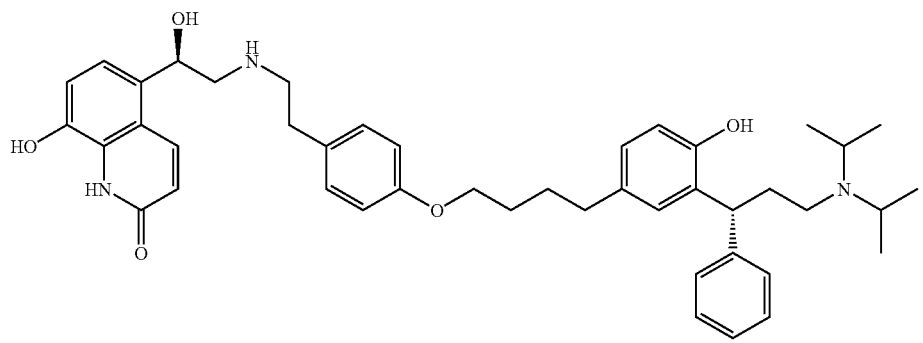

5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-8-hydroxyquinolin-2(1H)-one (Preparation 32, 305 mg, 0.37 mmol) was dissolved in tetrahydrofuran (5 ml) and triethylaminetrihydrofluoride (0.30 ml, 1.9 mmol) was added, and the mixture stirred overnight at room temperature. Tetrahydrofuran (6 ml) and 880 ammonia (6 ml) were then added, the mixture stirred for 20 minutes, organics were then separated and washed with saturated aqueous sodium hydrogen carbonate (10 ml), then brine (10 ml), then dried (magnesium sulphate) and the solvent removed in vacuo. The residue was purified by column chromatography on silica gel eluting with dichloromethane:methanol:880 ammonia (98/2/0.2 to 88/12/1.2 by volume) to furnish the title compound as a yellow solid, 99 mg.

LRMS: m/z 707 [M+H]$^+$.

EXAMPLE 9

5-[(1R)-1-{[hydroxy}-2-({2-[4-(4-{3-[(1R)-3-(diisopropylamino)-1-phenylpropyl]-4-hydroxyphenyl}butoxy)phenyl]ethyl}amino)ethyl]benzene-1,3-diol

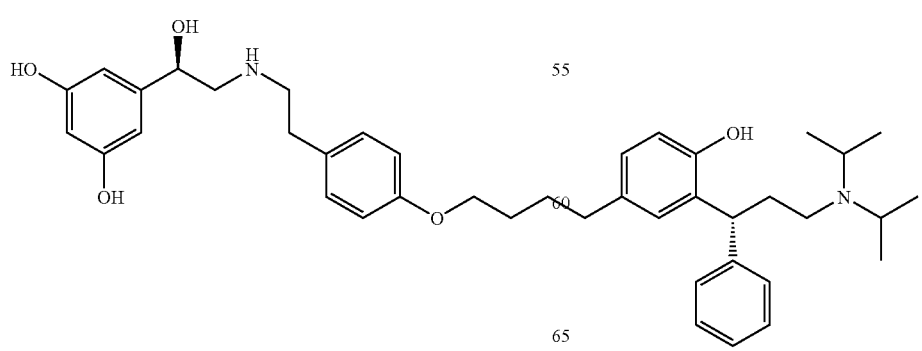

5-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]benzene-1,3-diol (Preparation 34, 555 mg, 0.72 mmol) was dissolved in tetrahydrofuran (8 ml) and triethylaminetrihydrofluoride (0.59 ml, 3.6 mmol) was added, and the mixture stirred overnight at room temperature. Tetrahydrofuran (6 ml) and 880 ammonia (6 ml) were then added, the mixture stirred for 20 minutes, organics were then separated and washed with saturated aqueous sodium hydrogen carbonate (10 ml), then brine (10 ml), then dried (magnesium sulphate) and the solvent removed in vacuo. The residue was purified by column chromatography on silica gel eluting with dichloromethane:methanol:880 ammonia (9812/0.2 to 88/12/1.2 by volume) to furnish the title compound as a white solid, 54 mg.

LRMS: m/z 655 [M+H]+.

EXAMPLE 10

N-{5-[(1R)-2-({2-[3-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide

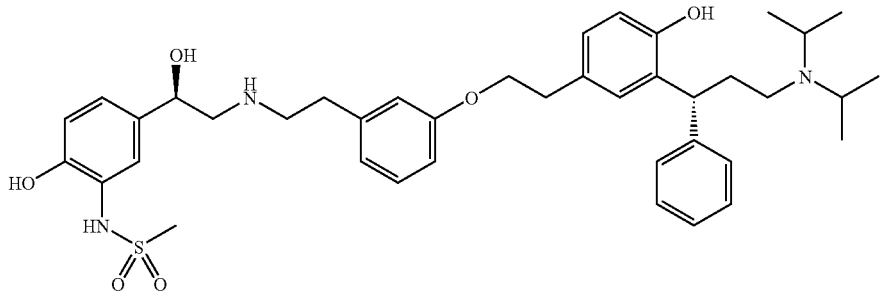

N-{2-(benzyloxy)-5-[(1R)-2-({2-[3-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanesulfonamide (Preparation 39, 257 mg, 0.26 mmol) was dissolved in ethanol (20 ml) and ammonium formate (325 mg, 5.15 mmol) and 20% palladium hydroxide on carbon (36 mg) were added. The stirred reaction was heated at 90° C., after 2 hours further ammonium formate (325 mg, 5.15 mmol) and 20% palladium hydroxide on carbon (36 mg) were added and mixture stirred at 90° C. for further 2 hours. After cooling to room temperature, mixture was filtered and solvent removed in vacuo, ethanol (20 ml), ammonium formate (325 mg, 5.15 mmol) and 20% palladium hydroxide on carbon (36 mg) were then added, and the mixture heated to 90° C. for a further 2 hours. After cooling, the mixture was filtered and solvent removed in vacuo. The residue was dissolved in methanol (10 ml) and tetrahydrofuran (20 ml), and triethylaminetrihydrofluoride (0.25 ml, 1.5 mmol) added. The mixture was stirred overnight and then the solvent removed in vacuo. The residue was dissolved in methanol (10 ml) and 880 ammonia (1 ml) and the solvent removed under reduced pressure. This was repeated and the residue was purified by column chromatography on silica gel eluting with dichloromethane:methanol:880 ammonia (99/1/0.1 to 80/20/2.0 by volume) to furnish, following trituration in diisopropyl ether, the title compound as a white solid, 52 mg.

LRMS: m/z 704 [M+H]+.

EXAMPLE 11

2-[(1R)-3-(diisopropylamino)-1-phenylpropyl]-4-(2-{3-[2-({(2R)-2-hydroxy-2-[4-hydroxy-3-(hydroxymethyl)phenyl]ethyl}amino)ethyl]phenoxy}ethyl)phenol

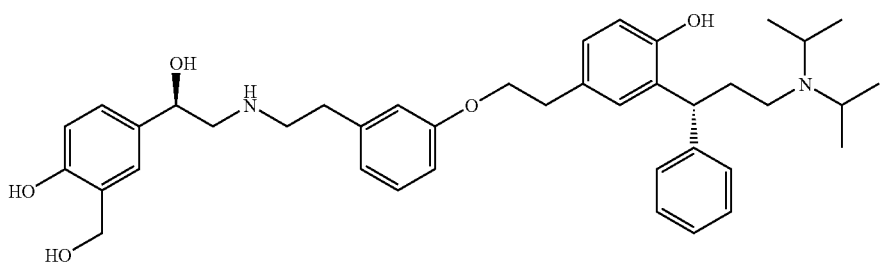

{2-(benzyloxy)-5-[(1R)-2-({2-[3-(2-{4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]phenyl}methanol (Preparation 40, 450 mg, 0.48 mmol), ammonium formate (610 mg, 9.6 mmol) and 20% palladium hydroxide on carbon (68 mg) were stirred in ethanol at 90° C. for 30 minutes. Further ammonium formate (610 mg, 9.6 mmol) and 20% palladium hydroxide on carbon (70 mg) were added and mixture stirred at 90° C. for further 30 minutes. Mixture cooled to room temperature and stirred overnight, then further ammonium formate (610 mg, 9.6 mmol) and 20% palladium hydroxide on carbon (70 mg) were added, before stirring at 90° C. for 1 hour. After cooling, the mixture was filtered and solvent removed in vacuo. Methanol (10 ml), tetrahydrofuran (20 ml) and triethylaminetrihydrofluoride (0.47 ml, 2.9 mmol) were added and mixture stirred for 3 days at room temperature. The solvent was removed in vacuo and the residue was dissolved in methanol (10 ml) and 880 ammonia (1 ml) and the solvent removed under reduced pressure. This was repeated and the residue was purified by column chromatography on silica gel eluting with dichloromethane:methanol:880 ammonia (99/1/0.1 to 80/20/2.0 by volume) to furnish, following trituration with diisopropyl ether, the title compound as a white solid, 95 mg.

LRMS: m/z 641 [M+H]$^+$.

EXAMPLE 12

5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]benzene-1,3-diol

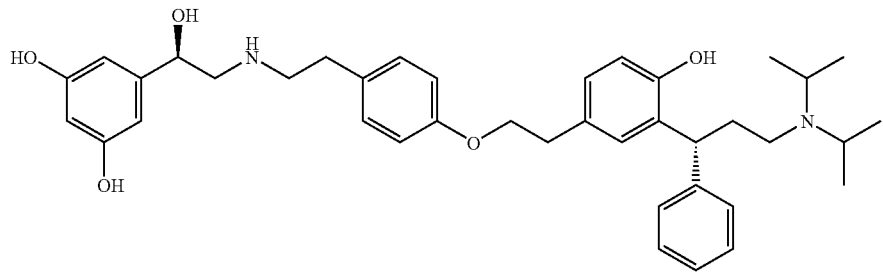

5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]benzene-1,3-diol (Preparation 44, 174 mg, 0.23 mmol) was dissolved in methanol (5 ml) and tetrahydrofuran (10 ml), and triethylaminetrihydrofluoride (0.23 ml, 1.4 mmol) added. The mixture was stirred overnight and then the solvent removed in vacuo. The residue was dissolved in methanol (10 ml) and 880 ammonia (1 ml) and the solvent removed under reduced pressure. This was repeated and the residue was purified by column chromatography on silica gel eluting with dichloromethane:methanol:880 ammonia (95/5/0.5 to 80/20/2.0 by volume) to furnish the title compound as a foam, 83 mg.

LRMS: m/z 627 [M+H]$^+$.

EXAMPLE 13

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}formamide

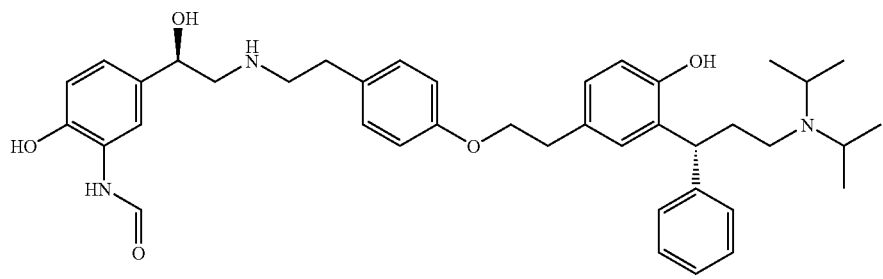

N-{5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]-2-hydroxyphenyl}formamide (Preparation 46, 180 mg, 0.18 mmol) was dissolved in methanol (5 ml) and tetrahydrofuran (10 ml), and triethylaminetrihydrofluoride (0.18 ml, 1.1 mmol) added. The mixture was stirred overnight and then the solvent removed in vacuo. The residue was dissolved in methanol (10 ml) and 880 ammonia (1 ml) and the solvent removed under reduced pressure. This was repeated and the residue was purified by column chromatography on silica gel eluting with dichloromethane:methanol:880 ammonia (98/2/0.2 to 80/20/2.0 by volume) to furnish the title compound as a gum, 69 mg.

LRMS: m/z 654 [M+H]$^+$.

EXAMPLE 14

5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-8-hydroxyquinolin-2(1H)-one

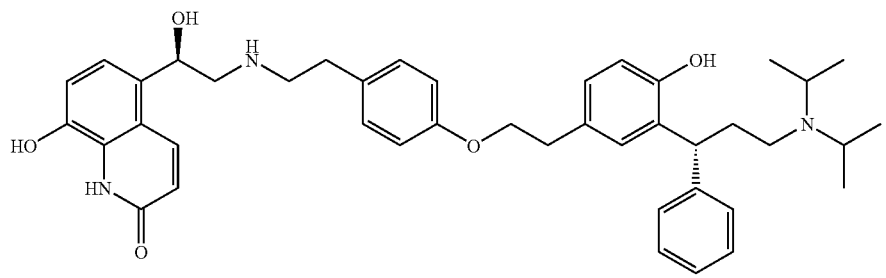

8-(benzyloxy)-5-[(1R)-2-({2-[4-(2-(4-(benzyloxy)-3-[(1R)-3-(diisopropylamino)-1-phenylpropyl]phenyl}ethoxy)phenyl]ethyl}amino)-1-{[tert-butyl(dimethyl)silyl]oxy}ethyl]quinolin-2(1H)-one (Preparation 47, 295 mg, 0.30 mmol) was dissolved in methanol (30 ml) and ammonium formate (380 mg, 6.1 mmol) and 20% palladium hydroxide on carbon (43 mg) added.

The stirred reaction was then heated at 90° C. for 2 hours. After cooling to room temperature, mixture was filtered and solvent removed in vacuo. The residue was then taken up in ethyl acetate (50 ml) and saturated aqueous sodium hydrogen carbonate (50 ml). The organics were separated, washed with brine then dried (magnesium sulphate) and the solvent removed in vacuo. The residue was then dissolved in methanol (10 ml) and tetrahydrofuran (20 ml), and triethylaminetrihydrofluoride (0.30 ml, 1.8 mmol) added. The mixture was stirred overnight and then the solvent removed in vacuo. The residue was dissolved in methanol (20 ml) and 880 ammonia (2 ml) and the solvent removed under reduced pressure. This was repeated and the residue was purified by column chromatography on silica gel eluting with dichloromethane:methanol:880 ammonia (98/2/0.2 to 80/20/2.0 by volume) to furnish the title compound as a yellowish foam, 137 mg.

LRMS: m/z 678 [M+H]+.

EXAMPLE 15

2-[(1R)-3-(diisopropylamino)-1-phenylpropyl]-4-(2-{4-[2-({(2R)-2-hydroxy-2-[4-hydroxy-3-(hydroxymethyl)phenyl]ethyl}amino)ethyl]phenoxy}ethyl)phenol

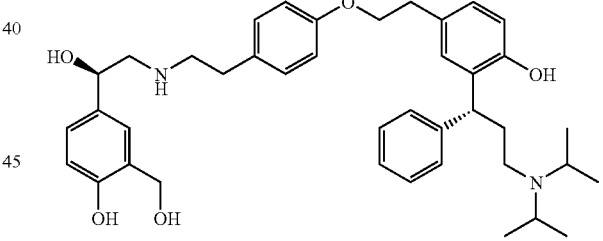

4-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]ethyl}amino)ethyl]-2-(hydroxymethyl)phenol (Preparation 49, 235 mg, 0.30 mmol) was dissolved in methanol (2.9 ml) and water (1.4 ml) and ammonium fluoride (112 mg, 3.0 mmol) was added. The reaction was heated to 40° C. and stirred overnight, cooled to room temperature and then saturated aqueous sodium hydrogen carbonate (20 ml) and ethyl acetate (20 ml) were added. The aqueous was separated and extracted with ethyl acetate and the combined organics dried (magnesium sulphate) and the solvent removed in vacuo. The residue was purified by column chromatography on silica gel eluting with dichloromethane:methanol:880 ammonia (80/20/1.0 by volume) to furnish the title compound as a glass, 55 mg.

LRMS: m/z 641 [M+H]+.

EXAMPLE 16

N-(5-{(1R)-2-[(8-{3-[(1R)-3-(diisopropylamino)-1-phenylpropyl]-4-hydroxyphenyl}octyl)amino]-1-hydroxyethyl}-2-hydroxyphenyl)methanesulfonamide

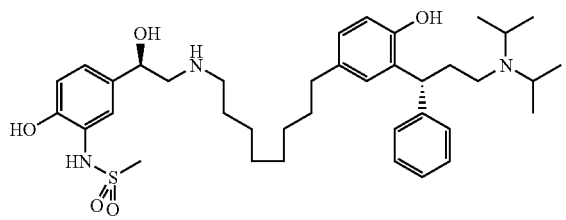

N-(5-{(1R)-1-{[tert-butyl(dimethyl)silyl]oxy}-2-[(8-{3-[(1R)-3-(diisopropylamino)-1-phenylpropyl]-4-hydroxyphenyl}octyl)amino]ethyl}-2-hydroxyphenyl)methanesulfonamide (Preparation 55, 74 mg, 0.095 mmol) was dissolved in tetrahydrofuran (3 ml) and triethylaminetrihydrofluoride (90 ul, 0.54 mmol) was added in one portion at room temperature. The reaction was stirred for 12 hours and the solvent removed under reduced pressure, the residue was dissolved in methanol (10 ml) and 880 ammonia (1 ml) and the solvent removed under reduced pressure. The residue was purified by column chromatography on silica gel eluting with dichloromethane:methanol:880 ammonia (97/3/0.3 to 85/15/1.5 by volume) to furnish the title compound as a yellow solid, 34 mg.

LRMS: m/z 668 [M+H]$^+$.

EXAMPLE 17

N-(5-{(1R)-2-[(2-{4-[(5-{3-[(1R)-3-(diisopropylamino)-1-phenylpropyl]-4-hydroxyphenyl}pentyl)oxy]phenyl}ethyl)amino]-1-hydroxyethyl}-2-hydroxyphenyl)methanesulfonamide

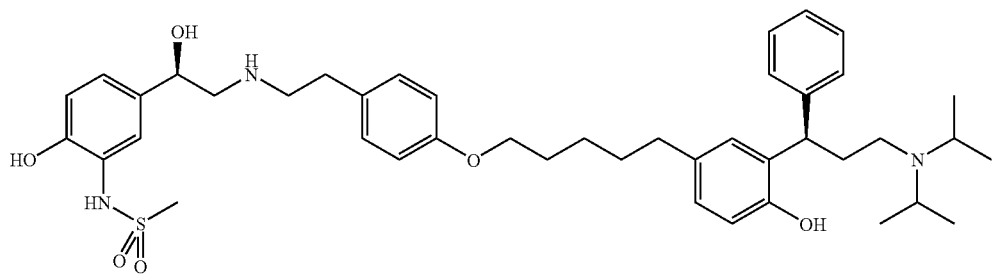

N-(5-{(1R)-1-{[tert-butyl(dimethyl)silyl]oxy}-2-[(2-{4-[(5-{3-[(1R)-3-(diisopropylamino)-1-phenylpropyl]-4-hydroxyphenyl}pentyl)oxy]phenyl}ethyl)amino]ethyl}-2-hydroxyphenyl)methanesulfonamide (Preparation 61, 250 mg, 0.29 mmol) was dissolved in tetrahydrofuran (10 ml) and methanol (0.5 ml) and triethylaminetrihydrofluoride (1.0 ml, 6.1 mmol) was added. The reaction was stirred for 3 days and the solvent removed in vacuo. The residue was dissolved in 880 ammonia (1 ml) and the solvent removed under reduced pressure, this was repeated 3 times. The residue was purified by column chromatography on silica gel eluting with dichloromethane:methanol:880 ammonia (95/5/0.5 by volume) to furnish the title compound as a pale yellow foam, 100 mg.

LRMS: m/z 746 [M+H]$^+$.

EXAMPLE 18

2-[(1R)-3-(diisopropylamino)-1-phenylpropyl]-4-(4-{4-[2-({(2R)-2-hydroxy-2-[4-hydroxy-3-(hydroxymethyl)phenyl]ethyl}amino)ethyl]phenoxy}butyl)phenol

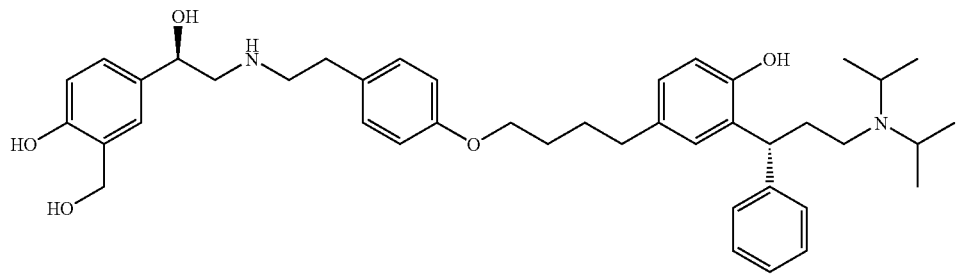

4-[(1R)-1-{[tert-butyl(dimethyl)silyl]oxy}-2-({2-[4-(4-{3-[(1R)-3-(diisopropylamino)-1-phenylpropyl]-4-hydroxyphenyl}butoxy)phenyl]ethyl}amino)ethyl]-2-(hydroxymethyl)phenol (Preparation 63, 311 mg, 0.356 mmol) was dissolved in methanol (4 ml) and water (0.5 ml) and ammonium fluoride (132 mg, 3.56 mmol) was added. The reaction was heated to 40° C. and stirred overnight. Reaction mixture was cooled and solvent removed in vacuo. The residue was purified by column chromatography on silica gel eluting with dichloromethane:methanol:880 ammonia (100/0/0 to 90/10/1.0 by volume) to furnish the title compound as a glass, 84 mg.

LRMS: m/z 669 [M+H]$^+$.

EXAMPLE 19

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide succinate salt

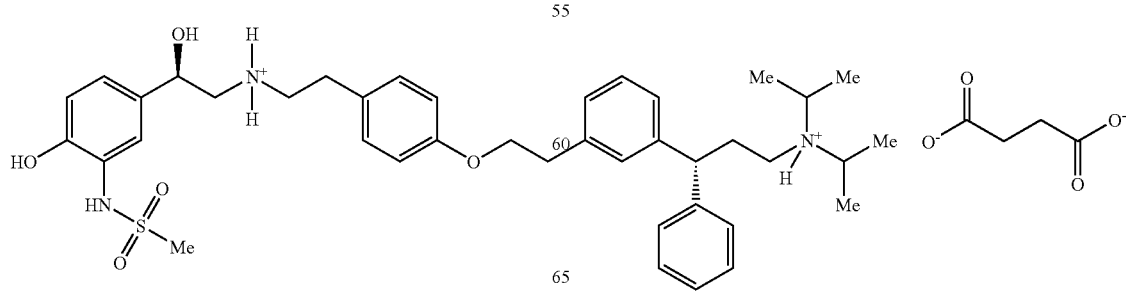

N-{5-[(1R)-2-({2-[4-(2-{3-[(1R)-3-(diisopropylamino)-1-phenylpropyl]-4-hydroxyphenyl}ethoxy)phenyl]ethyl}amino)-1-hydroxyethyl]-2-hydroxyphenyl}methanesulfonamide (Example 5, 2000 mg, 2.84 mmol) was dissolved in methanol (8 ml) and succinic acid (336 mg, 2.84 mmol) in water (2 ml) and methanol (2 ml) was added in one portion to the stirred solution at room temperature. Further water was added until the salt appeared as a gum which was seeded with a small crystal of the salt previously isolated. The mixture was left overnight and stirred occasionally to aid crystallisation. After 5 days the solid was filtered and dried in vacuo to furnish the title compound as a white crystalline solid, 2336 mg, m.p. 148-150° C.

LRMS: m/z 704 [M+H]$^+$.

EXAMPLE 20

5-[(1R)-2-({2-[4-(2-{3-[(1R)-3-(diisopropylamino)-1-phenylpropyl]-4-hydroxyphenyl}ethoxy)phenyl]-11-dimethylethyl}amino)-1-hydroxyethyl]-8-hydroxyquinolin-2(1H)-one

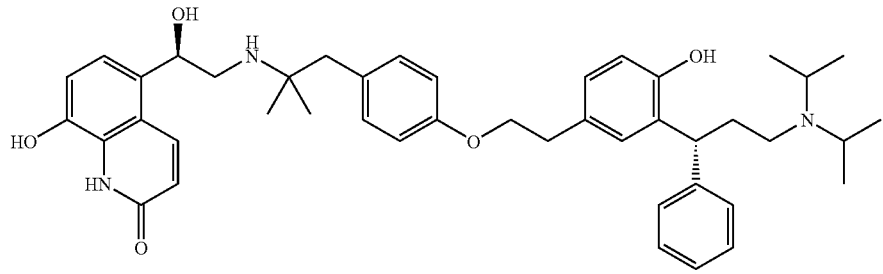

5-[(1R)-1-{[tert-butyl(dimethyl)silyl]oxy}-2-({2-[4-(2-{3-[(1R)-3-(diisopropylamino)-1-phenylpropyl]-4-hydroxyphenyl}ethoxy)phenyl]-11-dimethylethyl}amino)ethyl]-8-hydroxyquinolin-2(1H)-one (Preparation 67, 160 mg, 0.20 mmol) was dissolved in methanol (20 ml) and water (10 ml) and ammonium fluoride (740 mg, 3.6 mmol) was added. The reaction was heated to 40° C. and stirred, under a nitrogen atmosphere, for 21 hours. Reaction mixture was cooled and solvent removed in vacuo. The residue azetroped from toluene then dichloromethane to give a white solid which was purified by column chromatography on silica gel eluting with dichloromethane:methanol:880 ammonia (90/10/1 to 80/20/2 by volume) to furnish the title compound as a glass, 19 mg.

LRMS: m/z 707 [M+H]$^+$.

Functional Assessment of Antagonist Activity Using a Whole Cell β-Lactamase Reporter Assay in CHO Cells Expressing the hM$_3$ Receptor.

Cell Culture

CHO (Chinese Hamster Ovary) cells recombinantly expressing the human muscarinic M$_3$ receptor were transfected with the NFAT_β-Lac_Zeo plasmid. Cells were grown in DMEM with Glutamax-1, supplemented with 25 mM HEPES(Life Technologies 32430-027), containing 10% FCS (Foetal Calf Serum; Sigma F-7524), 1 nM Sodium pyruvate (Sigma S-8636), NEAA (non-Essential Amino Acids; Invitrogen 11140-035) and 200 1g/ml Zeocin (Invitrogen R250-01).

hM3 β-Lac Assay Protocol

Cells were harvested for assay when they reached 80-90% confluency using enzyme free cell Dissociation Solution (Life technologies 13151-014) incubated with the cells for 5 min at 37° C. in an atmosphere containing 5% $CO_2$. Detached cells were collected in warmed growth media and centrifuged at 200 rpm for 10 min, washed in PBS (Phosphate Buffered Saline; Life Technologies 14190-094) and centrifuged again as just described. The cells were re-suspended at $2 \times 10^5$ cells/ml in growth medium (composition as described above). 20 μl of this cell suspension was added to each well of a 384 well black clear bottomed plate (Greiner Bio One 781091-PFI). The assay buffer used was PBS supplemented with 0.05% Pluronic F-127 (Sigma 9003-11-6) and 2.5% DMSO. Muscarinic M$_3$ receptor signalling was stimulated using 80 nM carbamyl choline (Aldrich N240-9) incubated with the cells for 4 h at 37° C./5% $CO_2$ and monitored at the end of the incubation period using a Tecan SpectraFluor+plate reader (λ–excitation 405 nm, emission 450 nm and 503 nm). Compounds under test were added to the assay at the beginning of the 4 h incubation period and compound activity measured as the concentration dependent inhibition of the carbamyl choline induced signal. Inhibition curves were plotted and IC$_{50}$ values generated using a 4-parameter sigmoid fit and converted to Ki values using the Cheng-Prusoff correction and the K$_D$ value for carbamyl choline in the assay.

Functional Assessment of Agonist Potency and Efficacy Using a Whole Cell Luciferase Reporter Assay in CHO Cells Expressing the hB$_2$ Receptor.

Cell Culture

CHO (Chinese Hamster Ovary) cells recombinantly expressing the human adrenergic B$_2$ receptor and transfected with a luciferase enzyme reporter gene were maintained in growth media composed of F12:DMEM (Sigma D6421) containing 10% Foetal Bovine Serum (FBS: Sigma F03921) 10 μg/ml puromycin (Sigma N277698), 0.5 mg/ml Geneticin G418 (Sigma G7034) and 2 mM L-glutamine (Sigma G7513). The cells were kept in sterile conditions at 37° C., in an atmosphere containing 5% $CO_2$.

hB2 Luciferase Assay Protocol

Cells were harvested for assay when they reached 80-90% confluency using enzyme free cell Dissociation Solution (Life technologies 13151-014) incubated with the cells for 5 min at 37° C. in an atmosphere containing 5% $CO_2$. Detached cells were collected in warmed growth media (composition described above), and re-suspended in assay media (F12:DMEM (Sigma D6421) containing 1% Foetal Bovine Serum (FBS: Sigma F03921), 10 μg/ml puromycin (Sigma N277698), 0.5 mg/ml Geneticin G418 (Sigma G7034) and 2 mM L-glutamine (Sigma G7513))to give a viable cell concentration of 1×106 cells/ml. 10 ul of this suspension was added to each well of a tissue culture treated low volume 384 well plate (Greiner788073) and the plate incubated in an atmosphere containing 5% $CO_2$ at 37° C. for 2 h. Concentration ranges of test compounds were prepared in phosphate Buffered Saline containing 0.05% pluronic-F127 (Sigma P2443) and 2.5% DMSO. 2 μl of each test concentration were added to the appropriate 384 plate well and returned to the incubator for a further 4 h. At the end of the incubation period 4 μl of Steady-Glo reagent (Steady-Glo Luciferase assay system (Promega E2520) was added to each well and the plate read immediately in a Leadseeker Plate reader (Amersham Bioscience) using a 660 nm filter. Concentration effect curves were plotted and $EC_{50}$ values generated using a 4-parameter sigmoid fit using an in-house data analysis programme. Isoprenaline was run in every assay as a reference standard.

Examples 1 to 20 were tested according to the here above disclosed assays and the following results were obtained:

| Example No. | EC50 - beta2 (nM) | Ki - M3 (nM) |
|---|---|---|
| 1 | 0.88 | 3.4 |
| 2 | 0.32 | 1.1 |
| 3 | 0.14 | 1.4 |
| 4 | 1.3 | 0.28 |
| 5 | 0.2 | 0.3 |
| 6 | 0.19 | 2.4 |
| 7 | 0.049 | 2.1 |
| 8 | 0.035 | 0.31 |
| 9 | 4.8 | 1.1 |
| 10 | 0.26 | 1.10 |
| 11 | 2.2 | 1.5 |

-continued

| Example No. | EC50 - beta2 (nM) | Ki - M3 (nM) |
|---|---|---|
| 12 | 13.8 | 0.26 |
| 13 | 0.078 | 0.38 |
| 14 | 0.054 | 0.76 |
| 15 | 0.25 | 0.060 |
| 16 | 1.3 | 2.0 |
| 17 | 0.57 | 3.0 |
| 18 | 0.22 | 0.77 |
| 19 | 0.2 | 0.3 |
| 20 | 0.028 | 0.39 |

The invention claimed is:

1. 5-[(1R)-2-({2-[4-(4-{3-[(1R)-3-(diisopropylamino)-1-phenylpropyl]-4-hydroxyphenyl}butoxy)phenyl]ethyl}amino)-1-hydroxyethyl]-8-hydroxyquinolin-2(1H)-one, or a pharmaceutically acceptable salt thereof.

2. A pharmaceutical composition comprising an effective amount of a compound of claim 1, or a pharmaceutically acceptable salt thereof.

3. A pharmaceutical composition according to claim 2, further comprising one or more pharmaceutically acceptable excipients and/or additives.

4. A method of treating asthma or chronic obstructive pulmonary disease (COPD) in a mammal, said method comprising administering to said mammal in need thereof a therapeutically effective amount of a compound of claim 1, or a pharmaceutically acceptable salt or pharmaceutically acceptable quaternary ammonium salt of said compound.

* * * * *